US012448398B2

(12) United States Patent
Fuchs et al.

(10) Patent No.: US 12,448,398 B2
(45) Date of Patent: Oct. 21, 2025

(54) SEMI-SYNTHETIC ANALOGUES OF EPIPOLYTHIODIOXOPIPERAZINE ALKALOIDS

(71) Applicants: Ohio State Innovation Foundation, Columbus, OH (US); UNIVERSITY OF NORTH CAROLINA AT GREENSBORO, Greensboro, NC (US); THE BOARD OF TRUSTEES OF THE UNIVERSITY OF ILLINOIS, Chicago, IL (US); MYCOSYNTHETIX, INC., Hillsborough, NC (US)

(72) Inventors: James Robert Fuchs, Columbus, OH (US); Andrew Huntsman, Fort Jennings, OH (US); Nicholas Hunter Oberlies, Greensboro, NC (US); Chiraz Soumia Amrine, Greensboro, NC (US); Huzefa Raja, Greensboro, NC (US); Joanna Burdette, Chicago, IL (US); Cedric Pearce, Chapel Hill, NC (US)

(73) Assignees: Ohio State Innovation Foundation, Columbus, OH (US); University of North Carolina at Greensboro, Greensboro, NC (US); The Board of Trustees of the University of Illinois, Chicago, IL (US); Mycosynthetix, Inc., Hillssborough, NC (US)

( * ) Notice: Subject to any disclaimer, the term of this patent is extended or adjusted under 35 U.S.C. 154(b) by 912 days.

(21) Appl. No.: 17/613,640

(22) PCT Filed: May 22, 2020

(86) PCT No.: PCT/US2020/034268

§ 371 (c)(1),
(2) Date: Nov. 23, 2021

(87) PCT Pub. No.: WO2020/237169

PCT Pub. Date: Nov. 26, 2020

(65) Prior Publication Data

US 2022/0235072 A1 Jul. 28, 2022

Related U.S. Application Data

(60) Provisional application No. 62/851,939, filed on May 23, 2019.

(51) Int. Cl.

| | |
|---|---|
| ***C07D 513/22*** | (2006.01) |
| ***A61K 31/542*** | (2006.01) |
| ***A61P 35/00*** | (2006.01) |
| ***C07D 519/00*** | (2006.01) |

(52) U.S. Cl.

CPC .................................. *C07D 519/00* (2013.01)

(58) Field of Classification Search

CPC .. C07D 513/22; C07D 519/00; A61K 31/542; A61P 35/00

See application file for complete search history.

(56) References Cited

U.S. PATENT DOCUMENTS

| | | | |
|---|---|---|---|
| 2012/0219568 | A1 | 8/2012 | Liu et al. |
| 2014/0161785 | A1 | 6/2014 | Liu et al. |
| 2016/0222031 | A1 | 8/2016 | Kang et al. |

OTHER PUBLICATIONS

Altmann, Karl-Heinz, Fabienne Z. Gaugaz, and Raphael Schiess. "Diversity through semisynthesis: the chemistry and biological activity of semisynthetic epothilone derivatives." Molecular diversity 15.2 (2011): 383-399.

Amrine, Chiraz Soumia M., et al. "Media studies to enhance the production of verticillins facilitated by in situ chemical analysis." Journal of Industrial Microbiology and Biotechnology 45.12 (2018): 1053-1065.

Aragones, MI Hidalgo, et al. "Pharmacokinetics of oestrone-3-O-sulphamate." The Journal of Steroid Biochemistry and Molecular Biology 58.5-6 (1996): 611-617.

Bian, Linglin, et al. "Semi-synthesis and Structure-Activity Relationship of Neuritogenic Oleanene Derivatives." ChemMedChem 13.18 (2018): 1972-1977.

Boland, Edward W. "The Treatment of Rheumatoid Arthritis with Adreno-Corticosteroids and Their Synthetic Analogues: An Appraisal Of Certain Developments of The Past Decade." Annals of the New York Academy of Sciences 82.4 (1959): 887-901.

Boyer, Nicolas, et al. "Synthesis and anticancer activity of epipolythiodiketopiperazine alkaloids." Chemical science 4.4 (2013): 1646-1657.

Brophy, T. R., et al. "Bioavailability of oral dexamethasone during high dose steroid therapy in neurological patients." European journal of clinical pharmacology 24.1 (1983): 103-108.

Chin, Nai-Xun, and Harold C. Neu. "Ciprofloxacin, a quinolone carboxylic acid compound active against aerobic and anaerobic bacteria." Antimicrobial agents and Chemotherapy 25.3 (1984): 319-326.

Cohen, S. S. "Flaks, JG, Barner, HD, Loeb, MR, and Lichtenstein, J.: The mode of action of 5-fluorouracil and its derivatives." Proc. Nut/. Acud. Sci. USA. vol. 44. 1958.

Cragg, Gordon M., and David J. Newman. "Natural products as sources of anticancer agents: Current approaches and perspectives." Natural products as source of molecules with therapeutic potential (2018): 309-331.

(Continued)

*Primary Examiner* — Brenda L Coleman

(74) *Attorney, Agent, or Firm* — Meunier Carlin & Curfman LLC

(57) ABSTRACT

Disclosed herein are compounds, compositions, and methods for inhibiting a histone methyltransferase. The compounds are verticillin derivatives that exhibit anti-proliferative activity against cancer cells. The compounds, compositions, and methods can be used to treat a subject with cancer.

17 Claims, 26 Drawing Sheets

(56) References Cited

OTHER PUBLICATIONS

Duschinsky, Robert, Edward Pleven, and Charles Heidelberger. "The synthesis of 5-fluoropyrimidines." Journal of the American Chemical Society 79.16 (1957): 4559-4560.
El-Elimat, Tamam, et al. "Biosynthetically distinct cytotoxic polyketides from Setophoma terrestris." European journal of organic chemistry 2015.1 (2015): 109-121.
El-Elimat, Tamam, et al. "Greensporones: resorcylic acid lactones from an aquatic *Halenospora* sp." Journal of natural products 77.9 (2014): 2088-2098.
Fakhouri, Lara, et al. "Isolation, semisynthesis, covalent docking and transforming growth factor beta-activated kinase 1 (TAK1)-inhibitory activities of (5Z)-7-oxozeaenol analogues." Bioorganic & medicinal chemistry 23.21 (2015): 6993-6999.
FDA approves irinotecan as first-line therapy for colorectal cancer. Oncology (Williston Park) 2000, 14 (5), 652, 654.
Figueroa, Mario, et al. "Cytotoxic epipolythiodioxopiperazine alkaloids from filamentous fungi of the Bionectriaceae." The Journal of antibiotics 65.11 (2012): 559-564.
Fotherby, K. "Bioavailability of orally administered sex steroids used in oral contraception and hormone replacement therapy." Contraception 54.2 (1996): 59-69.
Fox, Ellen M., and Barbara J. Howlett. "Biosynthetic gene clusters for epipolythiodioxopiperazines in filamentous fungi." Mycological research 112.2 (2008): 162-169.
Fumoleau, P., et al. "Novel tubulin-targeting agents: anticancer activity and pharmacologic profile of epothilones and related analogues." Annals of oncology 18 (2007): v9-v15.
Gardiner, Donald M., Paul Waring, and Barbara J. Howlett. "The epipolythiodioxopiperazine (ETP) class of fungal toxins: distribution, mode of action, functions and biosynthesis." Microbiology 151.4 (2005): 1021-1032.
Gillis, Eric P., et al. "Applications of fluorine in medicinal chemistry." Journal of medicinal chemistry 58.21 (2015): 8315-8359.
Gu, Binbin, et al. "Tentative biosynthetic pathways of some microbial diketopiperazines." Applied microbiology and biotechnology 97.19 (2013): 8439-8453.
Guenard, Daniel, Francoise Gueritte-Voegelein, and Pierre Potier. "Taxol and taxotere: discovery, chemistry, and structure-activity relationships." Accounts of Chemical Research 26.4 (1993): 160-167.
Guo, Chun-Jun, et al. "Biosynthetic pathway for the epipolythiodioxopiperazine acetylaranotin in Aspergillus terreus revealed by genome-based deletion analysis." Journal of the American Chemical Society 135.19 (2013): 7205-7213.
Halperin, Shira D., et al. "Development of a direct photocatalytic C—H fluorination for the preparative synthesis of odanacatib." Organic letters 17.21 (2015): 5200-5203.
Harrison, Charlotte. "Patenting natural products just got harder." Nature Biotechnology 32.5 (2014): 403-405.
Harvey, Alan L., et al. "Current strategies for drug discovery through natural products." Expert opinion on drug discovery 5.6 (2010): 559-568.
Iwasa, Eriko, Yoshitaka Hamashima, and Mikiko Sodeoka. "Epipolythiodiketopiperazine alkaloids: total syntheses and biological activities." Israel Journal of Chemistry 51.3-4 (2011): 420-433.
Johnson, Mark E., Daniel Blankschtein, and Robert Langer. "Permeation of steroids through human skin." Journal of pharmaceutical sciences 84.9 (1995): 1144-1146.
Jordan, T. William, and Stephen J. Cordiner. "Fungal epipolythiodioxopiperazine toxins have therapeutic potential and roles in disease." Trends in Pharmacological Sciences 8.4 (1987): 144-149.
Joshi, Biren K., James B. Gloer, and Donald T. Wicklow. "New Verticillin and Glisoprenin Analogues from Gliocladium c atenulatum, a Mycoparasite of Aspergillus f lavus Sclerotia." Journal of natural products 62.5 (1999): 730-733.
Katagiri, Ken, et al. "Verticillin A, A New Anti-Biotic From Verticillium SF." The Journal of antibiotics 23.8 (1970): 420-422.
Kawato, Yasuyoshi, et al. "Antitumor activity of a camptothecin derivative, CPT-11, against human tumor xenografts in nude mice." Cancer chemotherapy and pharmacology 28.3 (1991): 192-198.
Kertesz, Vilmos, and Gary J. Van Berkel. "Sampling reliability, spatial resolution, spatial precision, and extraction efficiency in droplet-based liquid microjunction surface sampling." Rapid Communications in Mass Spectrometry 28.13 (2014): 1553-1560.
Kertesz, Vilmos, Taylor M. Weiskittel, and Gary J. Van Berkel. "An enhanced droplet-based liquid microjunction surface sampling system coupled with HPLC-ESI-MS/MS for spatially resolved analysis." Analytical and bioanalytical chemistry 407.8 (2015): 2117-2125.
Kim, Dooseop, et al. "(2 R)-4-Oxo-4-[3-(trifluoromethyl)-5, 6-dihydro [1, 2, 4] triazolo [4, 3-a] pyrazin-7 (8 H)-yl]-1-(2, 4, 5-trifluorophenyl) butan-2-amine: a potent, orally active dipeptidyl peptidase IV inhibitor for the treatment of type 2 diabetes." Journal of medicinal chemistry 48.1 (2005): 141-151.
Kim, Justin, and Mohammad Movassaghi. "Biogenetically-inspired total synthesis of epidithiodiketopiperazines and related alkaloids." Accounts of Chemical Research 48.4 (2015): 1159-1171.
Kim, Justin, James A. Ashenhurst, and Mohammad Movassaghi. "Total synthesis of (+)-11, 11'-dideoxyverticillin A." Science 324. 5924 (2009): 238-241.
Kim, Woojoo E., et al. "Mechanistic probes for the epimerization domain of nonribosomal peptide synthetases." ChemBioChem 20.2 (2019): 147-152.
Kinghorn, A. Douglas, et al. "Discovery of anticancer agents of diverse natural origin." Anticancer research 36.11 (2016): 5623-5637.
Kirk, Kenneth L. "Fluorination in medicinal chemistry: methods, strategies, and recent developments." Organic Process Research & Development 12.2 (2008): 305-321.
Kung, Stephanie H., et al. "Approaches and recent developments for the commercial production of semi-synthetic artemisinin." Frontiers in plant science 9 (2018): 87.
Lee, Richard E., et al. "Spectinamides: a new class of semisynthetic antituberculosis agents that overcome native drug efflux." Nature medicine 20.2 (2014): 152-158.
Liu, Feiyan, et al. "Verticillin chloroform solvate." Acta Crystallographica Section E: Structure Reports Online 62.3 (2006): o974-o976.
Lu, Chunwan, et al. "The MLL1-H3K4me3 axis-mediated PD-L1 expression and pancreatic cancer immune evasion." JNCI: journal of the National Cancer Institute 109.6 (2017). https://doi.org/10.1093/jnci/djw283.
McAlpine, J. B., et al., Boufridi, A. (2019). Correction: The value of universally available raw NMR data for transparency, reproducibility, and integrity in natural product research. Natural Product Reports. doi:10.1039/c8np90041h.
McElroy, Christopher, and Stefan Jennewein. "Taxol® biosynthesis and production: from forests to fermenters." Biotechnology of natural products. Springer, Cham, 2018. 145-185.
Meanwell, Nicholas A. "Fluorine and fluorinated motifs in the design and application of bioisosteres for drug design." Journal of medicinal chemistry 61.14 (2018): 5822-5880.
Muller, Klaus, Christoph Faeh, and François Diederich. "Fluorine in pharmaceuticals: looking beyond intuition." science 317.5846 (2007): 1881-1886.
Newman, David J. "Developing natural product drugs: Supply problems and how they have been overcome." Pharmacology & therapeutics 162 (2016): 1-9.
Newman, David J., and Gordon M. Cragg. "Natural products as sources of new drugs from 1981 to 2014." Journal of natural products 79.3 (2016): 629-661.
Nicolaou, K. C., et al. "Natural product-like combinatorial libraries based on privileged structures. 1. General principles and solid-phase synthesis of benzopyrans." Journal of the American Chemical Society 122.41 (2000): 9939-9953.
Nilanonta, Chongdee, et al. "Precursor-directed biosynthesis of beauvericin analogs by the insect pathogenic fungus Paecilomyces tenuipes BCC 1614." Tetrahedron 58.17 (2002): 3355-3360.

(56) References Cited

OTHER PUBLICATIONS

O'Hagan, David, and Hai Deng. "Enzymatic fluorination and biotechnological developments of the fluorinase." Chemical reviews 115.2 (2015): 634-649.
O'Leary, J., and F. M. Muggia. "Camptothecins: a review of their development and schedules of administration." European Journal of Cancer 34.10 (1998): 1500-1508.
Oberlies, Nicholas H., and David J. Kroll. "Camptothecin and taxol: historic achievements in natural products research." Journal of natural products 67.2 (2004): 129-135.
Paguigan, Noemi D., et al. "Enhanced dereplication of fungal cultures via use of mass defect filtering." The Journal of antibiotics 70.5 (2017): 553-561.
Paschall, Amy V., et al. "H3K9 trimethylation silences Fas expression to confer colon carcinoma immune escape and 5-fluorouracil chemoresistance." The Journal of Immunology 195.4 (2015): 1868-1882.
Puhalla, Shannon, and Adam Brufsky. "Ixabepilone: a new chemotherapeutic option for refractory metastatic breast cancer." Biologics: targets & therapy 2.3 (2008): 505.
Purser, Sophie, et al. "Fluorine in medicinal chemistry." Chemical Society Reviews 37.2 (2008): 320-330.
Rannard, Steve P., and Nicola J. Davis. "The selective reaction of primary amines with carbonyl imidazole containing compounds: selective amide and carbamate synthesis." Organic letters 2.14 (2000): 2117-2120.
Ringel, Israel, and Susan Band Horwitz. "Studies with RP 56976 (taxotere): a semisynthetic analogue of taxol." JNCI: Journal of the National Cancer Institute 83.4 (1991): 288-291.
Rivera-Chávez, José, et al. "Biosynthesis of fluorinated peptaibols using a site-directed building block incorporation approach." Journal of natural products 80.6 (2017): 1883-1892.
Romanov-Michailidis, Fedor, Laure Guénée, and Alexandre Alexakis. "Enantioselective Organocatalytic Fluorination-Induced Wagner-Meerwein Rearrangement." Angewandte Chemie 125.35 (2013): 9436-9440.
Saverino, Daniele, et al. "Antibacterial profile of flurithromycin, a new macrolide." Journal of Antimicrobial Chemotherapy 30.3 (1992): 261-272.
Sharma, Prabodh Chander, et al. "Ciprofloxacin: review on developments in synthetic, analytical, and medicinal aspects." Journal of enzyme inhibition and medicinal chemistry 25.4 (2010): 577-589.
Sica, Vincent P., et al. "Dereplicating and spatial mapping of secondary metabolites from fungal cultures in situ." Journal of natural products 78.8 (2015): 1926-1936.
Sica, Vincent P., et al. "In situ mass spectrometry monitoring of fungal cultures led to the identification of four peptaibols with a rare threonine residue." Phytochemistry 143 (2017): 45-53.
Sica, Vincent P., et al. "Optimizing production and evaluating biosynthesis in situ of a herbicidal compound, mevalocidin, from *Coniolariella* sp." Journal of Industrial Microbiology and Biotechnology 43.8 (2016): 1149-1157.
Sica, Vincent P., et al. "Spatial and temporal profiling of griseofulvin production in Xylaria cubensis using mass spectrometry mapping." Frontiers in microbiology 7 (2016): 544.
Sica, Vincent P., Tamam El-Elimat, and Nicholas H. Oberlies. "In situ analysis of Asimina triloba (paw paw) plant tissues for acetogenins via the droplet-liquid microjunction-surface sampling probe coupled to UHPLC-PDA-HRMS/MS." Analytical Methods 8.32 (2016): 6143-6149.
Siegel, Rebecca L., Kimberly D. Miller, and Ahmedin Jemal. "Cancer statistics, 2019." CA: a cancer journal for clinicians 69.1 (2019): 7-34.
Society, A. C., American Cancer Society: Cancer Facts & Figures 2019. Atlanta, Ga: American Cancer Society 2019.
Süssmuth, Roderich D., and Andi Mainz. "Nonribosomal peptide synthesis—principles and prospects." Angewandte Chemie International Edition 56.14 (2017): 3770-3821.
Tanner, Martin E. "Understanding nature's strategies for enzyme-catalyzed racemization and epimerization." Accounts of chemical research 35.4 (2002): 237-246.
Thiericke, R., and J. Rohr. "Biological variation of microbial metabolites by precursor-directed biosynthesis." Natural Product Reports 10.3 (1993): 265-289.
Toscano, Luciano, et al. "New fluorinated erythromycins obtained by mutasynthesis." The Journal of Antibiotics 36.11 (1983): 1439-1450.
Tsuruo, Takashi, et al. "Antitumor effect of CPT-11, a new derivative of camptothecin, against pleiotropic drug-resistant tumors in vitro and in vivo." Cancer chemotherapy and pharmacology 21.1 (1988): 71-74.
Walker, Mark C., and Michelle CY Chang. "Natural and engineered biosynthesis of fluorinated natural products." Chemical Society Reviews 43.18 (2014): 6527-6536.
Walko, Christine M., and Celeste Lindley. "Capecitabine: a review." Clinical therapeutics 27.1 (2005): 23-44.
Wang, Jiang, et al. "Fluorine in pharmaceutical industry: fluorine-containing drugs introduced to the market in the last decade (2001-2011)." Chemical reviews 114.4 (2014): 2432-2506.
Wong, David T., Kenneth W. Perry, and Frank P. Bymaster. "The discovery of fluoxetine hydrochloride (Prozac)." Nature reviews Drug discovery 4.9 (2005): 764-774.
Xu, Hui, et al. "Semisynthesis and quantitative structure—activity relationship (QSAR) study of novel aromatic esters of 4'-demethyl-4-deoxypodophyllotoxin as insecticidal agents." Journal of agricultural and food chemistry 57.17 (2009): 7919-7923.
Xu, Yuquan, et al. "Cytotoxic and antihaptotactic beauvericin analogues from precursor-directed biosynthesis with the insect pathogen Beauveria bassiana ATCC 7159." Journal of natural products 70.9 (2007): 1467-1471.
Yoshioka, Takuya, et al. "Semisynthesis and structure-activity studies of uncarinic acid C isolated from uncaria rhynchophylla as a specific inhibitor of the nucleation phase in amyloid β42 aggregation." Journal of Natural Products 79.10 (2016): 2521-2529.
Zewdu, Abbie, et al. "Verticillin A inhibits leiomyosarcoma and malignant peripheral nerve sheath tumor growth via induction of apoptosis." Clinical & experimental pharmacology 6.6 (2016) 6 (6), 221-234.
Zhang, Yi-Xiang, et al. "11, 11'-Dideoxy-verticillin: a natural compound possessing growth factor receptor tyrosine kinase-inhibitory effect with anti-tumor activity." Anti-cancer drugs 16.5 (2005): 515-524.
Zhou, Yu, et al. "Next generation of fluorine-containing pharmaceuticals, compounds currently in phase II-III clinical trials of major pharmaceutical companies: new structural trends and therapeutic areas." Chemical reviews 116.2 (2016): 422-518.
European Patent Office. Extended search report. Issued in European Application No. 20809372.4. Jun. 22, 2023. 7 pages.
Minato et al. (1971). Verticillin A, a new antibiotic from *Verticillium* sp. Journal of the Chemical Society D: Chemical Communications, (1), 44-45.
Saito et al. (1985). Chetracin A, a new epipolythiodioxopiperazine having a tetrasulfide bridge from Chaetomium abuense and C. retardatum. Tetrahedron letters, 26(39), 4731-4734.
International Search Report and Written Opinion, issued by the International Searching Authority (ISA/US) in PCT Application No. PCT/US2020/034268 on Aug. 11, 2020. 8 pages.
Figueroa et al., Cytotoxic epipolythiodioxopiperazine alkaloids from filamentous fungi of the Bionectriaceae, The Journal of Antibiotics, vol. 65, Sep. 12, 2012, pp. 559-564.
Minato et al., Studies on the Metabolites of *Verticillium* sp. Structures of Verticillins A, B, and C, Journal of the Chemical Society, Perkin Transactions 1, Jan. 1, 1973. pp. 1819-1825. [Retrieved on Jul. 22, 2020, https://bubs.rsc.org/en/content/articlelanding/1973/p1/p19730001819/unauth].

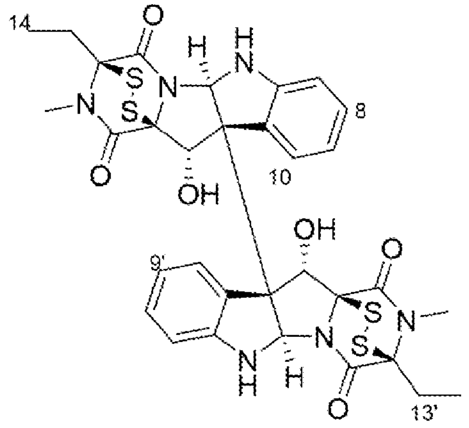
1
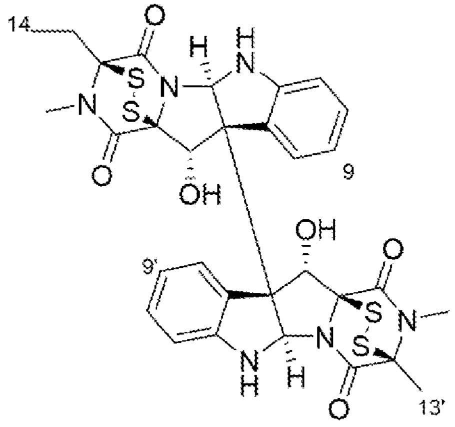
2
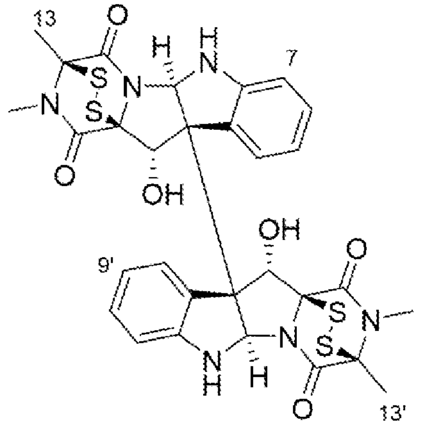
3
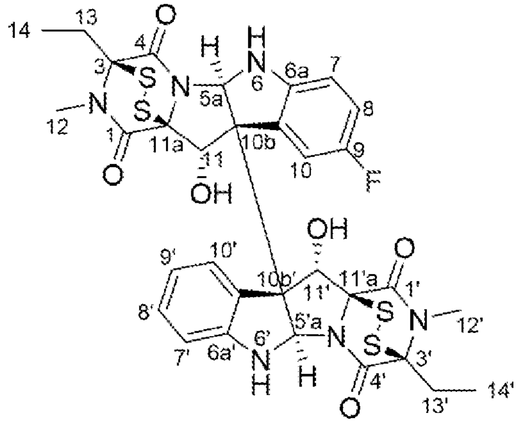
4
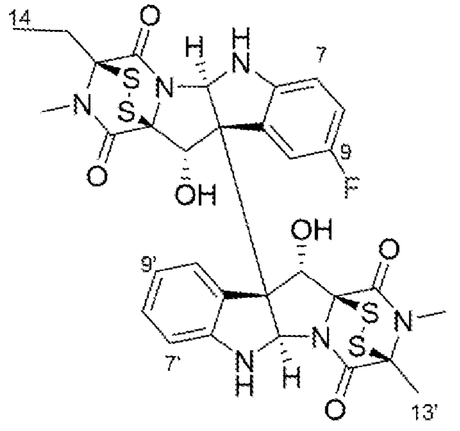
5
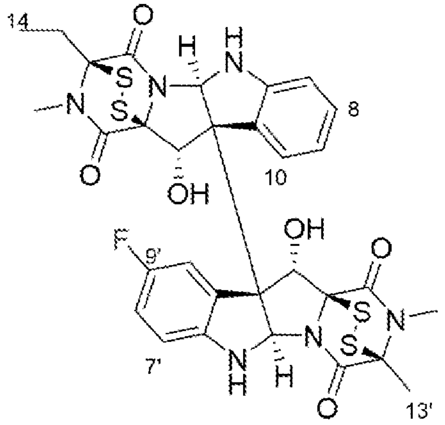
6
FIG. 1

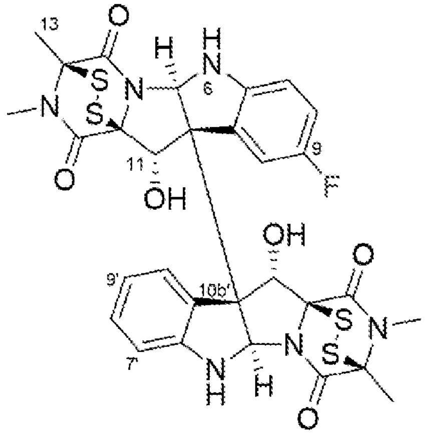
7
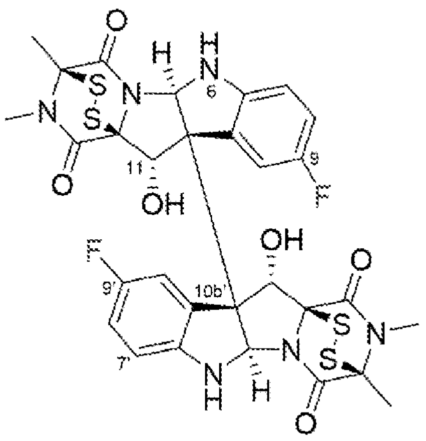
8
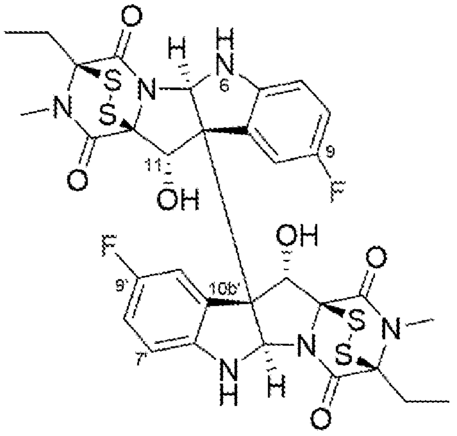
9
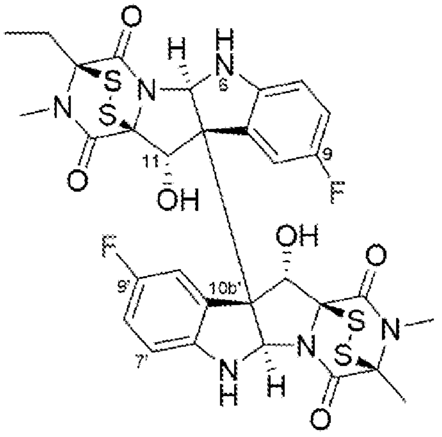
10
FIG. 1 (cont'd)

| Position | $\delta_H$, mult (J in Hz) | | | | | | |
|---|---|---|---|---|---|---|---|
| | (4) | (5) | (6) | (7) | (8) | (9) | (10) |
| 1 | - | - | - | - | - | - | - |
| 3 | - | - | - | - | - | - | - |
| 4 | - | - | - | - | - | - | - |
| 5a | 5.68, s | 5.67, s | 5.70, s | 5.67, s | 5.65, s | 5.66, s | 5.66, s |
| 6a | - | - | - | - | - | - | - |
| 7 | 6.58, dd (8.6, 4.4) | 6.58, dd (8.6, 4.4) | 6.65, dd (7.7, 1.0) | 6.58, dd (8.6, 4.4) | 6.59, dd (8.6, 4.4) | 6.59, dd (8.6, 4.4) | 6.59, m (8.8, 4.4) |
| 8 | 6.86, td (8.6, 2.7) | 6.86, td (8.6, 2.7) | 7.13, td (7.7, 1.3) | 6.86, td (8.6, 2.7) | 6.86, td (8.6, 2.7) | 6.88, td (8.6, 2.6) | 6.86[a], td (8.8, 2.8) |
| 9 | - | - | 6.81, td (7.7, 1.0) | - | - | - | - |
| 10 | 7.63, dd (9.4, 2.7) | 7.61, dd (9.4, 2.7) | 7.81, dd (7.7, 1.3) | 7.61, dd (9.4, 2.7) | 7.60, dd (9.4, 2.7) | 7.60, dd (9.4, 2.6) | 7.61[b], m (9.4, 2.8) |
| 10a | - | - | - | - | - | - | - |
| 10b | - | - | - | - | - | - | - |
| 11 | 5.16, s | 5.15, s | 5.15, s | 5.14, s | 5.13, s | 5.15, s | 5.14[c], s |
| 11a | - | - | - | - | - | - | - |
| 12 | 3.02[a], s | 3.02, s 3.01, s | 3.03, s | 3.01[a], s | 3.01, s | 3.04, s | 3.02[d], s |
| 13 | 2.17, m, 2.38, m | 2.17, m 2.37, m | 2.18, m 2.39, m | 1.88, s, 1.90, s | 1.91, s | 2.19, m, 2.39, m | 2.19, m, 2.39, m |
| 14 | 1.25[b], t (7.2) | 1.22, t (7.2) | 1.25, t (7.2) | | - | 1.26, t (7.1) | 1.26, t (7.0) |
| 6-NH | 5.05, s | 5.05, s | 5.15, s | 4.99, s | 5.01, s | 5.66, s | 5.05[e], s, |
| 11-OH | 5.59, s | 5.59, s | 5.63, s | 5.69, s | 5.76, s | 5.07, s | 5.66[f], s |
| 1′ | - | - | - | - | - | - | - |
| 3′ | - | - | - | - | - | - | - |
| 4′ | - | - | - | - | - | - | - |
| 5a′ | 5.70, s | 5.70, s | 5.68, s | 5.69, s | 5.65, s | 5.66, s | 5.66, s |
| 6a′ | - | - | - | - | - | - | - |
| 7′ | 6.65, dd (7.6, 1.0) | 6.66, dd (7.7, 1.0) | 6.58, dd (4.4, 8.6) | 6.65, dd (7.7, 1.0) | 6.59, dd (8.6, 4.4) | 6.59, dd (8.6, 4.4) | 6.59, m (8.8, 4.4) |
| 8′ | 7.15, td (7.6, 1.2) | 7.15, td (7.7, 1.2) | 6.87, td (8.6, 2.7) | 7.14, td (7.7, 0.9) | 6.86, td (8.6, 2.6) | 6.88, td (8.6, 2.7) | 6.88[a], td (8.8, 2.8) |
| 9′ | 6.83, td (7.6, 1.0) | 6.84, td (7.7, 1.0) | - | 6.82, td (7.7, 1.0) | - | - | - |
| 10′ | 7.83, dd (7.6, 1.2) | 7.84, dd (7.7, 1.2) | 7.64, dd (9.4, 2.7) | 7.82, dd (7.7, 0.9) | 7.60, dd (9.4, 2.6) | 7.60, dd (9.5, 2.7) | 7.63[b], m (9.4, 2.8) |
| 10a′ | - | - | - | - | - | - | - |
| 10b′ | - | - | - | - | - | - | - |
| 11′ | 5.14, s | 5.13, s | 5.13, s | 5.12, s | 5.13, s | 5.15, s | 5.15[c], s |
| 11a′ | - | - | - | - | - | - | - |
| 12′ | 3.03[a], s | 3.01, s | 2.99, s | 2.99[a], s | 3.01, s | 3.04, s | 3.04[d], s |
| 13′ | 2.17, m, 2.38, m | 1.90, s | 1.89, s | 1.88, s, 1.90, s | 1.91, s | 2.19, m, 2.39, m | 1.91, s |
| 14′ | 1.22[b], t (7.2) | | | | - | 1.26, t (7.1) | |
| 6′-NH | 5.15, s | 5.10, s | 4.99, s | 5.10, s | 5.01, s | 5.66, s | 5.07[e], s |
| 11′-OH | 5.64, s | 5.74, s | 5.70, s | 5.73, s | 5.76, s | 5.07, s | 5.77[f], s |

[a-f] Assignments may be interchangeable

FIG. 2

| Position | δc mult (*J** in Hz) | | | | |
|---|---|---|---|---|---|
| | (4) | (5) | (6) | (7) | (8) |
| 1 | 167.1 | 167.1 | 167.1 | 166.1 | 166.0 |
| 3 | 77.4[a] | 77.5 | 77.4 | 73.0[a] | 73.0 |
| 4 | 161.4 | 161.4 | 161.4 | 162.2 | 162.3 |
| 5a | 82.0 | 82.0 | 81.9 | 82.0 | 81.9 |
| 6a | 144.9, d (1.3) | 144.9, d (1.1) | 148.7 | 144.8, d (1.2) | 144.8 |
| 7 | 111.1, d (8.5) | 111.1, d (8.5) | 110.8 | 111.2, d (8.6) | 111.3, d (8.3) |
| 8 | 116.6, d (24.5) | 116.6, d (23.6) | 130.1 | 116.6, d (24.7) | 116.7, d (23.9) |
| 9 | 157.6, d (235.6) | 157.6, d (236.3) | 120.5 | 157.6, d (236.2) | 157.6, d (236.9) |
| 10 | 115.5, d (25.4) | 115.5, d (25.7) | 128.2 | 115.5, d (25.5) | 115.6, d (26.6) |
| 10a | 130.8, d (8.5) | 130.8, d (8.6) | 128.9 | 130.8, d (8.6) | 130.4, d (8.7) |
| 10b | 65.9, d (1.9) | 65.9, d (1.9) | 65.6 | 66.0, d (1.6) | 65.8, d (1.6) |
| 11 | 83.8 | 83.7 | 83.0 | 83.6 | 83.4 |
| 11a | 76.6 | 76.6 | 76.7 | 76.4 | 76.2 |
| 12 | 28.0 | 28.0 | 28.0 | 27.20[a] | 27.2 |
| 13 | 24.6[a] | 24.5 | 24.6 | 17.4 | 17.5 |
| 14 | 9.9[a] | 9.8 | 9.8 | - | - |
| 1′ | 167.1 | 166.1 | 166.1 | 166.1 | 166.0 |
| 3′ | 77.5[a] | 72.9 | 73.0 | 72.9[a] | 73.0 |
| 4′ | 161.4 | 162.3 | 162.3 | 162.3 | 162.3 |
| 5a′ | 81.9 | 81.9 | 82.0 | 81.9 | 81.9 |
| 6a′ | 148.8 | 148.7 | 144.8, d (1.4) | 148.6 | 144.8 |
| 7′ | 110.8 | 110.8 | 111.2, d (8.5) | 110.8 | 111.3, d (8.3) |
| 8′ | 130.1 | 130.2 | 116.6, d (23.8) | 130.1 | 116.7, d (23.9) |
| 9′ | 120.5 | 120.5 | 157.6, d (236.0) | 120.5 | 157.6, d (236.9) |
| 10′ | 128.2 | 128.3 | 115.6, d (25.5) | 128.2 | 115.6, d (26.6) |
| 10a′ | 128.9 | 128.9 | 130.8, d (8.6) | 128.9 | 130.4, d (8.7) |
| 10b′ | 65.5 | 65.6 | 66.0 d (1.9) | 65.7 | 65.8, d (1.6) |
| 11′ | 83.0 | 82.8 | 83.6 | 82.8 | 83.4 |
| 11a′ | 76.7 | 76.4 | 76.3 | 76.3 | 76.2 |
| 12′ | 28.0 | 27.2 | 27.2 | 27.18[a] | 27.2 |
| 13′ | 24.5[a] | 17.5 | 17.5 | 17.423 | 17.5 |
| 14′ | 9.8[a] | - | - | - | - |

[a] Assignments may be interchangeable
* *J* is for C-F coupling

FIG. 3

| Compound | $IC_{50}$(nM) | | |
|---|---|---|---|
| | MDA-MB-231 | OVCAR 3 | MDA-MB-435 |
| Verticillin H (**1**) | 71 | 101 | 88 |
| Sch 52901 (**2**) | 22 | 30 | 30 |
| Verticillin A (**3**) | 43 | 37 | 37 |
| 9-F-Verticillin H (**4**) | 46 | 39 | 49 |
| 9-F-Sch 52901 (**5**) | 37 | 37 | 39 |
| 9′-F-Sch 52901 (**6**) | 70 | 104 | 72 |
| 9-F-Verticillin A (**7**) | 230 | 181 | 237 |
| 9, 9′-di F-Verticillin A (**8**) | 59 | 75 | 65 |
| 9, 9′-di F-Verticillin H (**9**) | 844 | 919 | 826 |
| 9, 9′-di F- Sch 52901 (**10**) | 105 | 175 | 127 |
| Taxol (control) | 166 | 5 | 0.4 |

MDA-MB-435: Human melanoma cancer cells, OVCAR3: Human ovarian cancer cells, MDA-MB-231: Human breast cancer cells.

FIG. 4

| Position | $\delta_C$ | $\delta_H$, mult (*J* in Hz) |
|---|---|---|
| 1, 1' | 167.4 | - |
| 3, 3' | 77.5 | - |
| 4, 4' | 161.6 | - |
| 5a, 5a' | 82.1 | 5.73, s |
| 6a, 6a' | 148.9 | - |
| 7, 7' | 110.9 | 6.64, dd (7.8, 0.9) |
| 8, 8' | 130.1 | 7.14, td (7.8, 1.1) |
| 9, 9' | 120.6 | 6.83, td (7.8, 0.9) |
| 10, 10' | 128.3 | 7.84, dd (7.8, 1.1) |
| 10a, 10a' | 129.5 | - |
| 10b, 10b' | 65.8 | - |
| 11, 11' | 83.3 | 5.14, s |
| 11a, 11a' | 76.9 | - |
| 12, 12' | 28.1 | 3.01, s |
| 13, 13' | 24.7 | 2.16, m<br>2.37, m |
| 14, 14' | 9.9 | 1.21, t (7.2) |
| 6-NH, 6'-NH | - | 5.57, s |

| Position | $\delta_C$ | $\delta_H$, mult ($J$ in Hz) | Position | $\delta_C$ | $\delta_H$, mult ($J$ in Hz) |
|---|---|---|---|---|---|
| 1 | 162.5[a] | - | 1' | 161.5[a] | - |
| 3 | 77.5[a] | - | 3' | 76.6[a] | - |
| 4 | 167.3[a] | - | 4' | 166.3[a] | - |
| 5a | 82.1 | 5.73, s | 5a' | 82.1 | 5.73, s |
| 6a | 148.8 | - | 6a' | 148.8 | - |
| 7 | 111.0 | 6.65, dd (7.6, 1.0) | 7' | 111.0 | 6.65, dd (7.3, 1.0) |
| 8 | 128.3 | 7.15, ddd (7.6, 7.4, 1.1) | 8' | 128.3 | 7.13, ddd (7.6, 7.3, 1.1) |
| 9 | 120.6 | 6.84, ddd (7.8, 7.4, 1.0) | 9' | 120.6 | 6.81, ddd (7.8, 7.6, 1.0) |
| 10 | 129.5 | 7.84, dd (7.8, 1.1) | 10' | 129.5 | 7.82, dd (7.8, 1.1) |
| 10a | 130.1 | - | 10a' | 130.1 | - |
| 10b | 66.0[a] | - | 10b' | 65.8[a] | - |
| 11 | 83.3[a] | 5.15, s | 11' | 83.1 | 5.15, s |
| 11a | 73.0 | - | 11a' | 73.0[a] | - |
| 12 | 28.1[a] | 3.01[b], s | 12' | 27.3[a] | 2.99[b], s |
| 13 | 17.6 | 2.16, m<br>2.36, m | 13' | 24.7 | 1.89, s |
| 14 | 9.9 | 1.22, t (7.1) | - | - | - |
| 6-NH | - | 5.09[b], s | 6'-NH | - | 5.14[b], s |
| 11-OH | - | 5.56[b], s | 11'-OH | - | 5.67[b], s |

[a, b] The assignments may be interchangeable.

| Position | $\delta_C$ | $\delta_H$, mult (*J* in Hz) |
|---|---|---|
| 1, 1' | 162.5 | - |
| 3, 3' | 76.6 | - |
| 4, 4' | 166.3 | - |
| 5a, 5a' | 82.1 | 5.72, s |
| 6a, 6a' | 148.8 | - |
| 7, 7' | 111.0 | 6.66, dd (7.8, 0.9) |
| 8, 8' | 128.3 | 7.14, td (7.8, 1.1) |
| 9, 9' | 120.6 | 6.82, td (7.8, 0.9) |
| 10, 10' | 130.1 | 7.83, dd (7.8, 1.1) |
| 10a, 10a' | 129.5 | - |
| 10b, 10b' | 66.0 | - |
| 11, 11' | 83.1 | 5.14, s |
| 11a, 11a' | 73.0 | - |
| 12, 12' | 27.3 | 2.99, s |
| 13, 13' | 17.6 | 1.89, s |
| 6-NH, 6'-NH | - | 5.09[a], s |
| 11-OH, 11'-OH | - | 5.66[a], s |

[a] The assignments may be interchangeable.

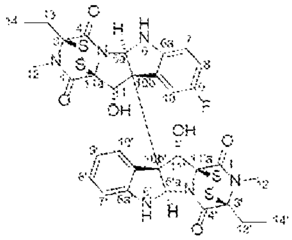

| Position | $\delta_C$, mult (J in Hz) | $\delta_H$, mult (J in Hz) | HMBC ($^1H \rightarrow ^{13}C$) | Position | $\delta_C$ mult | $\delta_H$, mult (J in Hz) | HMBC ($^1H \rightarrow ^{13}C$) |
|---|---|---|---|---|---|---|---|
| 1 | 167.1 | - | | 1' | 167.1 | - | |
| 3 | 77.4[a] | - | | 3' | 77.5[a] | - | |
| 4 | 161.4 | - | | 4' | 161.4 | - | |
| 5a | 82.0 | 5.68, s | 4, 10a, 10b, 11, 11a | 5a' | 81.9 | 5.70, s | 4', 10a', 10b', 11', 11a' |
| 6a | 144.9, d (1.3) | - | | 6a' | 148.8 | - | |
| 7 | 111.1, d (8.5) | 6.58, dd (8.6, 4.4) | 9, 10a | 7' | 110.8 | 6.65, dd (7.6, 1.0) | 9', 10a' |
| 8 | 116.6, d (24.5) | 6.86, td (8.6, 2.7) | 6a, 9, 10 | 8' | 130.1 | 7.15, td (7.6, 1.2) | 6a', 10' |
| 9 | 157.6, d (235.6) | - | | 9' | 120.5 | 6.83, td (7.6, 1.0) | 7', 10a' |
| 10 | 115.5, d (25.4) | 7.63, dd (9.4, 2.7) | 6a, 8, 9, 10a, 10b | 10' | 128.2 | 7.53, dd (7.6, 1.2) | 6a', 8', 10b' |
| 10a | 130.8, d (8.5) | - | | 10a' | 128.9 | - | |
| 10b | 65.9, d (1.9) | - | | 10b' | 65.5 | - | |
| 11 | 83.8 | 5.18, s | 6a, 10a, 11a | 11' | 83.0 | 5.14, s | 6a', 11a' |
| 11a | 76.6 | - | | 11a' | 76.7 | - | |
| 12 | 28.0 | 3.02[a], s | 1, 3 | 12' | 28.0 | 3.03[a], s | 1', 3' |
| 13 | 24.6[a] | 2.17, m, 2.38, m | 3, 4, 14 | 13' | 24.5[a] | 2.17, m, 2.38, m | 3', 4', 14' |
| 14 | 9.9[b] | 1.25[b], t (7.2) | 3, 13 | 14' | 9.8[b] | 1.22[b], t (7.2) | 3', 13' |
| 6-NH | - | 5.05, s | 6a, 7, 10a, 10b | 6'-NH | - | 5.15, s | 6a', 7', 10a', 10b' |
| 11-OH | - | 5.59, s | 10a, 10b, 11a | 11'-OH | - | 5.64, s | 10a', 10b', 11a' |

[a, b] The assignments may be interchangeable

FIG. 9

| Position | $\delta_C$, mult ($J$ in Hz) | $\delta_H$, mult ($J$ in Hz) | HMBC ($^1H \rightarrow ^{13}C$) | Position | $\delta_C$ | $\delta_H$, mult ($J$ in Hz) | HMBC ($^1H \rightarrow ^{13}C$) |
|---|---|---|---|---|---|---|---|
| 1 | 167.1 | - | | 1' | 166.1 | - | |
| 3 | 77.5 | - | | 3' | 72.9 | - | |
| 4 | 161.4 | - | | 4' | 162.3 | - | |
| 5a | 82.9 | 5.67, s | 4, 10a, 10b, 11, 11a | 5a' | 81.9 | 5.70, s | 4', 10a', 10b', 11', 11a' |
| 6a | 144.9, d (1.1) | - | | 6a' | 148.7 | - | |
| 7 | 111.1, d (8.5) | 6.58, dd (8.6, 4.4) | 9, 10a | 7' | 110.8 | 6.66, dd (7.7, 1.0) | 9', 10a' |
| 8 | 116.6, d (23.6) | 6.86, td (8.6, 2.7) | 6a, 9, 10 | 8' | 130.2 | 7.15, td (7.7, 1.2) | 6a', 10' |
| 9 | 157.6, d (236.3) | - | | 9' | 120.5 | 6.84, td (7.7, 1.0) | 7', 10a' |
| 10 | 115.5, d (25.7) | 7.61, dd (9.4, 2.7) | 6a, 8, 9, 10a, 10b | 10' | 128.3 | 7.84, dd (7.7, 1.2) | 6a', 8', 10b' |
| 10a | 130.8, d (8.6) | - | | 10a' | 128.9 | - | |
| 10b | 65.9, d (1.9) | - | | 10b' | 65.6 | - | |
| 11 | 83.7 | 5.15, s | 6a, 10a, 10b, 11a | 11' | 82.8 | 5.13, s | 6a', 10a', 10b', 11a' |
| 11a | 76.6 | - | | 11a' | 76.4 | - | |
| 12 | 28.0 | 3.02, s<br>3.01, s | 1, 3 | 12' | 27.2 | 3.01, s | 1', 3' |
| 13 | 24.5 | 2.17, m<br>2.37, m | 3, 4, 14 | 13' | 17.5 | 1.90, s | 3', 4' |
| 14 | 9.8 | 1.22, t (7.2) | 3, 13 | | | | |
| 6-NH | - | 5.05, s | 5a, 6a, 7, 10a, 10b | 6'-NH | - | 5.16, s | 5a', 7', 10b' |
| 11-OH | - | 5.59, s | 5a, 10b, 11a | 11'-OH | - | 5.74, s | 5a', 10b', 11a' |

| Position | $\delta_C$ | $\delta_H$, mult ($J$ in Hz) | HMBC ($^1H \rightarrow ^{13}C$) | Position | $\delta_C$, mult ($J$ in Hz) | $\delta_H$, mult ($J$ in Hz) | HMBC ($^1H \rightarrow ^{13}C$) |
|---|---|---|---|---|---|---|---|
| 1 | 167.1 | - | | 1' | 166.1 | - | |
| 3 | 77.4 | - | | 3' | 73.0 | - | |
| 4 | 161.4 | - | | 4' | 162.3 | - | |
| 5a | 81.9 | 5.70, s | 10a, 10b, 11 | 5a' | 82.0 | 5.68, s | 10a', 10b', 11' |
| 6a | 145.7 | - | | 6a' | 144.8, d (1.4) | - | |
| 7 | 110.8 | 6.65, dd (7.7, 1.9) | 9, 10a | 7' | 111.2, d (8.5) | 6.55, dd (4.4, 8.6) | 9', 10a' |
| 8 | 130.1 | 7.13, td (7.7, 1.3) | 6a, 10 | 8' | 116.6, d (23.8) | 6.87, td (8.6, 2.7) | 6a', 9', 10' |
| 9 | 120.5 | 6.81, td (7.7, 1.0) | 10a | 9' | 157.6, d (236.0) | - | |
| 10 | 128.2 | 7.81, dd (7.7, 1.3) | 6a, 8, 10a, 10b | 10' | 115.6, d (25.5) | 7.64, dd (9.4, 2.7) | 6a', 8', 9', 10a', 10b' |
| 10a | 128.9 | - | | 10a' | 130.8, d (8.6) | - | |
| 10b | 65.6 | - | | 10b' | 66.0 d (1.9) | - | |
| 11 | 83.0 | 5.15, s | 6a, 10a, 11a | 11' | 83.6 | 5.15, s | 6a', 10a', 11a' |
| 11a | 76.7 | - | | 11a' | 76.5 | - | |
| 12 | 28.9 | 3.05, s | 1, 3 | 12' | 27.2 | 2.99, s | 1', 3' |
| 13 | 24.6 | 2.18, m | 3, 4 | 13' | 17.5 | 1.89, s | 3', 4' |
| | | 2.39, m | | | | | |
| 14 | 9.8 | 1.25, t (7.2) | 3 | | | | |
| 6-NH | - | 5.17, s | 10a, 10b | 6'-NH | - | 4.99, s | 10a', 10b' |
| 11-OH | - | 5.63, s | 10b, 11, 11a | 11'-OH | - | 5.70, s | 10b', 11', 11a' |

| Position | $\delta_C$, mult ($J$ in Hz) | $\delta_H$, mult ($J$ in Hz) | HMBC ($^1H \rightarrow {}^{13}C$) | Position | $\delta_C$, mult | $\delta_H$, mult ($J$ in Hz) | HMBC ($^1H \rightarrow {}^{13}C$) |
|---|---|---|---|---|---|---|---|
| 1 | 166.1 | - | | 1' | 166.1 | - | |
| 3 | 73.0* | - | | 3' | 72.9* | - | |
| 4 | 162.2 | - | | 4' | 162.3 | - | |
| 5a | 82.0 | 5.67, s | 4, 10a, 10b, 11, 11a | 5a' | 81.9 | 5.69, s | 4', 10a', 10b', 11', 11a' |
| 6a | 144.8, d (1.2) | - | | 6a' | 148.6 | - | |
| 7 | 111.2, d (8.6) | 6.53, dd (8.6, 4.4) | 9, 10b | 7' | 110.8 | 6.65, dd (7.7, 1.0) | 9', 10a' |
| 8 | 116.6, d (24.7) | 6.86, td (8.6, 2.7) | 6a, 9, 10 | 8' | 130.1 | 7.14, td (7.7, 0.8) | 6a', 10' |
| 9 | 157.6, d (236.2) | - | | 9' | 120.5 | 6.82, td (7.7, 1.0) | 7', 10a' |
| 10 | 115.5, d (25.5) | 7.61, dd (9.4, 2.7) | 6a, 8, 9, 10b | 10' | 128.2 | 7.82, dd (7.7, 0.9) | 6a', 8', 10b' |
| 10a | 130.6, d (8.6) | - | | 10a' | 128.9 | - | |
| 10b | 66.0, d (1.6) | - | | 10b' | 65.7 | - | |
| 11 | 83.6 | 5.14, s | 6a, 10a, 10b, 11a | 11' | 82.8 | 5.12, s | 6a', 10a', 10b', 11a' |
| 11a | 76.4 | - | | 11a' | 76.3 | - | |
| 12 | 27.20* | 3.01*, s | 1, 3 | 12' | 27.15* | 2.99*, s | 1', 3' |
| 13 | 17.4 | 1.88, s, 1.90, s | 3, 4 | 13' | 17.4 | 1.88, s, 1.90, s | 3', 4' |
| 6-NH | - | 4.99, s | 6a, 7, 10a, 10b | 6'-NH | - | 5.10, s | 6a', 7', 10a', 10b' |
| 11-OH | - | 5.69, s | 10a, 10b | 11'-OH | - | 5.73, s | 10a', 10b' |

* The assignments may be interchangeable.

| Position | $\delta_C$, mult ($J$ in Hz) | $\delta_H$, mult ($J$ in Hz) | HMBC ($^1H \rightarrow ^{13}C$) |
|---|---|---|---|
| 1, 1' | 166.0 | - | |
| 3, 3' | 73.0 | - | |
| 4, 4' | 162.3 | - | |
| 5a, 5a' | 81.9 | 5.65, s | 4, 4', 10a, 10a', 10b, 10b', 11, 11', 11a, 11a' |
| 6a, 6a' | 144.8 | - | |
| 7, 7' | 111.3, d (8.3) | 6.59, dd (8.6, 4.4) | 9, 9', 10a, 10a' |
| 8, 8' | 116.7, d (23.9) | 6.86, td (8.6, 2.7) | 6a, 6a', 9, 9', 10, 10' |
| 9, 9' | 157.6, d (236.9) | - | |
| 10, 10' | 115.6, d (26.6) | 7.60, dd (9.4, 2.7) | 6a, 6a', 8, 8', 9, 9',10a, 10a',10b, 10b' |
| 10a, 10a' | 130.4, d (8.7) | - | |
| 10b, 10b' | 65.8, d (1.6) | - | |
| 11, 11' | 83.4 | 5.13, s | 6a, 6a', 10a, 10a', 10b, 10b', 11a, 11a' |
| 11a, 11a' | 76.2 | - | |
| 12, 12' | 27.2 | 3.01, s | 1, 1', 3, 3' |
| 13, 13' | 17.5 | 1.91, s | 3, 3', 4, 4' |
| 6-NH, 6'-NH | - | 5.01, s | 5a, 5a', 10a, 10a', 10b, 10b', 11a, 11a' |
| 11-OH, 11'-OH | - | 5.76, s | 10a, 10a', 10b, 10b' |

| Position | $\delta_H$, mult (*J* in Hz) | HMBC ($^1H \rightarrow {}^{13}C$) |
|---|---|---|
| 1, 1′ | - | |
| 3, 3′ | - | |
| 4, 4′ | - | |
| 5a, 5a′ | 5.66, s | 10a, 10a′, 10b, 10b′, 11, 11′, 11a, 11a′ |
| 6a, 6a′ | - | |
| 7, 7′ | 6.59, dd (8.6, 4.4) | 9, 9′ |
| 8, 8′ | 6.88, td (8.6, 2.6) | 6a, 6a′ |
| 9, 9′ | - | |
| 10, 10′ | 7.60, dd (9.4, 2.6) | 6a, 6a′ |
| 10a, 10a′ | - | |
| 10b, 10b′ | - | |
| 11, 11′ | 5.15, s | 6a, 6a′, 10a, 10a′, 10b, 10b′, 11a, 11a′ |
| 11a, 11a′ | - | |
| 12, 12′ | 3.04, s | 1, 1′, 3, 3′ |
| 13, 13′ | 2.19, m, 2.39, m | 3, 3′, 4, 4′, 14, 14′ |
| 14, 14′ | 1.26, t (7.1) | 3, 3′, 13, 13′ |
| 6-NH, 6′-NH | 5.66, s | 5a, 5a′, 10a, 10a′, 10b, 10b′, 11a, 11a′ |
| 11-OH, 11′-OH | 5.07, s | 10a, 10a′, 10b, 10b′ |

| Position | $\delta_H$, mult (*J* in Hz) | HMBC($^1H \rightarrow ^{13}C$) | Position | $\delta_H$, mult (*J* in Hz) | HMBC($^1H \rightarrow ^{13}C$) |
|---|---|---|---|---|---|
| 1 | - | | 1' | - | |
| 3 | - | | 3' | - | |
| 4 | - | | 4' | - | |
| 5a | 5.66, s | 4, 10a, 10b, 11, 11a | 5a' | 5.66, s | 4', 10a', 10b', 11', 11a' |
| 6a | - | | 6a' | - | |
| 7 | 6.59, m (8.8, 4.4) | 9, 10a | 7' | 6.59, m (8.8, 4.4) | 9', 10a' |
| 8 | 6.86[a], td (8.8, 2.8) | 6a, 9 | 8' | 6.88[a], td (8.8, 2.8) | 6a', 9' |
| 9 | - | | 9' | - | |
| 10 | 7.61[b], m (9.4, 2.8) | 6a, 9 | 10' | 7.63[b], m (9.4, 2.8) | 6a', 9' |
| 10a | - | | 10a' | - | |
| 10b | - | | 10b' | - | |
| 11 | 5.14[c], s | 6a, 10a, 10b, 11a | 11' | 5.15[c], s | 6a', 10a', 10b', 11a' |
| 11a | - | | 11a' | - | |
| 12 | 3.03[d], s | 1, 3 | 12' | 3.04[d], s | 1', 3' |
| 13 | 2.19, m, 2.39, m | 3, 4, 14 | 13' | 1.91, s | 3', 4' |
| 14 | 1.26, t (7.0) | 3, 13 | | | |
| 6-NH | 5.05[e], s, | 10a, 10b | 6'-NH | 5.07[e], s | 10a', 10b' |
| 11-OH | 5.66[f], s | 5a, 10b, 11a | 11'-OH | 5.77[f], s | 5a', 10b', 11a' |

[a-f] The assignments may be interchangeable.

*Verticillin H*

11

*Verticillin H*

12: R= propyl, 44%
13: R= cyclopropane, 82%
14: R= *t*-butyl, 86%
15: R= $-CH_2CH_2COOH$, 57%

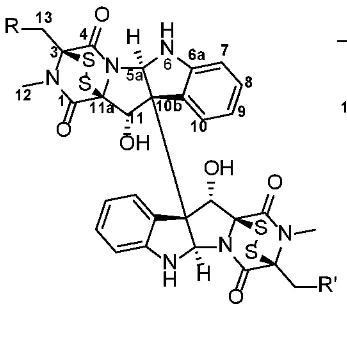
R=R'=H Verticillin A
R=R'=Me Verticillin H
R=Me, R'=H Sch 52901
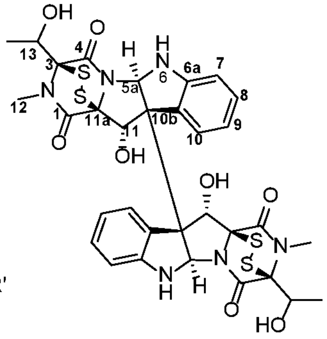
Verticillin D
FIG. 20

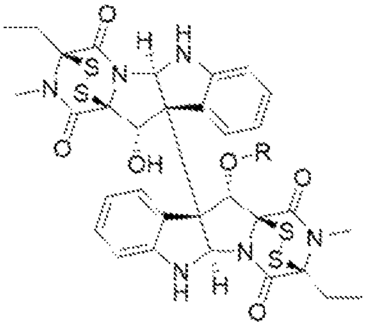
*Verticillin H*
(1; R = H)
*R* =
11
12
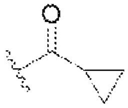
13
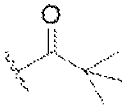
14
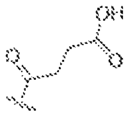
15
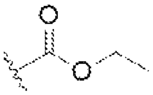
16
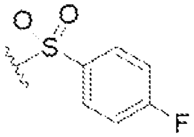
17
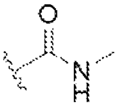
18
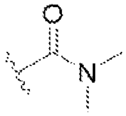
19
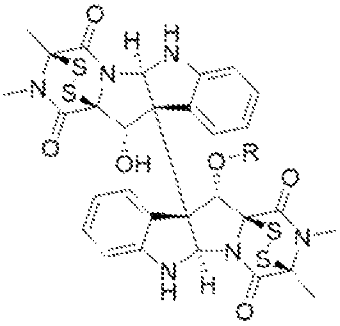
*Verticillin A*
(3; R = H)
*R* =
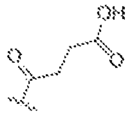
20
FIG. 22

| Compound | IC50(nM) | | | Mean Solubility (μg/mL) |
|---|---|---|---|---|
| | MDA-MB-231 | OVCAR 3 | MDA-MB-435 | |
| Verticillin H (1) | 31 | 229 | 44 | 0.065 |
| Verticillin A (3) | 23 | 36 | 18 | 0.050 |
| 11 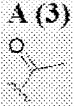 | 21 | 96 | 41 | 0.230 |
| 15 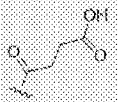 | 13 | 133 | 21 | |
| 12 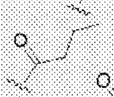 | - | - | - | |
| 13 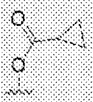 | 12 | 105 | 24 | |
| 14 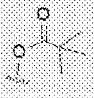 | 20 | 72 | 21 | |
| 16 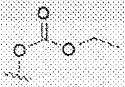 | 7 | 137 | 11 | 1.723 |
| 17  | 49 | 79 | 31 | |
| 18 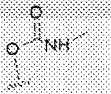 | 21 | 68 | 22 | |
| 19 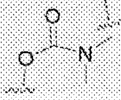 | 12 | 19 | 9 | 0.277 |
| 20 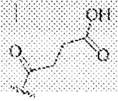 | 12 | 33 | 9 | 0.040 |
| Taxol (control) | 0.6 | 171 | 1.4 | |
MDA-MB-435: Human melanoma cancer cells, OVCAR3: Human ovarian cancer cells, MDA-MB-231: Human breast cancer cells.
FIG. 23

SEMI-SYNTHETIC ANALOGUES OF EPIPOLYTHIODIOXOPIPERAZINE ALKALOIDS

CROSS-REFERENCE TO RELATED APPLICATIONS

This application is a national stage application filed under 35 U.S.C. § 371 of PCT/US20/34268 filed May 22, 2020, which claims the benefit of priority to U.S. Provisional Application No. 62/851,939 filed May 23, 2019, the disclosure of which are incorporated herein by reference in their entireties its entirety.

STATEMENT REGARDING FEDERALLY SPONSORED RESEARCH OR DEVELOPMENT

This invention was made with government support under Grant No. P01 CA125066 awarded by the National Institutes of Health. The government has certain rights in the invention.

FIELD

The present disclosure relates to epipolythiodioxopiperazine alkaloid compounds and methods of use thereof.

BACKGROUND

In 2019, it is estimated that over 1.7 million cases of cancer will be diagnosed in the United States alone. Moreover, cancer is predicted to result in over 600,000 deaths, making it the second leading cause of death in the country (Yamazaki, T., et al., John Wiley & Sons: Wiltshire Great Britain, 2009; p 3 ("Yamazaki, et al."); O'Hagan, D., et al., *Chem. Rev.* 2015, 115, 634). Despite significant advances in both the detection and treatment of the disease made over the course of the last four decades, some types of cancer, such as triple negative breast cancer and ovarian cancer, are still extremely difficult to treat effectively (Boland, E. W., *Ann. N. Y Acad. Sci.* 1959, 82, 887). With this in mind, there is still a need for new drug discovery and development efforts to tackle this problem.

The verticillins, fungal metabolites and key members of the epipolythiodioxopiperazine alkaloids (ETP) (Iwasa, E., et al., *Isr. J. Chem.* 2011, 51 (3-4), 420-433; Zewdu, A., et al., *Clinical & experimental pharmacology* 2016, 6 (6), 221-234; and Jordan, T. W., et al., *Trends Pharmacol Sci* 1987, 8 (4), 144-149) isolated from cultures of the *Verticillium* sp., *Penicillium* sp., and *Gliocladium* sp (Gardiner, D. M., et al., *Microbiology* 2005, 151 (4), 1021-1032). These intricate natural compounds are characterized by their dimeric pyrroloindoline cores, cis-fused five membered rings, and the sulfur bridges across their diketopiperizine rings (Liu, F., et al.; *Acta Crystallogr E* 2006, 62 (3), 974-976). Verticillin A, the parent compound and arguably the most widely studied of the class, was first isolated in 1970. Although this compound has shown very promising in vitro and in vivo activity against a variety of cancer cell lines, the relatively low availability of the compound through culture from natural sources has hampered its development. Over the past decade, however, interest in verticillin A and related compounds has increased dramatically both from a biological and chemical perspective. In fact, the creative efforts of Movassaghi and others have recently established elegant total syntheses of (+)-11,11'-dideoxyverticillin A and a number of related compounds including (+)-gliocladin C, (+)-chaetocin, and bionectin. These syntheses, however, are clearly not trivial and, despite their efforts, the production of the quantities of material necessary for thorough biological evaluation via synthetic means remains a significant challenge. Adding to this challenge is the potential need for subsequent structural modification and optimization to explore structure-activity relationships and overcome limitations associated with their drug properties, particularly their poor solubility, potentially increasing the complexity of these efforts.

For example, the introduction of even a single fluorine often enhances pharmacological properties, (Yamazaki, et al.; Gillis, E. P., et al., *J. Med. Chem.* 2015, 58, 8315) such as potency, pKa, membrane permeability, metabolism, and pharmacokinetics (Purser, S., et al., *Chem. Soc. Rev.* 2008, 37, 320; Müller, K., et al., *Science* 2007, 317, 1881; and Meanwell, N. A., *J. Med. Chem.* 2018, 61, 5822). Despite the advantages of fluorination, its incorporation in natural product derived drug leads is challenging (Kirk, K. L., *Org. Process Res. Dev.* 2008, 12, 305). Several strategies have been developed toward synthetic and semisynthetic methods for selective fluorination (Romanov-Michailidis, F., et al., *Angew. Chem.* 2013, 125, 9436; and Halperin, S. D., et al., *Org. Lett.* 2015, 17, 5200). However, this remains difficult in structurally complex natural products, which can be sensitive to degradation (Walker, M. C., et al., *Chem. Soc. Rev.* 2014, 43, 6527).

SUMMARY

Disclosed herein is a series of synthetic analogues of the verticillin class of natural products, which are epipolythiodioxopiperazine alkaloids. The verticillins (e.g., verticillin A) are fungal metabolites that were originally isolated/discovered in the 1970s and have been well studied for their potential anticancer activities. Verticillin H was first reported by Oberlies and Pearce in 2012. These compounds show high potency against a variety of tumor cell types, with IC50 values typically in the 10-500 nM range. In addition, a number of in vivo studies have been carried out, primarily with verticillin A. Although highly promising, the utility of these compounds has been hampered by a few problems. One of the major problems with these compounds is the poor solubility and overall poor drug properties of the verticillins for administration of these drugs to treat cancer. Another is the relatively low abundance of these compounds, making it difficult to carry out thorough studies with these compounds. The supply problem has been addressed to some degree, making it possible to obtain reasonable quantities of these materials. With these quantities in hand, semi-synthetic modification of the compounds becomes feasible in an effort to modify their structures to improve drug properties.

Two basic strategies have been employed for the modification of these compounds. The first is a feeding experiment employing a fluorinated tryptophan precursor in which precursor-directed biosynthesis is used to generate a series of fluorinated derivatives. The resulting compounds, including both the 9-fluoro and 9,9'-difluoro derivatives, stability is improved by altering the electron density of the electron-rich aromatic rings of the compounds, thereby limiting potential aromatic hydroxylation reactions. This can increase the half-life of the compounds for administration. Importantly, the mono-fluorinated derivatives appear to maintain similar potency as the parent compounds.

The second approach is based upon taking the natural compounds, verticillin H or verticillin A, and modifying the alcohol attached at the C11 position. This is accomplished through treatment with a variety of electrophiles to form esters, carbonates, carbamates, and sulfonates. In all cases, only a single group can be introduced onto the verticillin despite the fact that the structure is dimeric. The nature of the group introduced may have a profound effect upon the drug properties of the molecules. For example, introduction of a succinate moiety greatly increases water solubility of the molecule. Initially, only cleavable groups were introduced at this position, which can facilitate administration of the drug, but would then be cleaved metabolically to reveal the "active" drug molecule. In vitro testing, however, indicates that the conjugates retain essentially the same potency as the parent molecule. With this in mind, more robust acyl substituents, including the carbonate and the carbamates, have been introduced. These groups can have longer half-lives than their ester counterparts and, therefore, are able to be used to tune the properties of the molecules for successful in vivo administration. All of these alcohol modifications can also be coupled with the fluorinated analogues to generate molecules with multiple points of differentiation from the parent compounds. These novel compounds are useful for the treatment of cancer.

The details of one or more embodiments of the disclosure are set forth in the accompanying drawings and the description below. Other features, objects, and advantages of the disclosure will be apparent from the description and drawings, and from the claims.

BRIEF DESCRIPTION OF DRAWINGS

FIG. 1 is a figure showing the structures of verticillins (1-3) and the fluorinated analogues (4-10) obtained via precursor-directed biosynthesis FIG. 2 is a table showing the $^{1}$H-NMR data for 4-10 in $CDCl_3$ [700 MHz for 4-8 and 500 MHz for 9-10].

FIG. 3 is a table showing the $^{13}$C NMR data for 4-8 in $CDCl_3$ [175 MHz].

FIG. 4 is a table showing the Cytotoxicity of 1-10.

FIG. 9 is a table showing the $^{1}$H, $^{13}$C and HMBC NMR data for 9-F-verticillin H (4) in $CDCl_3$ [700 MHz for $^{1}$H and 175 MHz for $^{13}$C].

FIG. 20 is a figure showing the structures of different verticillin symmetrical and asymmetrical analogues.

FIG. 22 is a table showing the structures of compounds 1, 3, and 11-20.

FIG. 23 is a table showing the cytotoxicity and mean solubility of compounds 1, 3, and 11-20.

Like reference symbols in the various drawings indicate like elements.

DETAILED DESCRIPTION

Figure 5:
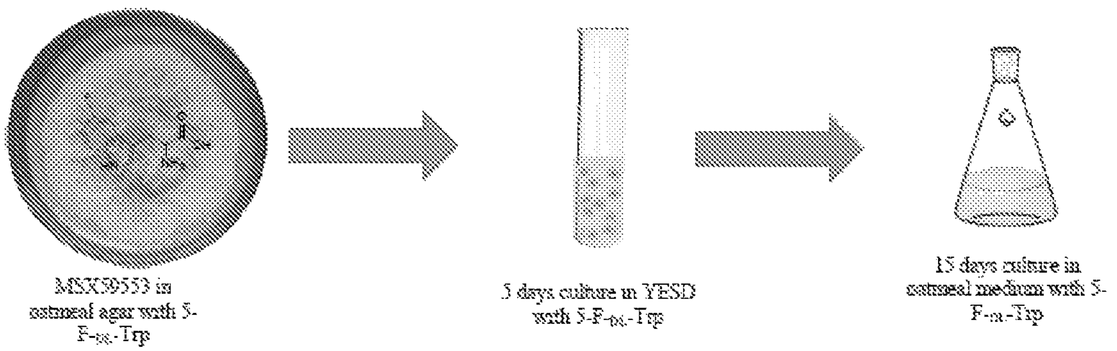
FIG. 5 is a diagram showing the culture conditions for MSX59553 grown on oatmeal agar medium supplemented with a racemic mixture of 5-F-DL-Trp. The plate was used to inoculate 10 mL of YESD to be used to grow cultures on oatmeal supplemented with 375 ppm of 5-F-DL-Trp.
Figure 6:
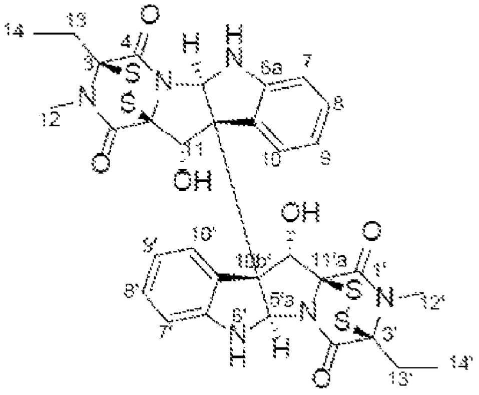
FIG. 6 is a table showing the $^{1}$H and $^{13}$C NMR data for verticillin H (1) in $CDCl_3$ [500 MHz for $^{1}$H and 125 MHz for $^{13}$C].
Figure 7:
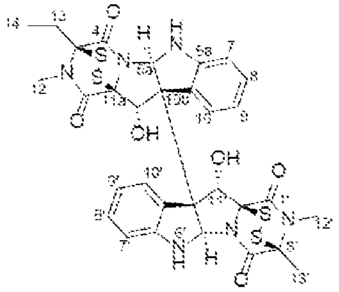
FIG. 7 is a table showing the $^{1}$H and $^{13}$C NMR data for Sch 52901 (2) in $CDCl_3$ [500 MHz for 1H and 125 MHz for $^{13}$C].
Figure 8:
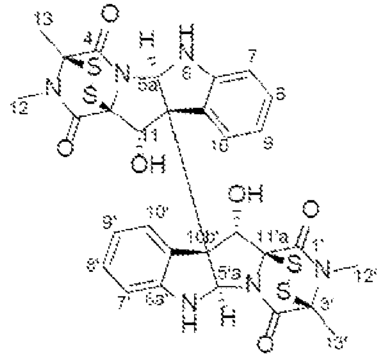
FIG. 8 is a table showing the $^{1}$H and $^{13}$C NMR data for verticillin A (3) in $CDCl_3$ [500 MHz for $^{1}$H and 125 MHz for $^{13}$C].

Reference will now be made in detail to the embodiments of the invention, examples of which are illustrated in the drawings and the examples. This invention may, however, be embodied in many different forms and should not be construed as limited to the embodiments set forth herein.

General Definitions

Unless defined otherwise, all technical and scientific terms used herein have the same meaning as commonly understood to one of ordinary skill in the art to which this disclosure belongs.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

The term "comprising" and variations thereof as used herein is used synonymously with the term "including" and variations thereof and are open, non-limiting terms. Although the terms “comprising” and “including” have been used herein to describe various embodiments, the terms “consisting essentially of” and “consisting of” can be used in place of “comprising” and “including” to provide for more specific embodiments and are also disclosed. Throughout the description and claims of this specification the word “comprise” and other forms of the word, such as “comprising” and “comprises,” means including but not limited to, and is not intended to exclude, for example, other additives, components, integers, or steps.

As used in the specification and claims, the singular form “a”, “an”, and “the” include plural references unless the context clearly dictates otherwise. For example, the term “an agent” includes a plurality of agents, including mixtures thereof.

As used herein, the terms “may,” “optionally,” and “may optionally” are used interchangeably and are meant to include cases in which the condition occurs as well as cases in which the condition does not occur. Thus, for example, the statement that a formulation “may include an excipient” is meant to include cases in which the formulation includes an excipient as well as cases in which the formulation does not include an excipient.

“Administration” to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. “Concurrent administration”, “administration in combination”, “simultaneous administration” or “administered simultaneously” as used herein, means that the compounds are administered at the same point in time or essentially immediately following one another. In the latter case, the two compounds are administered at times sufficiently close that the results observed are indistinguishable from those achieved when the compounds are administered at the same point in time. “Systemic administration” refers to the introducing or delivering to a subject an agent via a route which introduces or delivers the agent to extensive areas of the subject’s body (e.g. greater than 50% of the body), for example through entrance into the circulatory or lymph systems. By contrast, “local administration” refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject’s body. Administration includes self-administration and the administration by another.

As used here, the terms “beneficial agent” and “active agent” are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms “beneficial agent” or “active agent” are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

A “decrease” can refer to any change that results in a smaller amount of a symptom, disease, composition, condition, or activity. A substance is also understood to decrease the genetic output of a gene when the genetic output of the gene product with the substance is less relative to the output of the gene product without the substance. Also, for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

“Inhibit,” “inhibiting,” and “inhibition” mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By “reduce” or other forms of the word, such as “reducing” or “reduction,” is meant lowering of an event or characteristic (e.g., tumor growth). It is understood that this is typically in relation to some standard or expected value, in other words it is relative, but that it is not always necessary for the standard or relative value to be referred to. For example, “reduces tumor growth” means reducing the rate of growth of a tumor relative to a standard or a control.

As used herein, the terms “treating” or “treatment” of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms “treating” and “treatment” can also refer to reduction in severity and/or frequency of symptoms, elimination of symptoms and/or underlying cause, prevention of the occurrence of symptoms and/or their underlying cause, and improvement or remediation of damage.

By “prevent” or other forms of the word, such as “preventing” or “prevention,” is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed. For example, the terms “prevent” or “suppress” can refer to a treatment that forestalls or slows the onset of a disease or condition or reduced the severity of the disease or condition. Thus, if a treatment can treat a disease in a subject having symptoms of the disease, it can also prevent or suppress that disease in a subject who has yet to suffer some or all of the symptoms. As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount". However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject. The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like, or using a different acid that produces the same counterion. Lists of additional suitable salts may be found, e.g., in Remington's Pharmaceutical Sciences, 17th ed., Mack Publishing Company, Easton, Pa., p. 1418 (1985).

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

A "control" is an alternative subject or sample used in an experiment for comparison purposes. A control can be "positive" or "negative."

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human. Thus, the subject can be a human or veterinary patient. The term "patient"

refers to a subject under the treatment of a clinician, e.g., physician. Administration of the therapeutic agents can be carried out at dosages and for periods of time effective for treatment of a subject. In some embodiments, the subject is a human.

Chemical Definitions

Terms used herein will have their customary meaning in the art unless specified otherwise. The organic moieties mentioned when defining variable positions within the general formulae described herein (e.g., the term "halogen") are collective terms for the individual substituents encompassed by the organic moiety. The prefix Cn-Cm preceding a group or moiety indicates, in each case, the possible number of carbon atoms in the group or moiety that follows.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, heteroatoms present in a compound or moiety, such as nitrogen, can have hydrogen substituents and/or any permissible substituents of organic compounds described herein which satisfy the valency of the heteroatom. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound (e.g., a compound that does not spontaneously undergo transformation such as by rearrangement, cyclization, elimination, etc.

The term "optionally substituted," as used herein, means that substitution with an additional group is optional and therefore it is possible for the designated atom to be unsubstituted. Thus, by use of the term "optionally substituted" the disclosure includes examples where the group is substituted and examples where it is not.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

As used herein, the term "alkyl" refers to saturated, straight-chained or branched saturated hydrocarbon moieties. Unless otherwise specified, $C_1$-$C_{24}$ (e.g., $C_1$-$C_{22}$, $C_1$-$C_{20}$, $C_1$-$C_{18}$, $C_1$-$C_{16}$, $C_1$-$C_{14}$, $C_1$-$C_{12}$, $C_1$-$C_{10}$, $C_1$-$C_8$, $C_1$-$C_6$, or $C_1$-$C_4$) alkyl groups are intended. Examples of alkyl groups include methyl, ethyl, propyl, 1-methyl-ethyl, butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, and 1-ethyl-2-methyl-propyl. Alkyl substituents may be unsubstituted or substituted with one or more chemical moieties. The alkyl group can be substituted with one or more groups including, but not limited to, hydroxy, halogen, acyl, alkyl, alkoxy, alkenyl, alkynyl, aryl, heteroaryl, acyl, aldehyde, amino, carboxylic acid, ester, ether, ketone, nitro, silyl, sulfo-oxo, sulfonyl, sulfone, sulfoxide, thiosulfonate (e.g., —$SO_2$Ra), or thiol, as described below, provided that the substituents are sterically compatible and the rules of chemical bonding and strain energy are satisfied. The alkyl group can also include one or more heteroatoms (e.g., from one to three heteroatoms) incorporated within the hydrocarbon moiety. Examples of heteroatoms include, but are not limited to, nitrogen, oxygen, sulfur, and phosphorus.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" specifically refers to an alkyl group that is substituted with one or more halides (halogens; e.g., fluorine, chlorine, bromine, or iodine). The term "alkoxyalkyl" specifically refers to an alkyl group that is substituted with one or more alkoxy groups, as described below. The term "alkylamino" specifically refers to an alkyl group that is substituted with one or more amino groups, as described below, and the like. The term "alkylthiol" specifically refers to an alkyl group that is substituted with one or more thiol groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

As used herein, the term "alkenyl" refers to unsaturated, straight-chained, or branched hydrocarbon moieties containing a double bond. Unless otherwise specified, $C_2$-$C_{24}$ (e.g., $C_2$-$C_{22}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, $C_2$-$C_4$) alkenyl groups are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. The term "vinyl" refers to a group having the structure —CH═$CH_2$; 1-propenyl refers to a group with the structure-CH═CH—$CH_3$; and 2-propenyl refers to a group with the structure —$CH_2$—CH═$CH_2$. Asymmetric structures such as $(Z^1Z^2)C{=}C(Z^3Z^4)$ are intended to include both the E and Z isomers. This can be presumed in structural formulae herein wherein an asymmetric alkene is present, or it can be explicitly indicated by the bond symbol C═C. Alkenyl substituents may be unsubstituted or substituted with one or more chemical moieties. Examples of suitable substituents include, for example, alkyl, halogenated alkyl, alkoxy, alkenyl, alkynyl, aryl, heteroaryl, acyl, aldehyde, amino, carboxylic acid, ester, ether, halide, hydroxy, ketone, nitro, silyl, sulfo-oxo, sulfonyl, sulfone, sulfoxide, thiosulfonate (e.g., —$SSO_2$Ra), or thiol, as described below, provided that the substituents are sterically compatible and the rules of chemical bonding and strain energy are satisfied.

As used herein, the term "alkynyl" represents straight-chained or branched hydrocarbon moieties containing a triple bond. Unless otherwise specified, $C_2$-$C_{24}$ (e.g., $C_2$-$C_{22}$, $C_2$-$C_{20}$, $C_2$-$C_{18}$, $C_2$-$C_{16}$, $C_2$-$C_{14}$, $C_2$-$C_{12}$, $C_2$-$C_{10}$, $C_2$-$C_8$, $C_2$-$C_6$, $C_2$-$C_4$) alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl. Alkynyl substituents may be unsubstituted or substituted with one or more chemical moieties. Examples of suitable substituents include, for example, alkyl, halogenated alkyl, alkoxy, alkenyl, alkynyl, aryl, heteroaryl, acyl, aldehyde, amino, carboxylic acid, ester, ether, halide, hydroxy, ketone, nitro, silyl, sulfo-oxo, sulfonyl, sulfone, sulfoxide, thiosulfonate (e.g., —$SSO_2$Ra), or thiol, as described below.

As used herein, the term "aryl," as well as derivative terms such as aryloxy, refers to groups that include a monovalent aromatic carbocyclic group of from 3 to 20 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphthyl, phenylcyclopropyl, and indanyl. In some embodiments, the aryl group can be a phenyl, indanyl or naphthyl group. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl substituents may be unsubstituted or substituted with one or more chemical moieties. Examples of suitable substituents include, for example, alkyl, halogenated alkyl, alkoxy, alkenyl, alkynyl, aryl, heteroaryl, acyl, aldehyde, amino, carboxylic acid, cycloalkyl, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, acyl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, acyl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "acyl" as used herein is represented by the formula —$C(O)Z^1$ where $Z^1$ can be a hydrogen, hydroxyl, alkoxy, alkyl, halogenated alkyl, alkenyl, alkynyl, aryl, heteroaryl, cycloalkyl, cycloalkenyl, heterocycloalkyl, or heterocycloalkenyl group described above. As used herein, the term "acyl" can be used interchangeably with "carbonyl." Throughout this specification "C(O)" or "CO" is a short hand notation for C═O.

As used herein, the term "alkoxy" refers to a group of the formula $Z^1$—O—, where $Z^1$ is unsubstituted or substituted alkyl as defined above. Unless otherwise specified, alkoxy groups wherein $Z^1$ is a $C_1$-$C_{24}$ (e.g., $C_1$-$C_{22}$, $C_1$-$C_{20}$, $C_1$-$C_{18}$, $C_1$-$C_{16}$, $C_1$-$C_{14}$, $C_1$-$C_{12}$, $C_1$-$C_{10}$, $C_1$-$C_8$, $C_1$-$C_6$, $C_1$-$C_4$) alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-penoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

The term "aldehyde" as used herein is represented by the formula C(O)H.

The terms "amine" or "amino" as used herein are represented by the formula $NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above. "Amido" is —$C(O)NZ^1Z^2$.

The term "carboxylic acid" as used herein is represented by the formula —C(O)OH. A "carboxylate" or "carboxyl" group as used herein is represented by the formula —$C(O)O^-$.

The term "ester" as used herein is represented by the formula —$OC(O)Z^1$ or —$C(O)OZ^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" or "halo" as used herein refers to fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —$SiZ^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —$S(O)_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH$—.

The term "thiol" as used herein is represented by the formula —SH.

The term "thio" as used herein is represented by the formula —S—.

As used herein, Me refers to a methyl group; OMe refers to a methoxy group; and i-Pr refers to an isopropyl group.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

The term "substituted" refers to a molecule wherein at least one hydrogen atom is replaced with a substituent. When substituted, one or more of the groups are "substituents." The molecule can be multiply substituted. In the case of an oxo substituent ("═O"), two hydrogen atoms are replaced. Example substituents within this context can include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(═O)Rb, —NRaC(═O)NRaNRb, —NRaC(═O)ORb, —NRaSO$_2$Rb, —C(═O)Ra, —C(═O)ORa, —C(═O)NRaRb, —OC(═O)NRaRb, —ORa, —SRa, —SORa, —S(═O)$_2$Ra, —OS(═O)$_2$Ra and —S(═O)$_2$ORa. Ra and Rb in this context can be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

Unless stated to the contrary, a formula with chemical bonds shown only as solid lines and not as wedges or dashed lines contemplates each possible stereoisomer or mixture of stereoisomer (e.g., each enantiomer, each diastereomer, each meso compound, a racemic mixture, or scalemic mixture).

Reference will now be made in detail to specific aspects of the disclosed materials, compounds, compositions, articles, and methods, examples of which are illustrated in the accompanying Examples and Figures.

Compounds

Disclosed herein is a series of synthetic analogues of the verticillin class of natural products, which are epipolythiodioxopiperazine alkaloids.

In some aspects, disclosed herein is a compound represented by a structure having Formula I:

Formula I

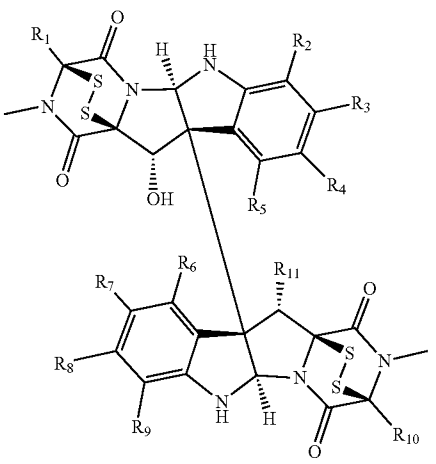

wherein $R_1$ and $R_{10}$ are independently substituted or unsubstituted alkyl;

$R_4$ and $R_7$ are both halogen or hydrogen; $R_4$ is hydrogen and $R_7$ is halogen; or $R_4$ is halogen and $R_7$ is hydrogen;

$R_2$, $R_3$, $R_5$, $R_6$, $R_8$, and $R_9$ are independently hydrogen; halogen; amino; hydroxy; thiol; ester; carbamate; carbonate; sulfonate; substituted or unsubstituted alkyl, alkenyl, alkynyl, or alkoxy; and $R_{11}$ is a hydroxy, ester, carbamate, carbonate, or sulfonate;

wherein when $R_{11}$ is a hydroxy, then $R_4$ and $R_7$ are both halogen, $R_4$ is hydrogen and $R_7$ is halogen, or $R_4$ is halogen and $R_7$ is hydrogen;

or a pharmaceutically acceptable salt thereof.

In some embodiments, $R_1$ and $R_{10}$ are independently substituted or unsubstituted alkyl. In some embodiments, $R_1$ and $R_{10}$ can be independently methyl, ethyl, propyl, butyl, or a combination thereof. In some embodiments, $R_1$ and $R_{10}$ can be independently methyl, ethyl, or a combination thereof. In some embodiments, $R_1$ and $R_{10}$ are both methyl or ethyl, $R_1$ is methyl and $R_{10}$ is ethyl, or $R_1$ is ethyl and $R_{10}$ is methyl.

In some embodiments, $R_4$ and $R_7$ are both halogen or hydrogen; $R_4$ is hydrogen and $R_7$ is halogen; or $R_4$ is halogen and $R_7$ is hydrogen. In some embodiments, $R_4$ and $R_7$ can be independently hydrogen, chlorine, fluorine, bromine, iodine, or a combination thereof. In some embodiments, $R_4$ and $R_7$ are both fluorine, $R_4$ is hydrogen and $R_7$ is fluorine, or $R_4$ is fluorine and $R_7$ is hydrogen.

In some embodiments, Ru is a hydroxy, ester, carbamate, carbonate, or sulfonate wherein when $R_{11}$ is a hydroxy, then $R_4$ and $R_7$ are both halogen, $R_4$ is hydrogen and $R_7$ is halogen, or $R_4$ is halogen and $R_7$ is hydrogen.

In some embodiments, $R_{11}$ is a carbamate or an ester. In some embodiments, when $R_{11}$ is a hydroxy, then $R_4$ and $R_7$ are both halogen, $R_4$ is hydrogen and $R_7$ is halogen, or $R_4$ is halogen and $R_7$ is hydrogen. In some embodiments, $R_{11}$ is an ester. In some embodiments, $R_{11}$ is a carbamate. In some embodiments, $R_{11}$ is a carbonate. In some embodiments, $R_{11}$ is a sulfonate.

In some embodiments, the Ru can be selected from one of the following:

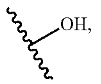 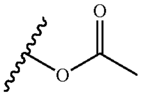, 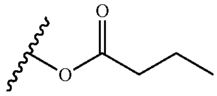,

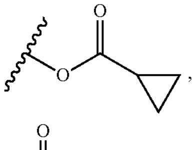, 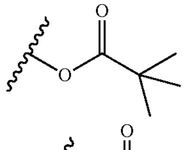,

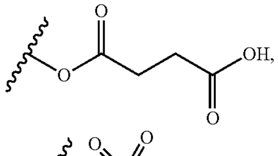 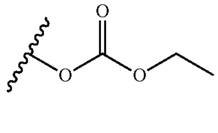,

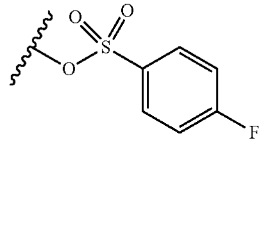, 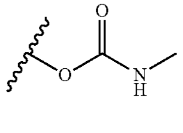,

-continued

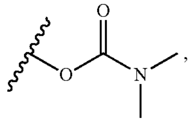, 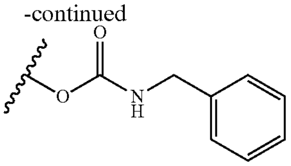, and

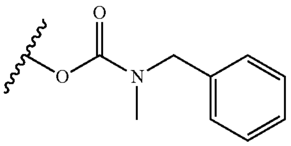.

In some embodiments, $R_2$, $R_3$, $R_5$, $R_6$, $R_8$, and $R_9$ are independently hydrogen; halogen; amino; hydroxy; thiol; ester; carbamate; carbonate; sulfonate; substituted or unsubstituted alkyl, alkenyl, alkynyl, or alkoxy. In some embodiments, $R_2$, $R_3$, $R_5$, $R_6$, $R_8$, and $R_9$ are hydrogen.

In some embodiments, $R_1$ and $R_{10}$ are both methyl or ethyl, $R_1$ is methyl and $R_{10}$ is ethyl, or $R_1$ is ethyl; $R_{10}$ is methyl; $R_{11}$ is an ester, carbamate, carbonate, or sulfonate; and $R_2$-$R_9$ are hydrogen.

In some embodiments, $R_1$ and $R_{10}$ are both methyl or ethyl, $R_1$ is methyl and $R_{10}$ is ethyl, or $R_1$ is ethyl and $R_{10}$ is methyl; $R_{11}$ is an ester, carbamate, carbonate, or sulfonate; $R_2$, $R_3$, $R_5$, $R_6$, $R_8$, $R_9$ are hydrogen; and $R_4$ and $R_7$ are both a halogen, $R_4$ is hydrogen and $R_7$ is a halogen, or $R_4$ is a halogen and $R_7$ is hydrogen.

In some embodiments, $R_1$ and $R_{10}$ are both methyl or ethyl, $R_1$ is methyl and $R_{10}$ is ethyl, or $R_1$ is ethyl and $R_{10}$ is methyl; $R_{11}$ is a carbamate; and $R_2$-$R_9$ are hydrogen. In some embodiments, $R_1$ and $R_{10}$ are both methyl or ethyl, $R_1$ is methyl and $R_{10}$ is ethyl, or $R_1$ is ethyl and $R_{10}$ is methyl; $R_{11}$ is an ester; and $R_2$-$R_9$ are hydrogen.

In some embodiments, $R_1$ and $R_{10}$ are both methyl or ethyl, $R_1$ is methyl and $R_{10}$ is ethyl, or $R_1$ is ethyl and $R_{10}$ is methyl; $R_{11}$ is a carbamate; $R_2$, $R_3$, $R_5$, $R_6$, $R_8$, $R_9$ are hydrogen; and $R_4$ and $R_7$ are both a halogen, $R_4$ is hydrogen and $R_7$ is a halogen, or $R_4$ is a halogen and $R_7$ is hydrogen. In some embodiments, $R_1$ and $R_{10}$ are both methyl or ethyl, $R_1$ is methyl and $R_{10}$ is ethyl, or $R_1$ is ethyl and $R_{10}$ is methyl; Ru is an ester; $R_2$, $R_3$, $R_5$, $R_6$, $R_8$, $R_9$ are hydrogen; and $R_4$ and $R_7$ are both a halogen, $R_4$ is hydrogen and $R_7$ is a halogen, or $R_4$ is a halogen and $R_7$ is hydrogen.

In some other aspects, disclosed herein is a compound represented by a structure having Formula II:

Formula II

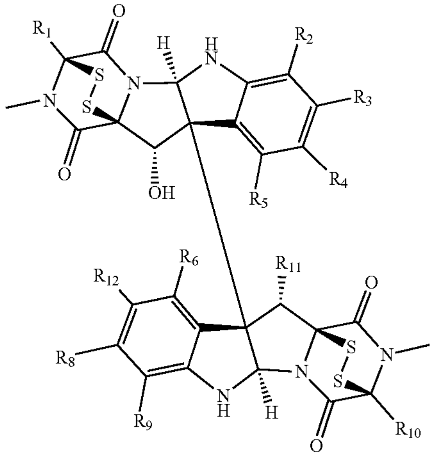

wherein $R_1$ and $R_{10}$ are independently substituted or unsubstituted alkyl;

$R_{12}$ and $R_{13}$ are both halogen; $R_{12}$ is hydrogen and $R_{13}$ is halogen; or $R_{12}$ is halogen and $R_{13}$ is hydrogen;

$R_2$, $R_3$, $R_5$, $R_6$, $R_8$, and $R_9$ are independently hydrogen; halogen; amino; hydroxy; thiol; ester; carbamate; carbonate; sulfonate; substituted or unsubstituted alkyl, alkenyl, alkynyl, or alkoxy; and $R_{11}$ is a hydroxy, ester, carbamate, carbonate, or sulfonate;

or a pharmaceutically acceptable salt thereof.

In some embodiments, $R_1$ and $R_{10}$ are independently substituted or unsubstituted alkyl. In some embodiments, $R_1$ and $R_{10}$ can be independently methyl, ethyl, propyl, butyl, or a combination thereof. In some embodiments, $R_1$ and $R_{10}$ can be independently methyl, ethyl, or a combination thereof. In some embodiments, $R_1$ and $R_{10}$ are both methyl or ethyl, $R_1$ is methyl and $R_{10}$ is ethyl, or $R_1$ is ethyl and $R_{10}$ is methyl.

In some embodiments, $R_{12}$ and $R_{13}$ are both halogen; $R_{12}$ is hydrogen and $R_{13}$ is halogen; or $R_{12}$ is halogen and $R_{13}$ is hydrogen. In some embodiments, $R_{12}$ and $R_{13}$ can be independently hydrogen, chlorine, fluorine, bromine, iodine, or a combination thereof. In some embodiments, $R_{12}$ and $R_{13}$ are both fluorine, $R_{12}$ is hydrogen and $R_{13}$ is fluorine, or $R_{12}$ is fluorine and $R_{13}$ is hydrogen.

In some embodiments, $R_{11}$ is a hydroxy, ester, carbamate, carbonate, or sulfonate. In some embodiments, $R_{11}$ is a hydroxy, or a carbamate or an ester. In some embodiments, $R_{11}$ is a hydroxy. In some embodiments, $R_{11}$ is an ester. In some embodiments, $R_1$ is a carbamate. In some embodiments, $R_1$ is a carbonate. In some embodiments, $R_1$ is a sulfonate.

In some embodiments, the $R_1$ can be selected from one of the following:

 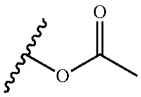, 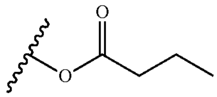,

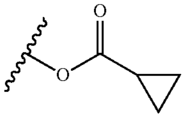, 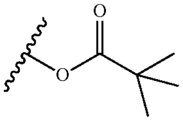,

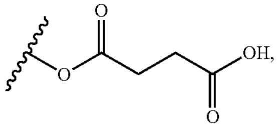 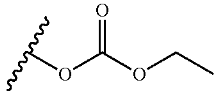,

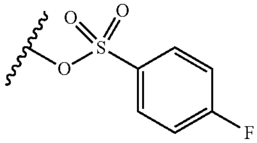, 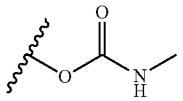,

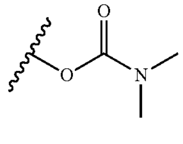, 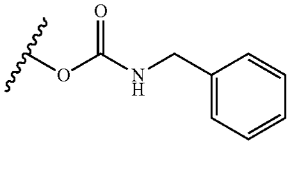, and

-continued

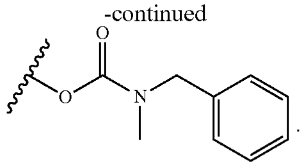.

In some embodiments, $R_2$, $R_3$, $R_5$, $R_6$, $R_8$, and $R_9$ are independently hydrogen; halogen; amino; hydroxy; thiol; ester; carbamate; carbonate; sulfonate; substituted or unsubstituted alkyl, alkenyl, alkynyl, or alkoxy. In some embodiments, $R_2$, $R_3$, $R_5$, $R_6$, $R_8$, and $R_9$ are hydrogen.

In some embodiments, $R_1$ and $R_{10}$ are both methyl or ethyl, $R_1$ is methyl and $R_{10}$ is ethyl, or $R_1$ is ethyl and $R_{10}$ is methyl; Ru is an ester, carbamate, carbonate, or sulfonate; $R_2$, $R_3$, $R_5$, $R_6$, $R_8$, $R_9$ are hydrogen; and $R_{12}$ and $R_{13}$ are both a halogen, $R_{12}$ is hydrogen and $R_{13}$ is a halogen, or $R_{12}$ is a halogen and $R_{13}$ is hydrogen.

In some embodiments, $R_1$ and $R_{10}$ are both methyl or ethyl, $R_1$ is methyl and $R_{10}$ is ethyl, or $R_1$ is ethyl and $R_{10}$ is methyl; Ru is a carbamate; $R_2$, $R_3$, $R_5$, $R_6$, $R_8$, $R_9$ are hydrogen; and $R_{12}$ and $R_{13}$ are both a halogen, $R_{12}$ is hydrogen and $R_{13}$ is a halogen, or $R_{12}$ is a halogen and $R_{13}$ is hydrogen.

In some embodiments, $R_1$ and $R_{10}$ are both methyl or ethyl, $R_1$ is methyl and $R_{10}$ is ethyl, or $R_1$ is ethyl and $R_{10}$ is methyl; $R_1$ is an ester; $R_2$, $R_3$, $R_5$, $R_6$, $R_8$, $R_9$ are hydrogen; and $R_{12}$ and $R_{13}$ are both a halogen, $R_{12}$ is hydrogen and $R_{13}$ is a halogen, or $R_{12}$ is a halogen and $R_{13}$ is hydrogen.

In some other aspects, disclosed herein is a compound represented by a structure having Formula III:

Formula III

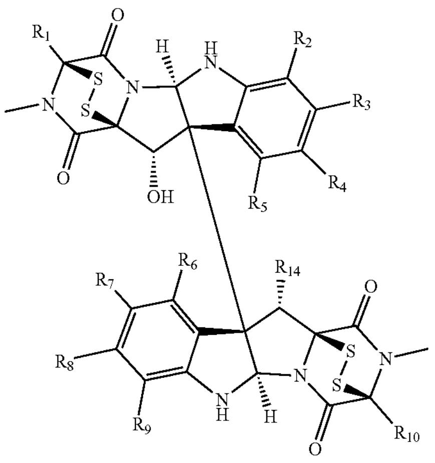

wherein $R_1$ and $R_{10}$ are independently substituted or unsubstituted alkyl;

$R_4$ and $R_7$ are both halogen or hydrogen; $R_4$ is hydrogen and $R_7$ is halogen; or $R_4$ is halogen and $R_7$ is hydrogen;

$R_2$, $R_3$, $R_5$, $R_6$, $R_8$, and $R_9$ are independently hydrogen; halogen; amino; hydroxy; thiol; ester; carbamate; carbonate; sulfonate; substituted or unsubstituted alkyl, alkenyl, alkynyl, or alkoxy; and $R_{14}$ is an ester, carbamate, carbonate, or sulfonate;

or a pharmaceutically acceptable salt thereof.

In some embodiments, $R_1$ and $R_{10}$ are independently substituted or unsubstituted alkyl. In some embodiments, $R_1$ and $R_{10}$ can be independently methyl, ethyl, propyl, butyl, or a combination thereof. In some embodiments, $R_1$ and $R_{10}$ can be independently methyl, ethyl, or a combination thereof. In some embodiments, $R_1$ and $R_{10}$ are both methyl or ethyl, $R_1$ is methyl and $R_{10}$ is ethyl, or $R_1$ is ethyl and $R_{10}$ is methyl.

In some embodiments, $R_4$ and $R_7$ are both halogen or hydrogen; $R_4$ is hydrogen and $R_7$ is halogen; or $R_4$ is halogen and $R_7$ is hydrogen. In some embodiments, $R_4$ and $R_7$ can be independently hydrogen chlorine, fluorine, bromine, iodine, or a combination thereof. In some embodiments, $R_4$ and $R_7$ are both fluorine, $R_4$ is hydrogen and $R_7$ is fluorine, or $R_4$ is fluorine and $R_7$ is hydrogen.

In some embodiments, $R_{14}$ is an ester, carbamate, carbonate, or sulfonate. In some embodiments, $R_{14}$ is a carbamate or an ester. In some embodiments, $R_{14}$ is an ester. In some embodiments, $R_{14}$ is a carbamate. In some embodiments, $R_{14}$ is a carbonate. In some embodiments, $R_{14}$ is a sulfonate.

In some embodiments, the $R_{14}$ can be selected from one of the following:

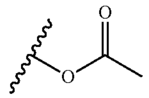, 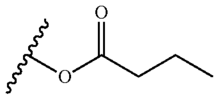,

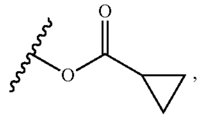, 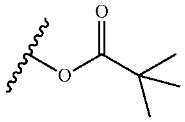,

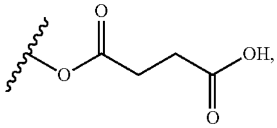, 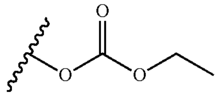,

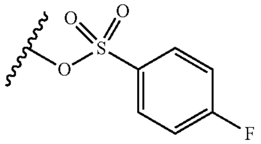, 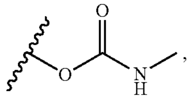,

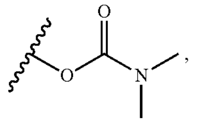, 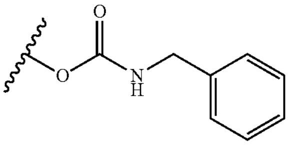, and

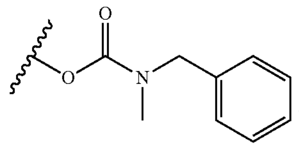.

In some embodiments, $R_2$, $R_3$, $R_5$, $R_6$, $R_8$, and $R_9$ are independently hydrogen; halogen; amino; hydroxy; thiol; ester; carbamate; carbonate; sulfonate; substituted or unsubstituted alkyl, alkenyl, alkynyl, or alkoxy. In some embodiments, $R_2$, $R_3$, $R_5$, $R_6$, $R_8$, and $R_9$ are hydrogen.

In some embodiments, $R_1$ and $R_{10}$ are both methyl or ethyl, $R_1$ is methyl and $R_{10}$ is ethyl, or $R_1$ is ethyl; $R_{10}$ is methyl; $R_{14}$ is an ester, carbamate, carbonate, or sulfonate; and $R_2$-$R_9$ are hydrogen.

In some embodiments, $R_1$ and $R_{10}$ are both methyl or ethyl, $R_1$ is methyl and $R_{10}$ is ethyl, or $R_1$ is ethyl and $R_{10}$ is methyl; $R_{14}$ is an ester, carbamate, carbonate, or sulfonate;

$R_2$, $R_3$, $R_5$, $R_6$, $R_8$, $R_9$ are hydrogen; and $R_4$ and $R_7$ are both a halogen, $R_4$ is hydrogen and $R_7$ is a halogen, or $R_4$ is a halogen and $R_7$ is hydrogen.

In some embodiments, $R_1$ and $R_{10}$ are both methyl or ethyl, $R_1$ is methyl and $R_{10}$ is ethyl, or $R_1$ is ethyl and $R_{10}$ is methyl; $R_{14}$ is a carbamate; and $R_2$-$R_9$ are hydrogen. In some embodiments, $R_1$ and $R_{10}$ are both methyl or ethyl, $R_1$ is methyl and $R_{10}$ is ethyl, or $R_1$ is ethyl and $R_{10}$ is methyl; $R_{14}$ is an ester; and $R_2$-$R_9$ are hydrogen.

In some embodiments, $R_1$ and $R_{10}$ are both methyl or ethyl, $R_1$ is methyl and $R_{10}$ is ethyl, or $R_1$ is ethyl and $R_{10}$ is methyl; $R_{14}$ is a carbamate; $R_2$, $R_3$, $R_5$, $R_6$, $R_8$, $R_9$ are hydrogen; and $R_4$ and $R_7$ are both a halogen, $R_4$ is hydrogen and $R_7$ is a halogen, or $R_4$ is a halogen and $R_7$ is hydrogen.

In some embodiments, $R_1$ and $R_{10}$ are both methyl or ethyl, $R_1$ is methyl and $R_{10}$ is ethyl, or $R_1$ is ethyl and $R_{10}$ is methyl; $R_{14}$ is an ester; $R_2$, $R^3$, $R_5$, $R_6$, $R_8$, $R_9$ are hydrogen; and $R_4$ and $R_7$ are both a halogen, $R_4$ is hydrogen and $R_7$ is a halogen, or $R_4$ is a halogen and $R_7$ is hydrogen.

Examples of these compounds are shown below:

4

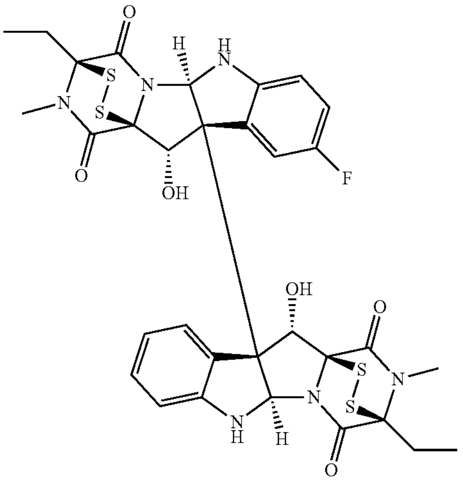

,

5

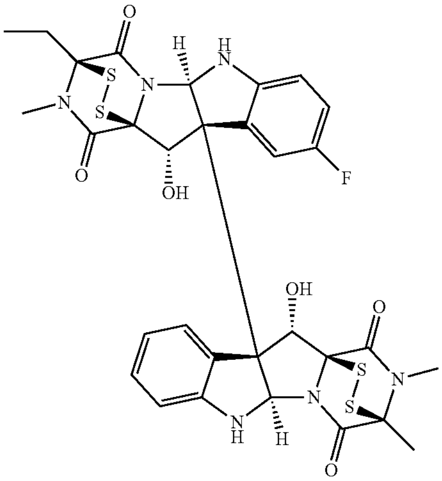

,

-continued

6

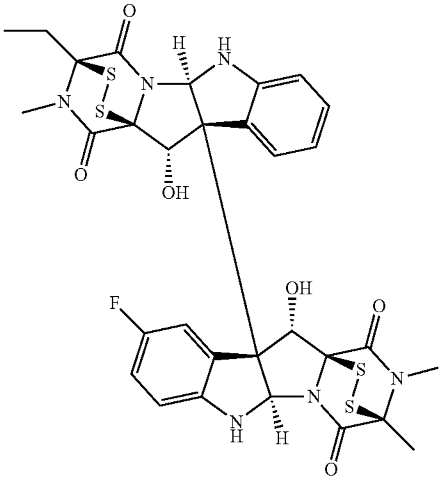

,

7

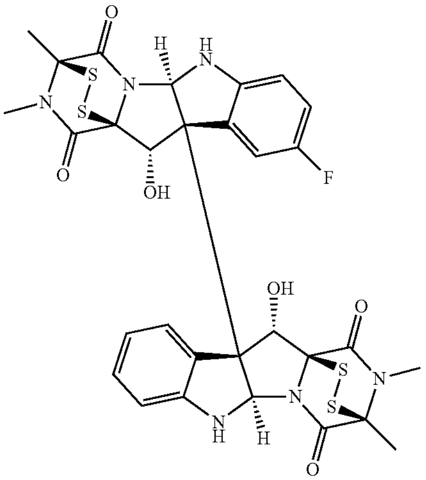

,

8

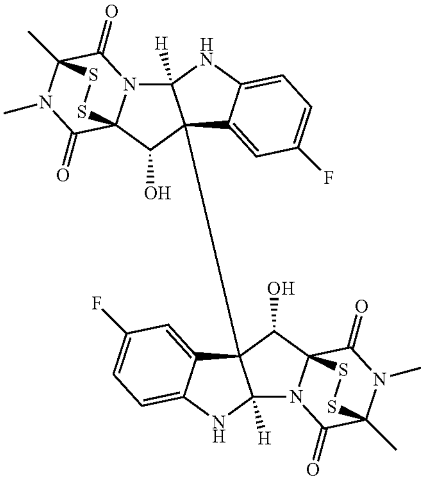

,

-continued
9
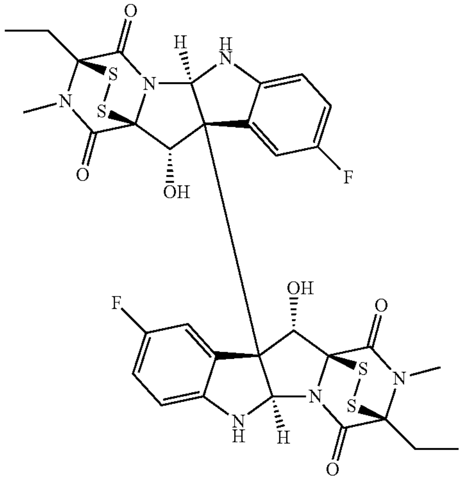
,
10
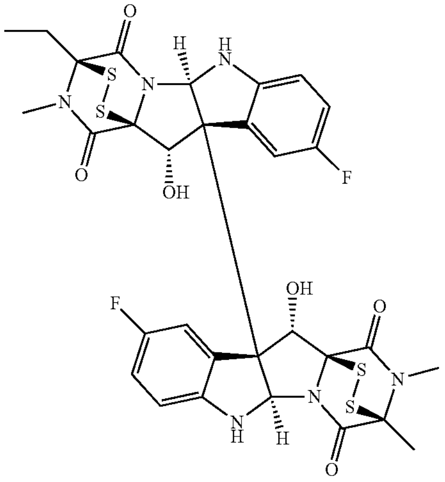
,
or a pharmaceutically acceptable salt thereof.
Further examples of these compounds are shown below:
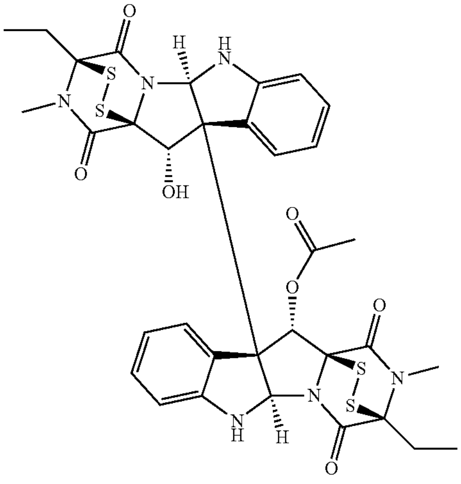
,
-continued
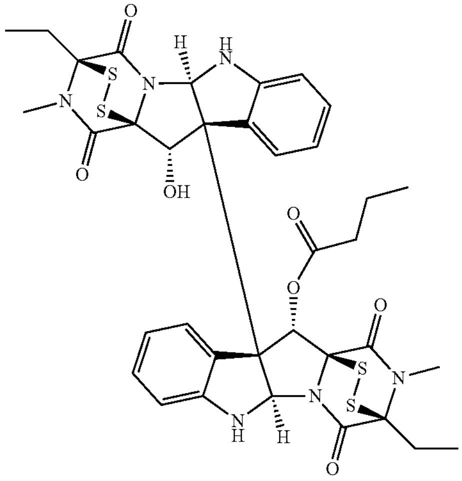
,
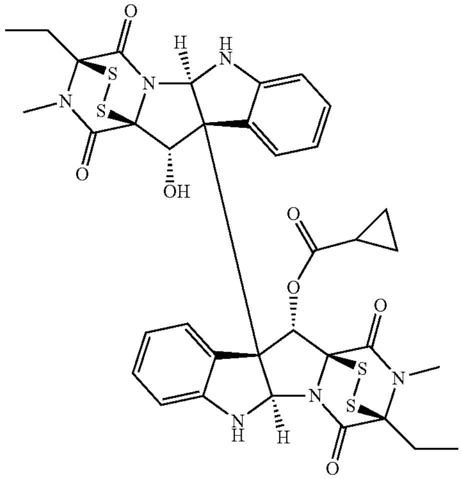
,
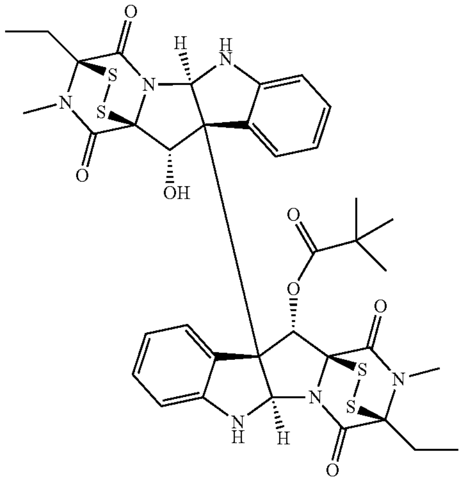
, -continued
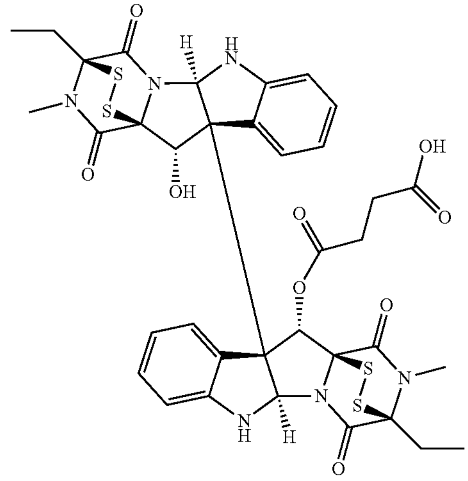
,
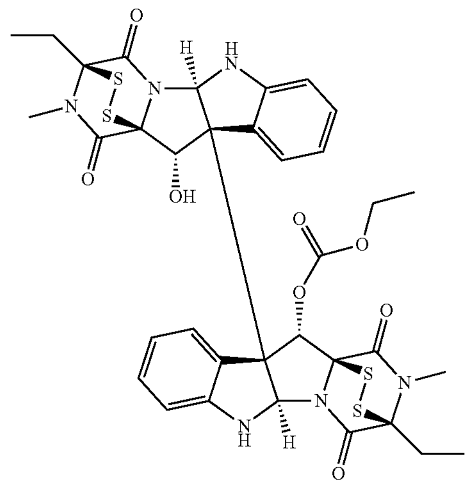
,
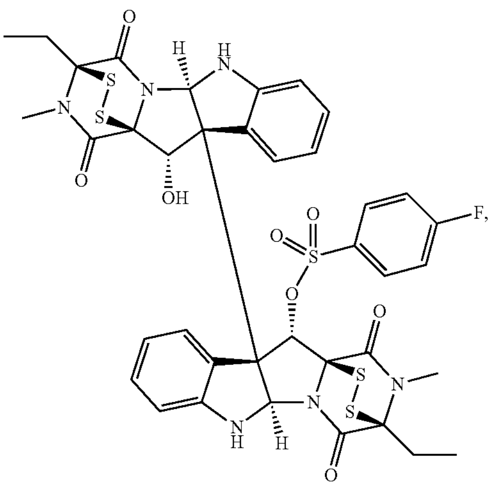
-continued
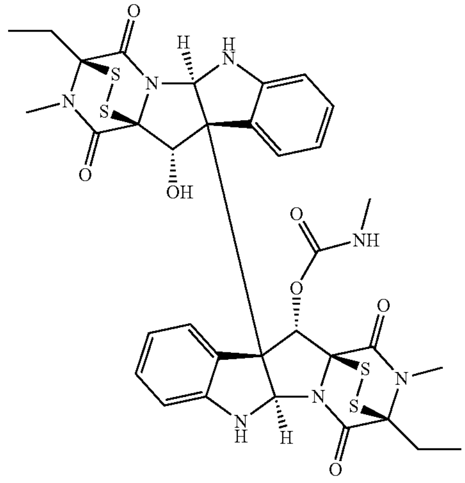
,
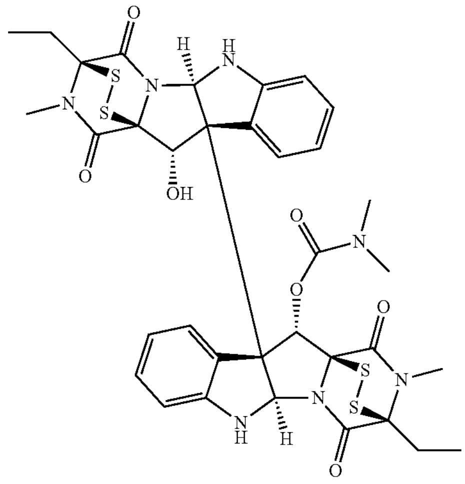
,
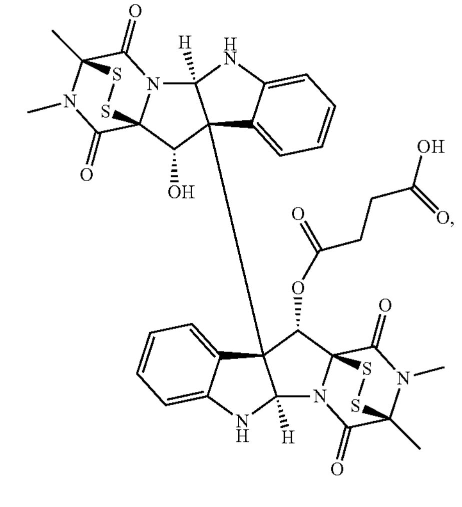
or a pharmaceutically acceptable salt thereof.

Additional examples of these compounds are shown below:
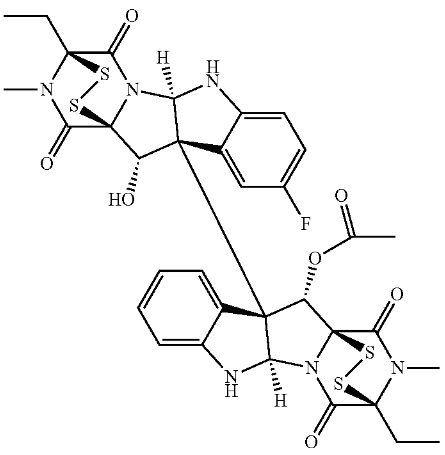
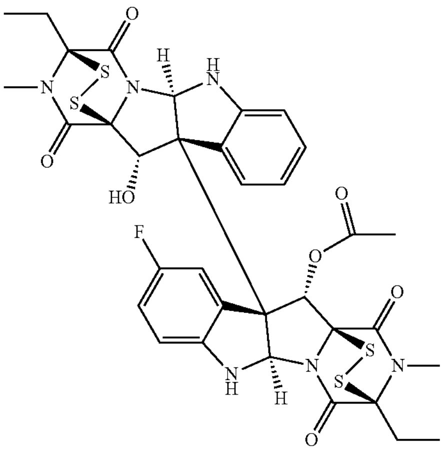
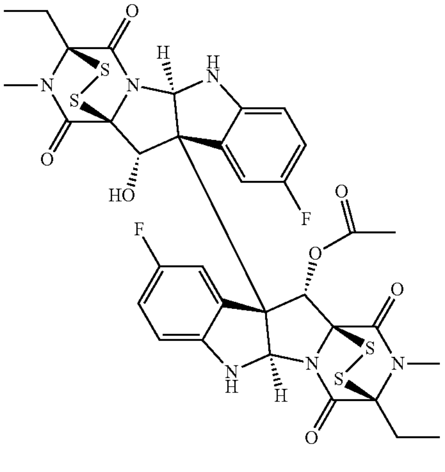
-continued
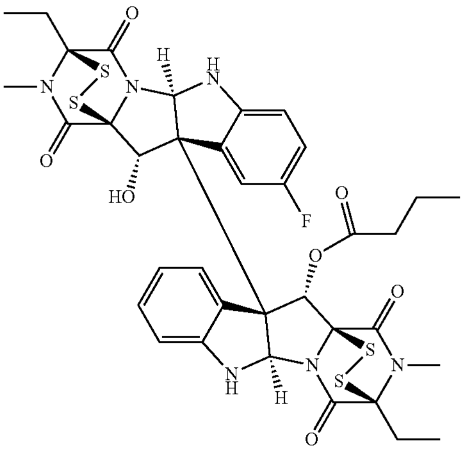
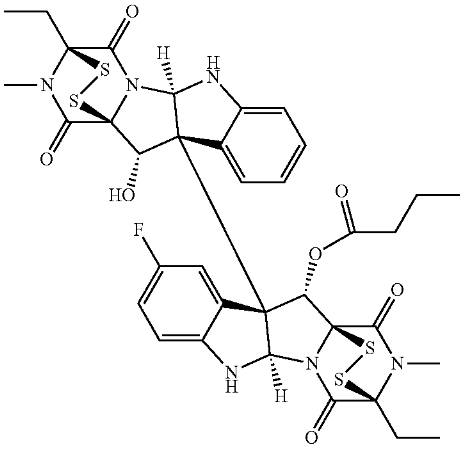
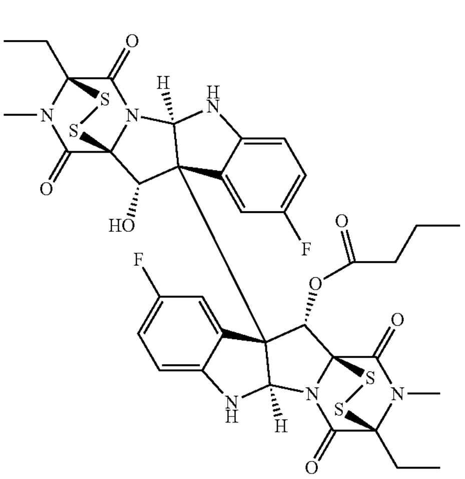

-continued
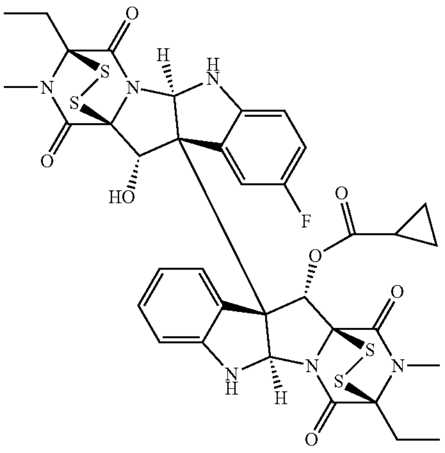
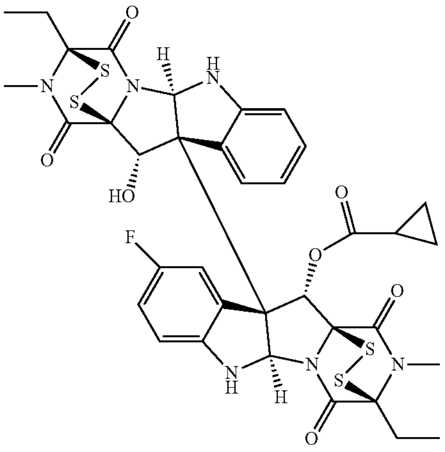
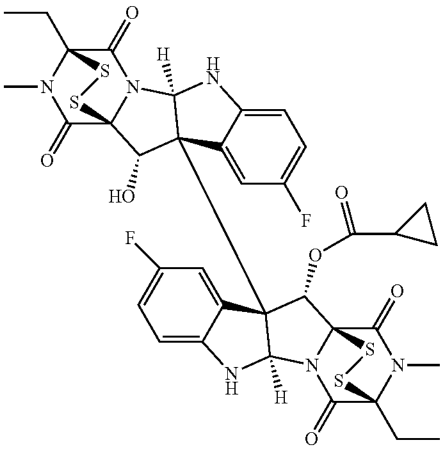
-continued
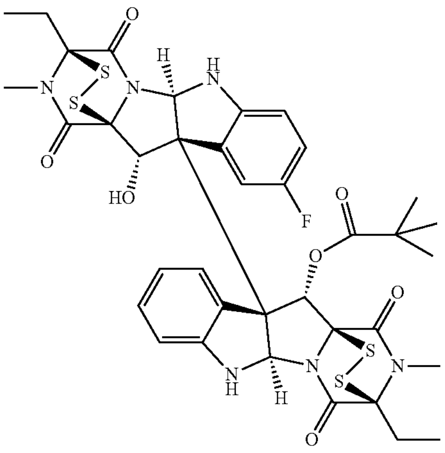
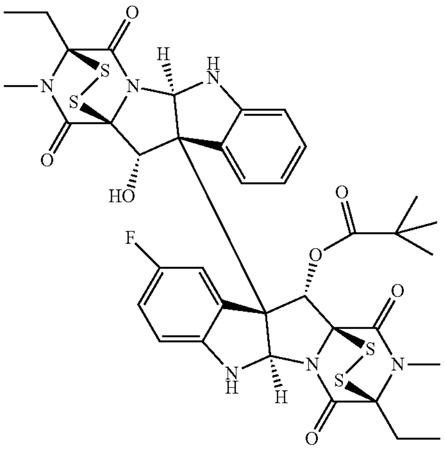
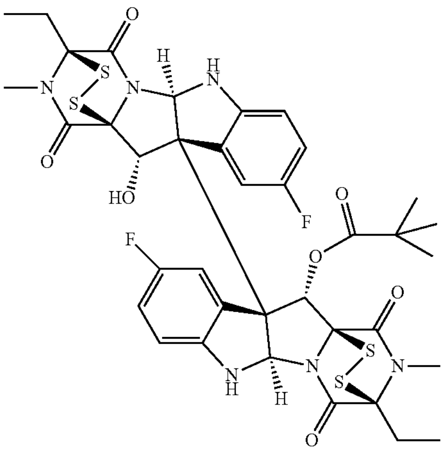

-continued
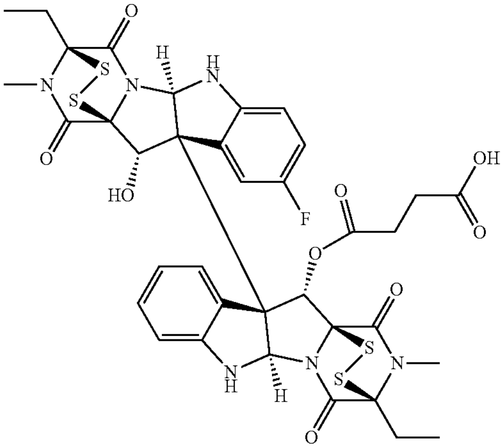
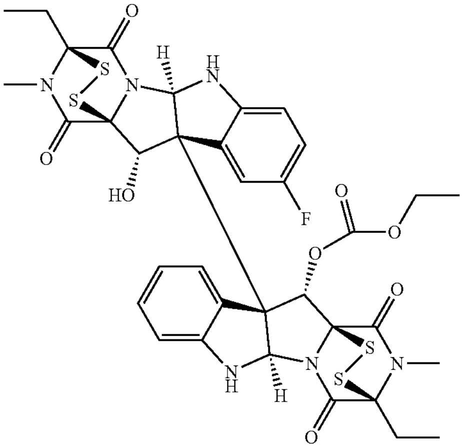
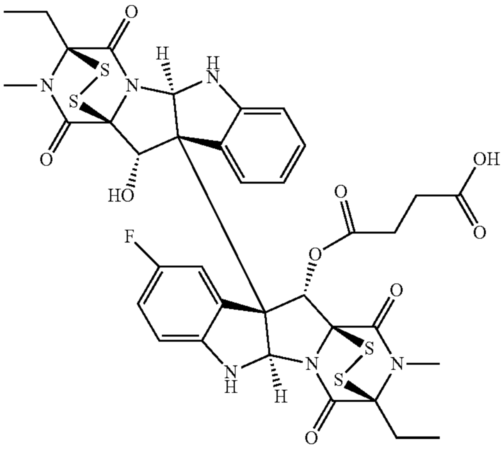
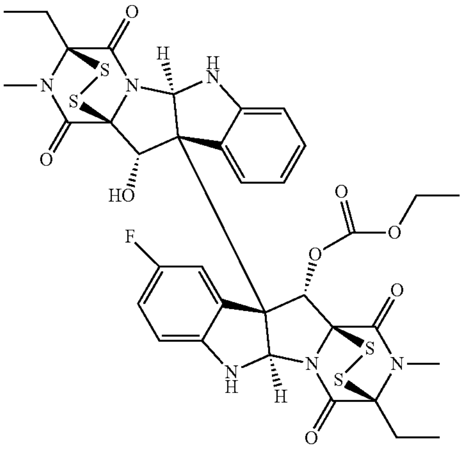
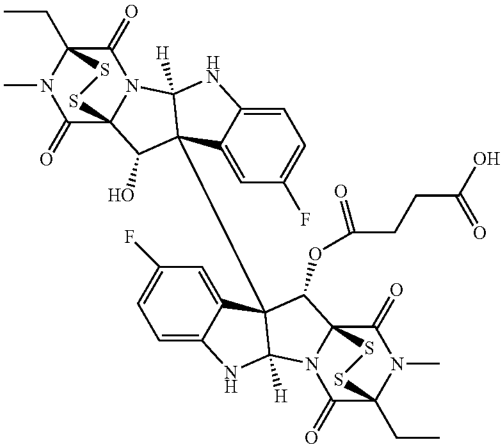
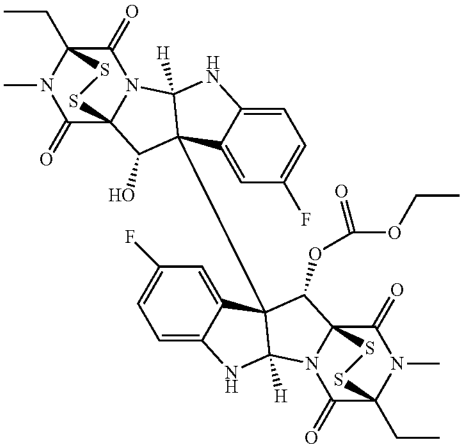

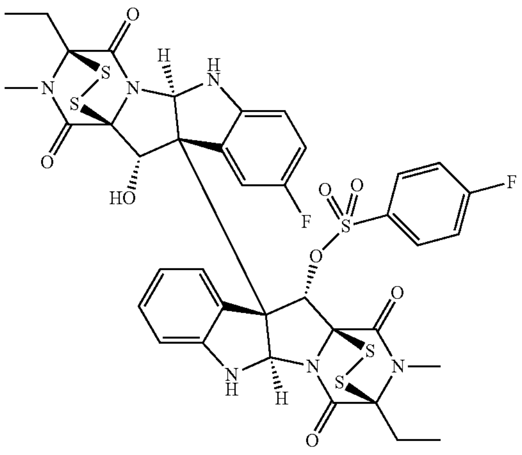
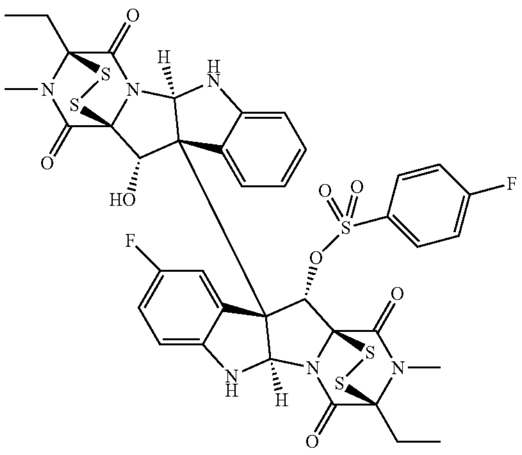
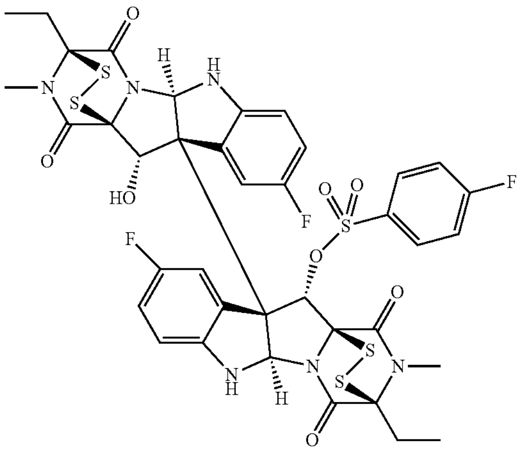
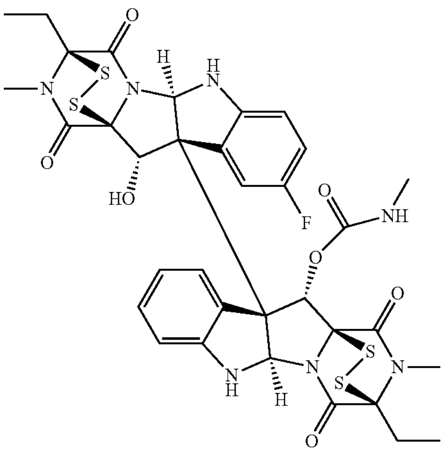
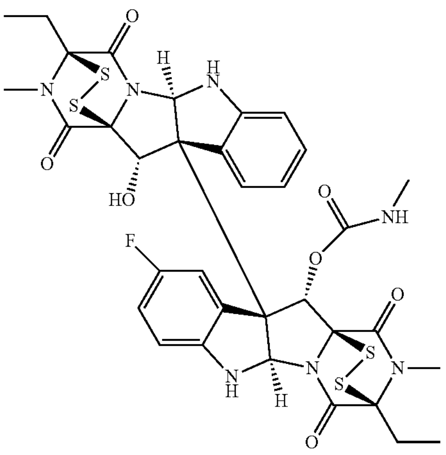
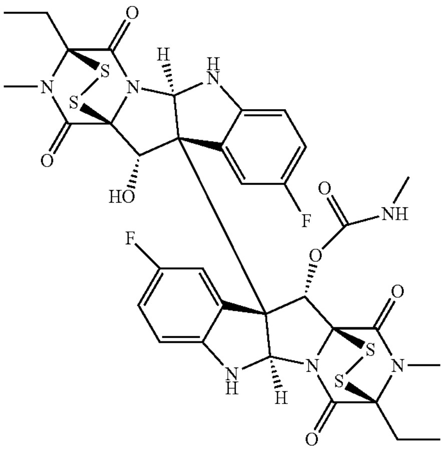

-continued
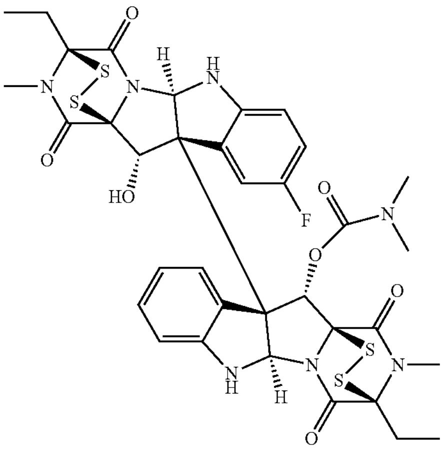
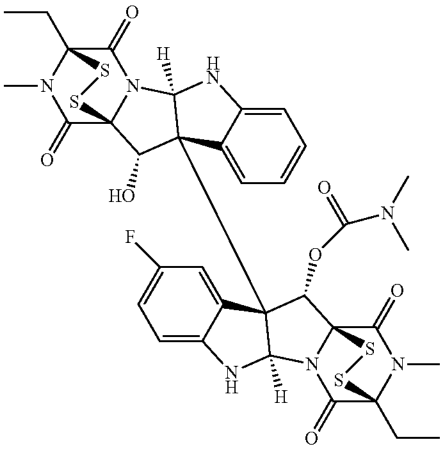
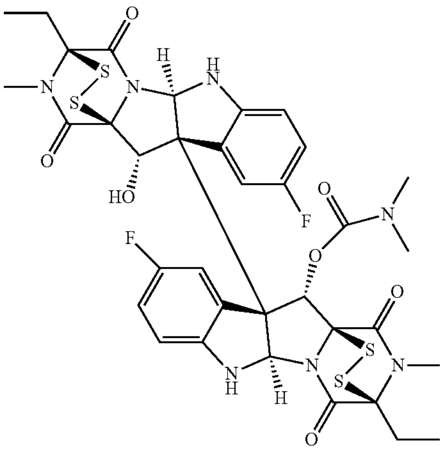
-continued
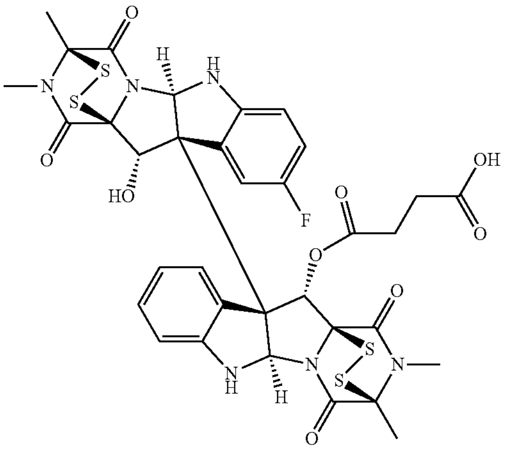
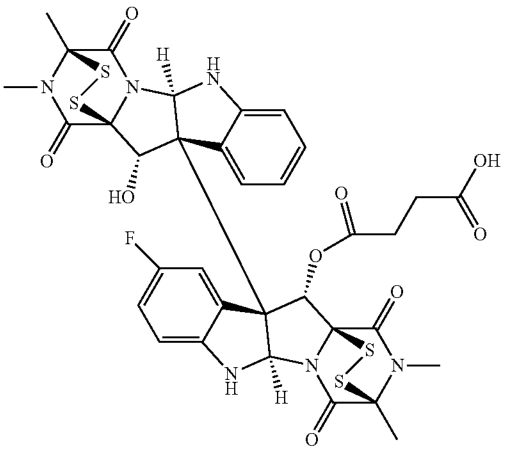
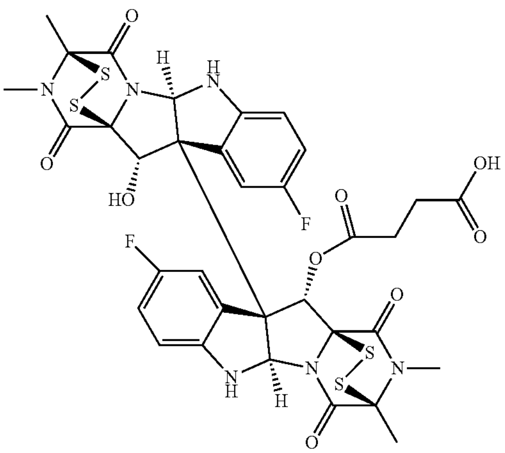

-continued
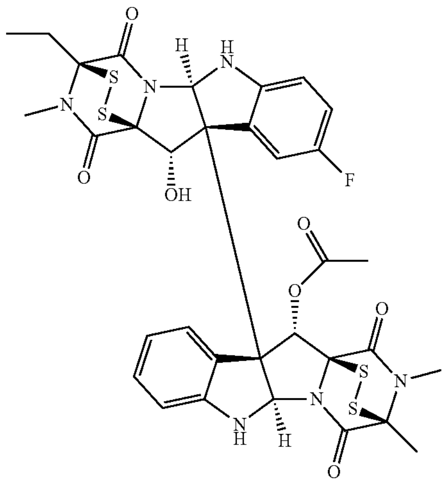
,
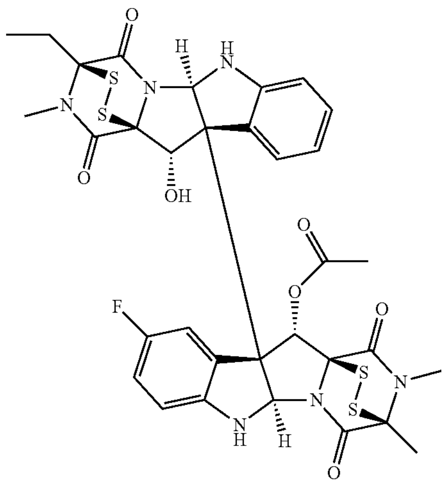
,
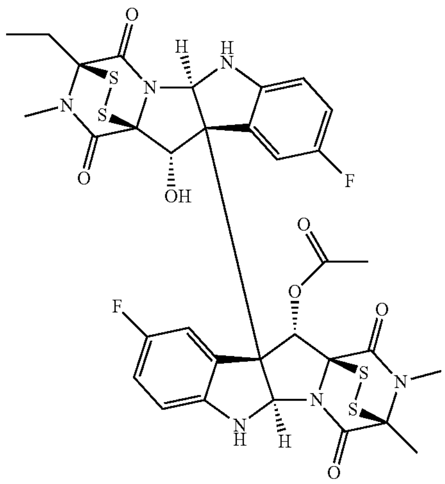
,
-continued
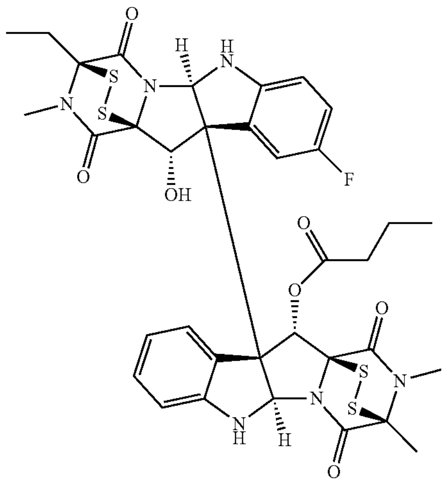
,
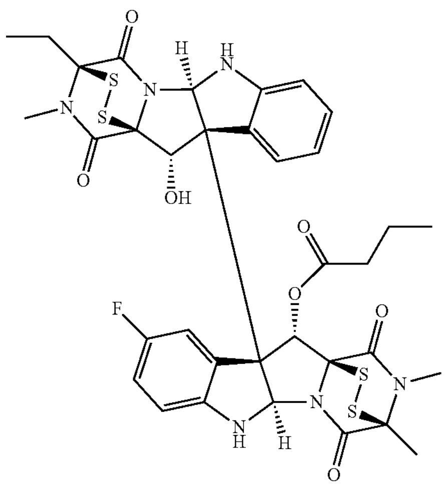
,
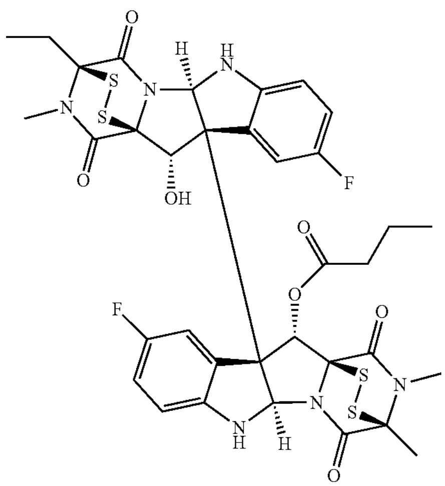
, -continued
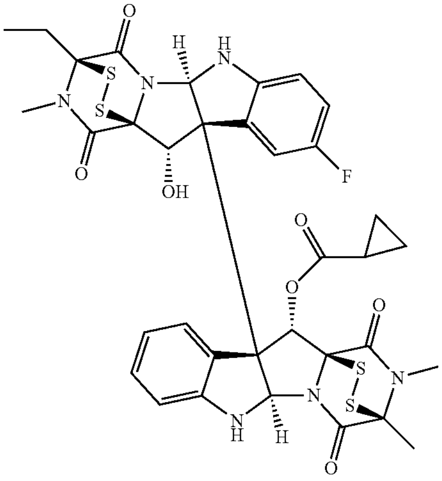
,
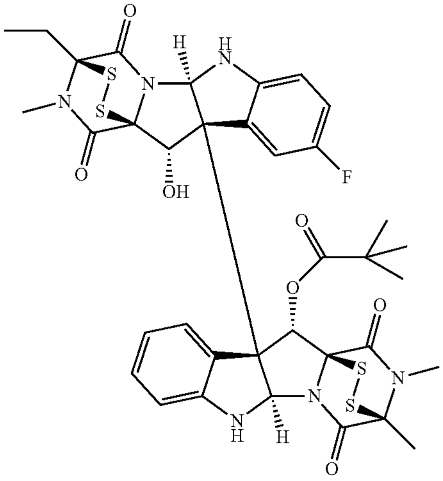
,
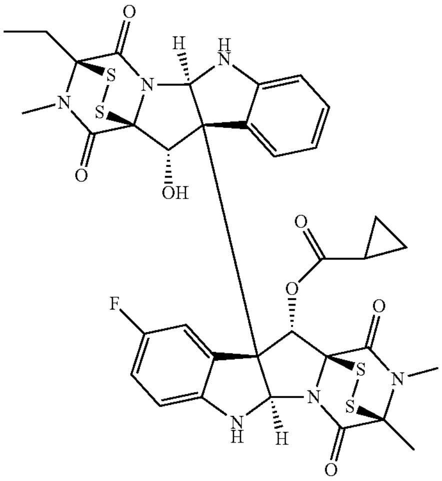
,
-continued
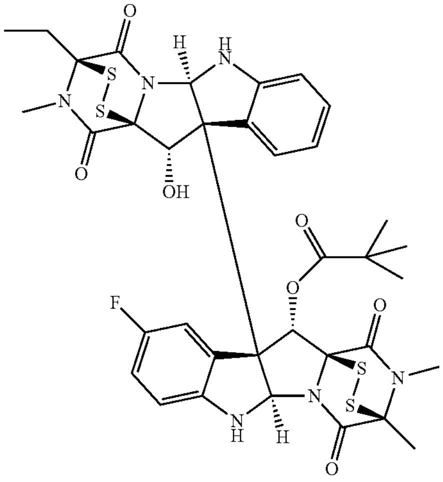
,
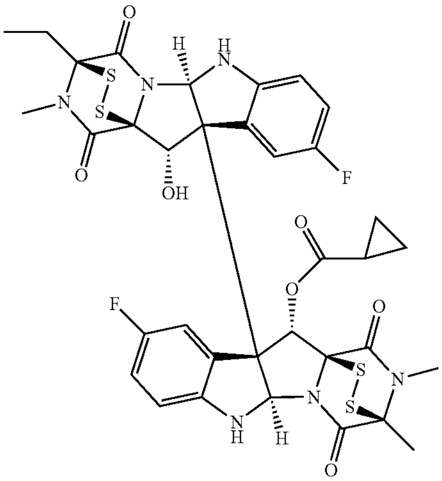
,
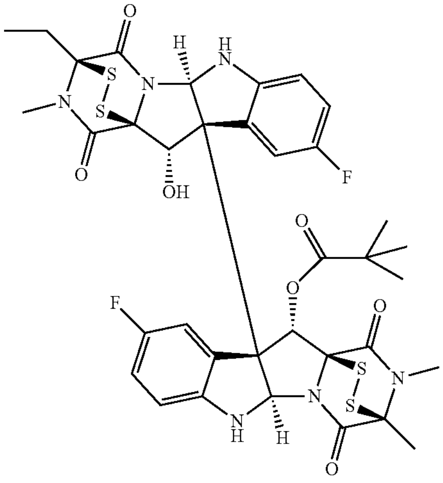
, -continued
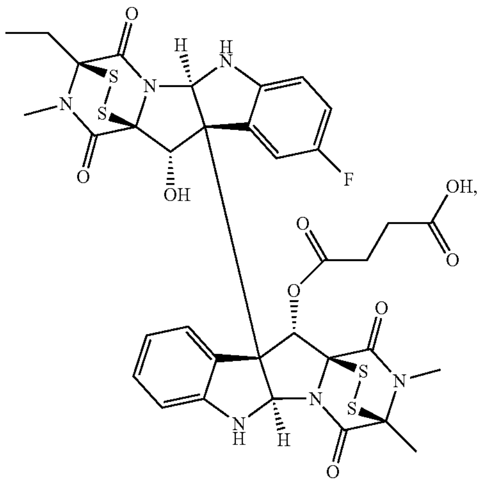
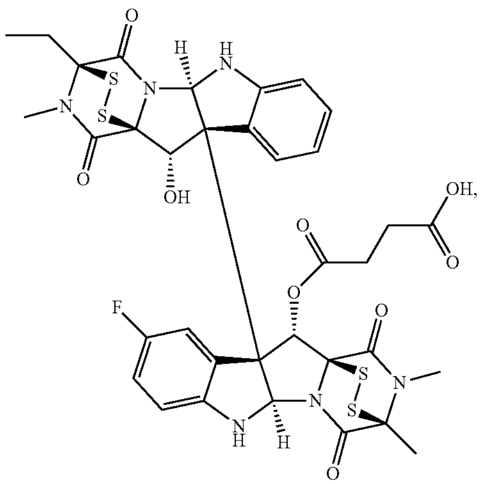
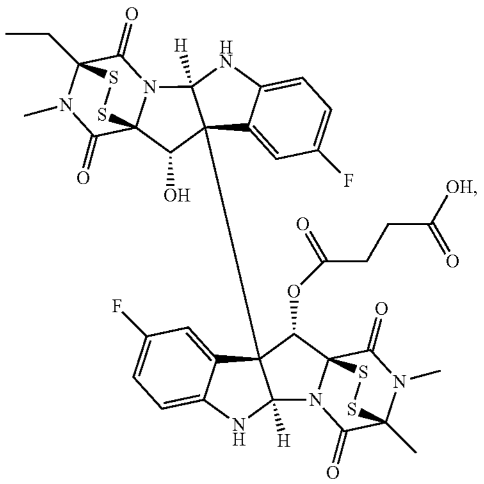
-continued
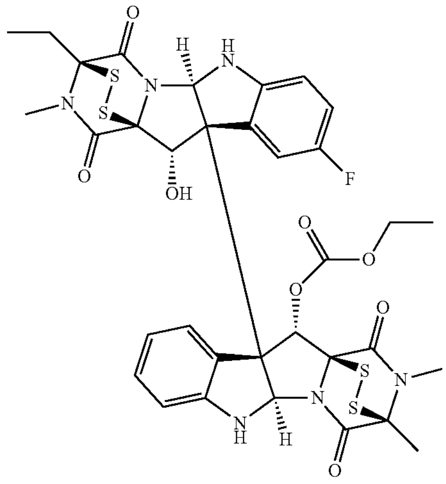
,
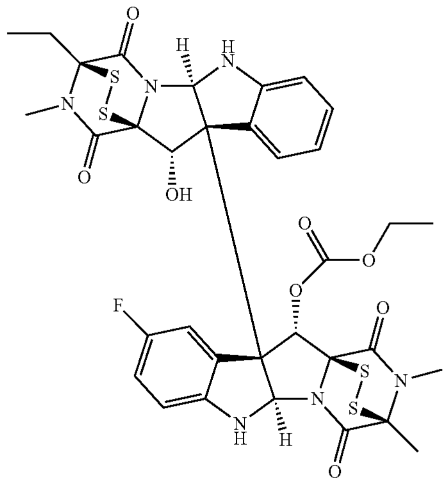
,
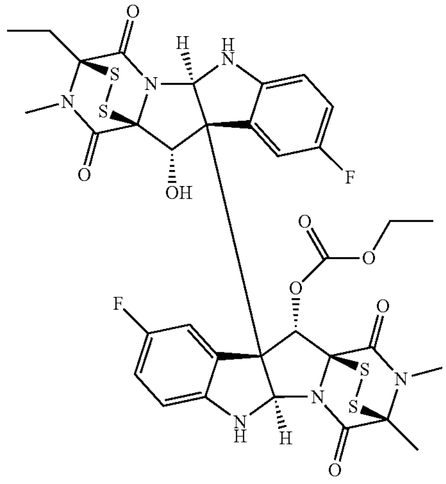
, -continued
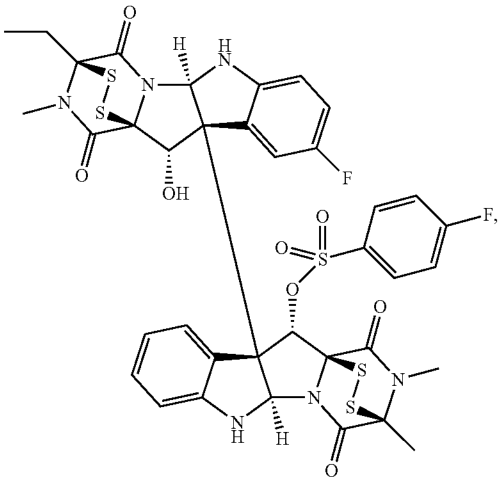
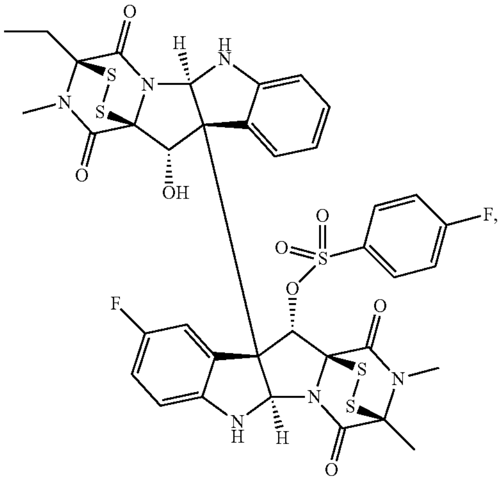
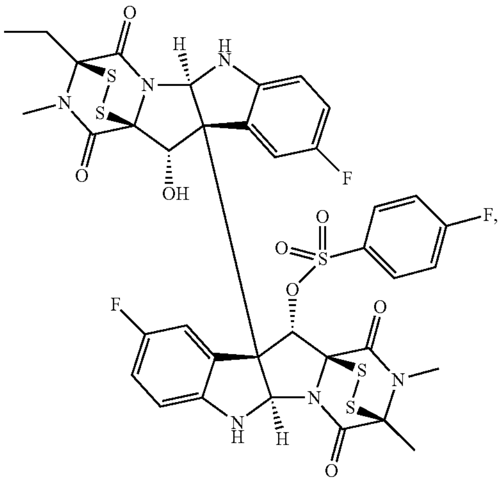
-continued
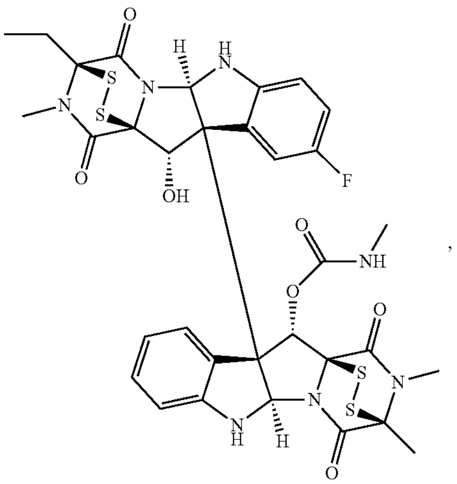
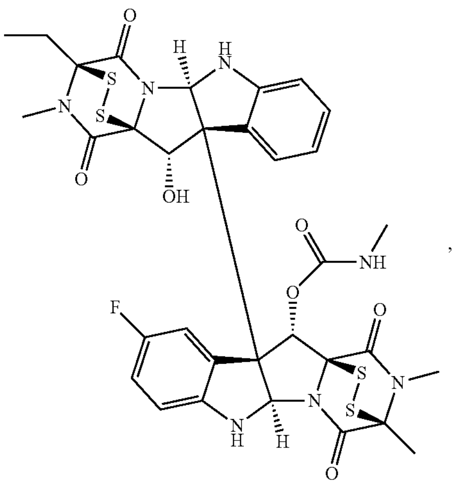
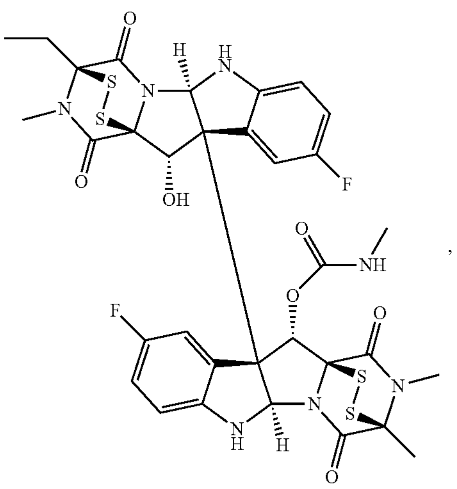

-continued
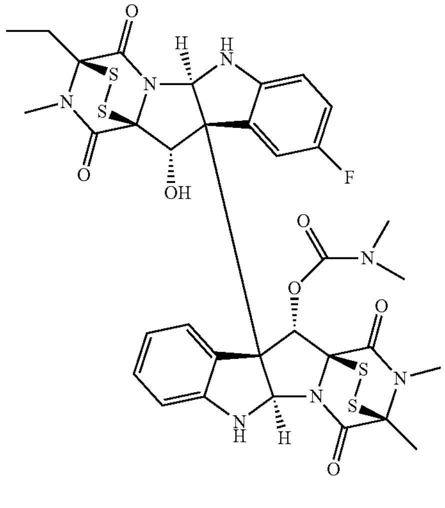
,
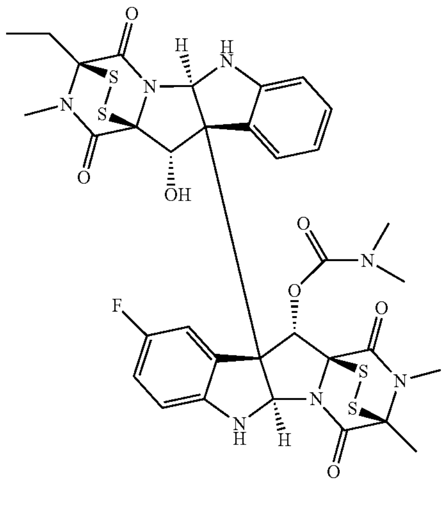
,
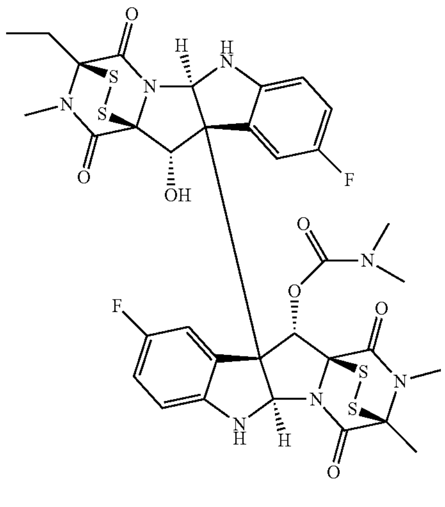
,
-continued
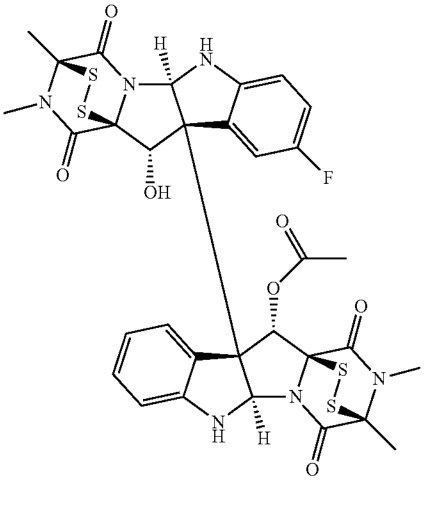
,
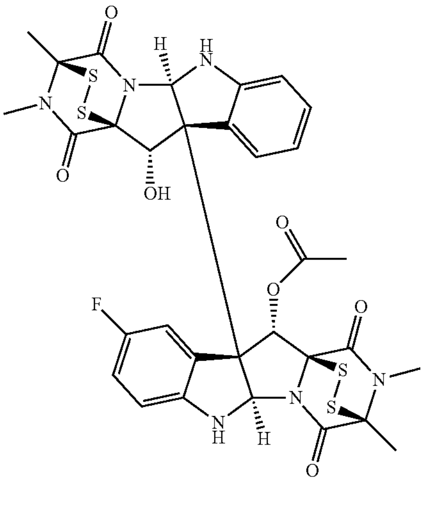
,
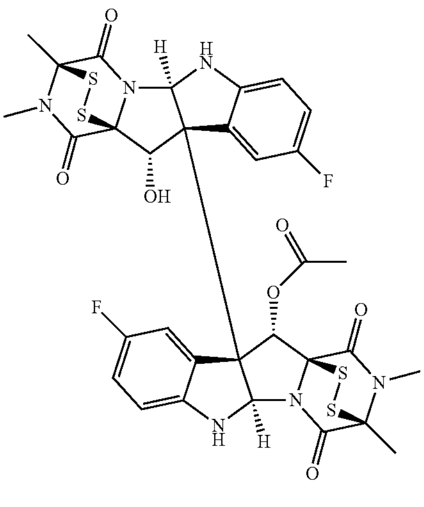
, -continued
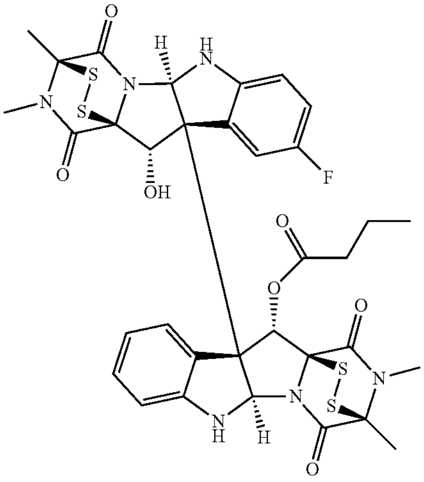
,
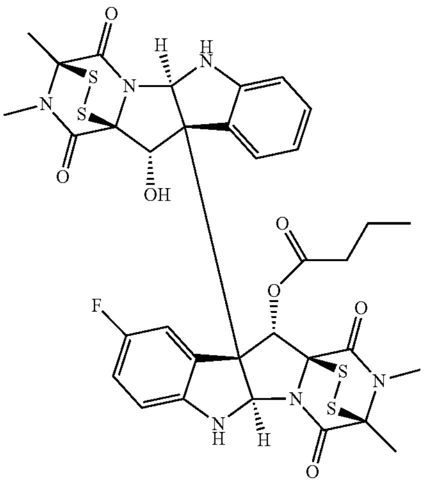
,
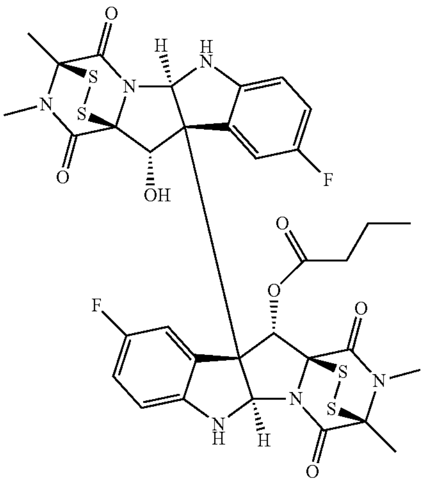
,
-continued
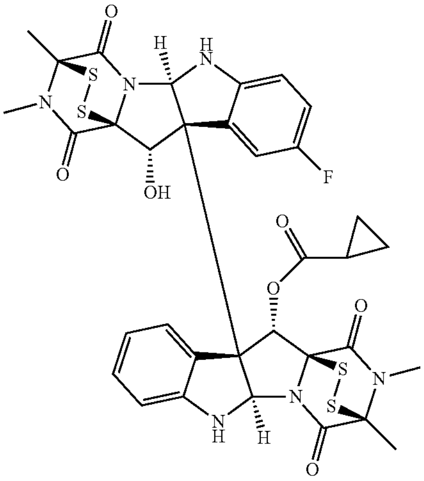
,
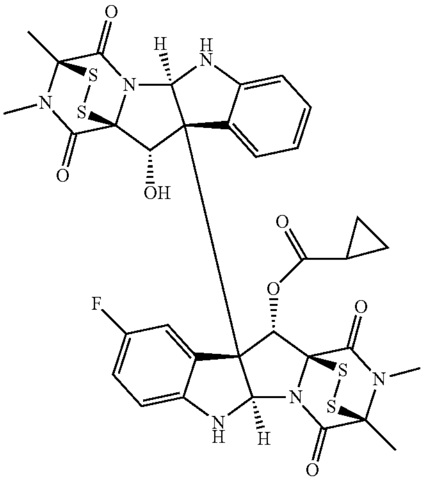
,
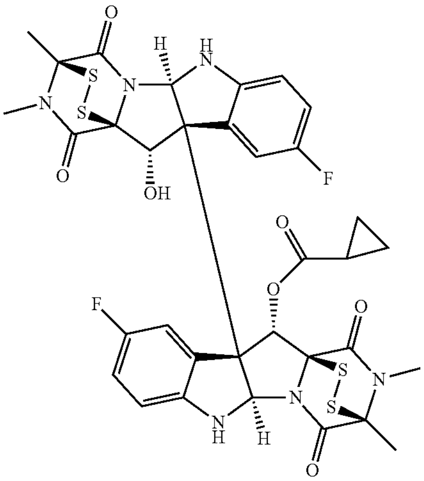
, -continued
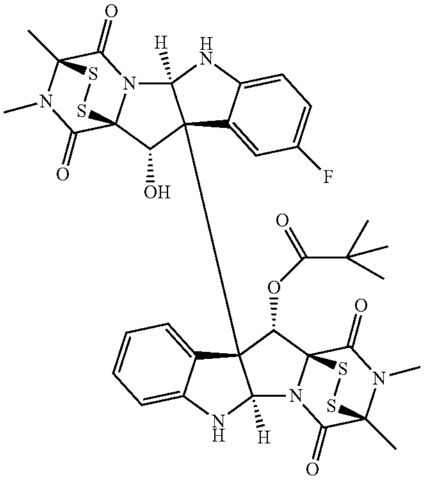
,
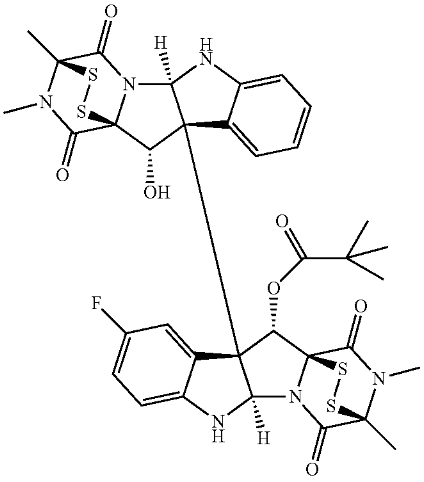
,
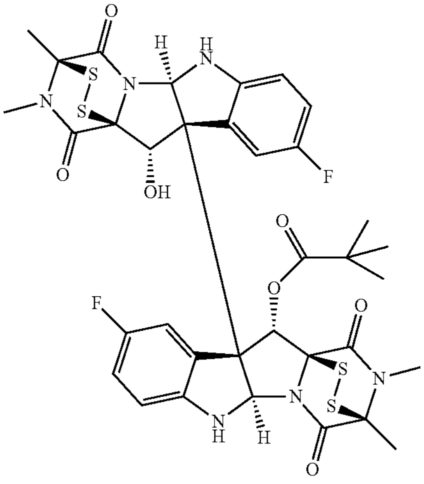
,
-continued
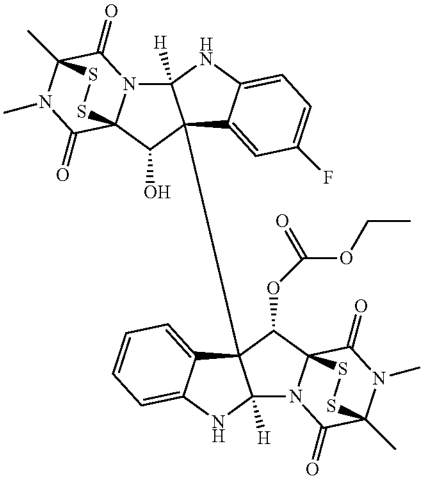
,
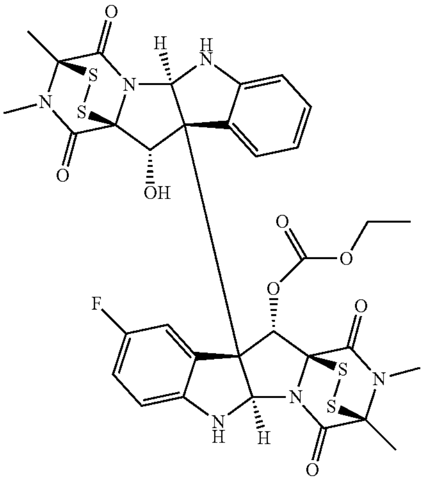
,
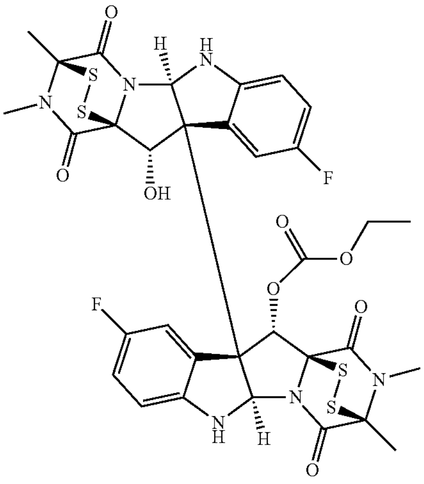
, -continued
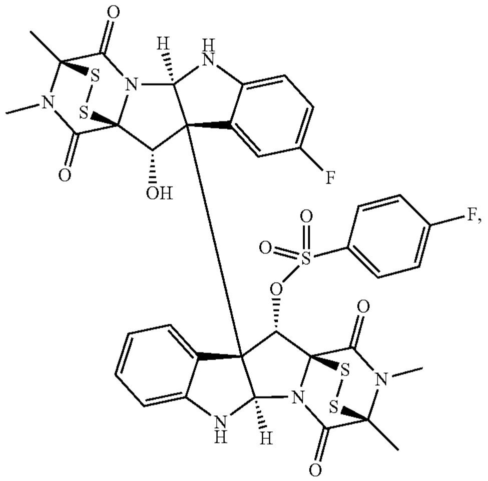
,
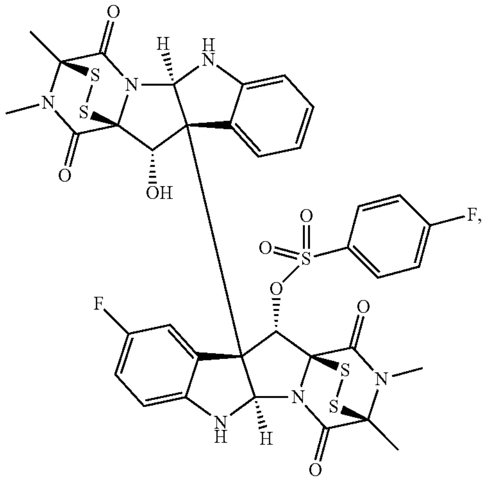
,
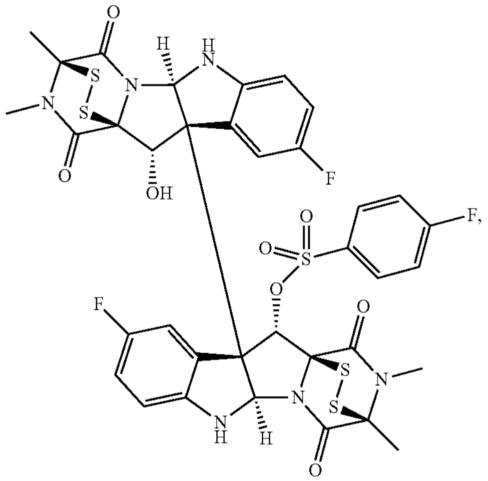
,
-continued
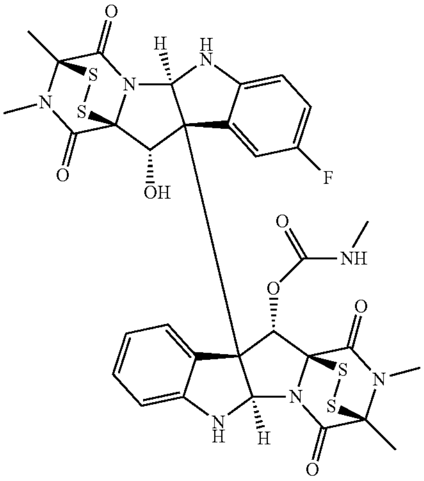
,
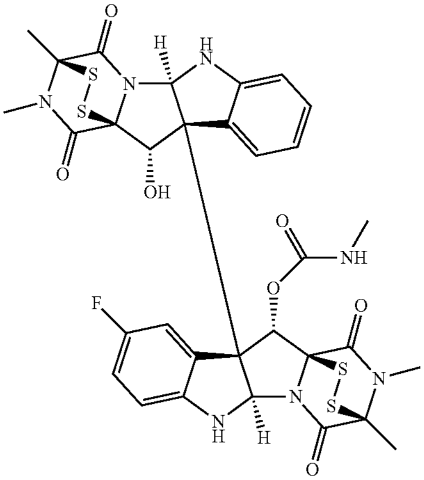
,
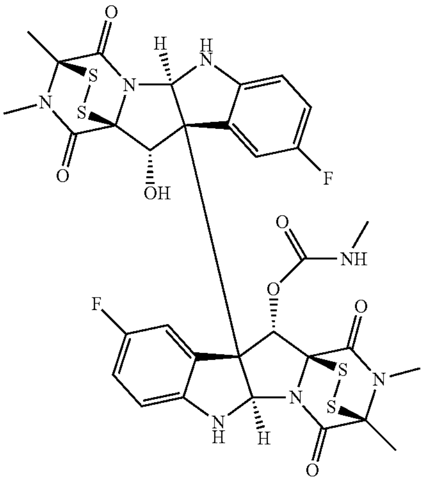
, -continued

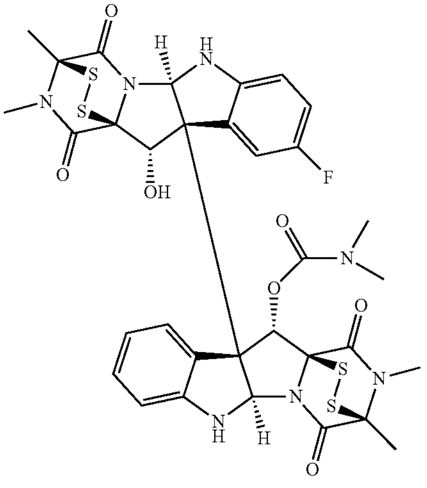

,

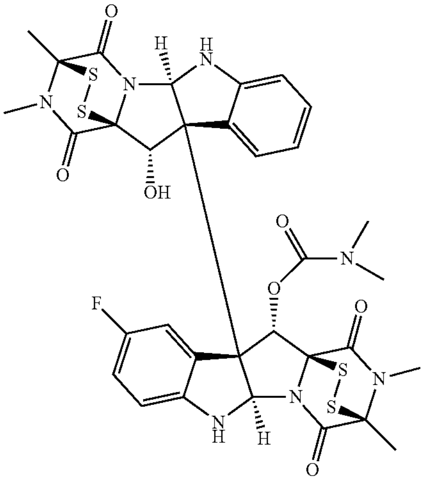

,

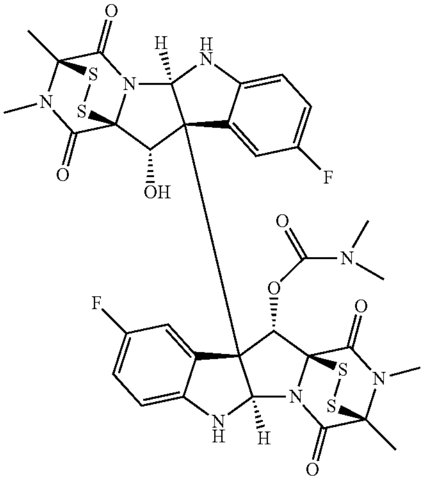

, or a pharmaceutically acceptable salt thereof.

In some embodiments, the compound has the formula:

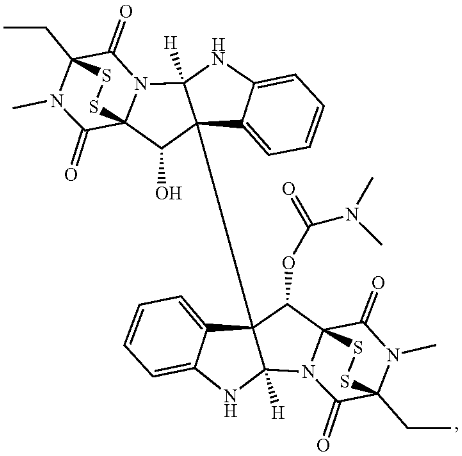 [SMILES: CC[C@@]12SS[C@]3(C(=O)N1C)[C@@H](O)[C@]1([C@@]45c6ccccc6N[C@@H]4N4C(=O)[C@]6(CC)SS[C@]4(C(=O)N6C)[C@H]5OC(=O)N(C)C)c4ccccc4N[C@@H]1N3C2=O]

or a pharmaceutically acceptable salt thereof.

In some embodiments, the compounds described herein exhibit anti-proliferative activity against cancer cells. In some embodiments, the compounds described herein also contain one or more functional groups that improve the solubility of the compounds. The compounds can have an improved solubility compared to that of the verticillin natural product at room temperature. In some instances, the solubility of the compounds ranges from 0.01 μg/ml to 2.0 μg/ml, from 0.03 μg/ml to 1.9 μg/ml, or from 0.04 μg/ml to 2.0 μg/ml. In some instances, the compounds can have a solubility of greater than 0.01 μg/ml. For example, the solubility of the compounds is greater than 0.04 μg/ml, greater than 0.05 μg/ml, greater than 0.1 μg/ml, greater than 0.5 μg/ml, greater than 0.75 μg/ml, greater than 1.0 μg/ml, greater than 1.25 μg/ml, greater than 1.5 μg/ml, or greater than 1.75 μg/ml. In some embodiments, the solubility of the compounds improves by at least 2-fold and up to 30-fold compared to the verticillin natural products. For example, the solubility of a compound can increase at least 2-fold, at least 5-fold, at least 10-fold, at least 20-fold, or at least 30-fold compared to the verticillin natural products.

Pharmaceutical Compositions

The disclosed compounds can be used therapeutically in combination with a pharmaceutically acceptable carrier. The carrier would naturally be selected to minimize any degradation of the active ingredient and to minimize any adverse side effects in the subject, as would be well known to one of skill in the art.

The disclosed compounds may be in solution, suspension, incorporated into microparticles, liposomes, or cells, or formed into tablets, gels, or suppositories. Suitable carriers and their formulations are described in Remington: The Science and Practice of Pharmacy ($22^{nd}$ ed.) eds. Loyd V. Allen, Jr., et al., Pharmaceutical Press, 2012. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered. Pharmaceutical carriers are known to those skilled in the art. These most typically would be standard carriers for administration of vaccines to humans, including solutions such as sterile water, saline, and buffered solutions at physiological pH. Pharmaceutical compositions may include carriers, thickeners, diluents, buffers, preservatives, surface active agents and the like in addition to the vaccine. Pharmaceutical compositions may also include one or more active ingredients such as antimicrobial agents, anti-inflammatory agents, anesthetics, and the like.

The disclosed compounds are preferably formulated for delivery via intranasal, intramuscular, subcutaneous, parenteral, transdermal sublingual, buccal, intravenous, intradermal, intraperitoneal, oral, eye drops, or topical administration.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Parenteral administration of the disclosed compounds, if used, is generally characterized by injection. Injectables can be prepared in conventional forms, either as liquid solutions or suspensions, solid forms suitable for solution of suspension in liquid prior to injection, or as emulsions.

For an oral administration form, the disclosed compounds can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, cornstarch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, the disclosed compounds may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the disclosure or their physiologically tolerable salts in a pharmaceutically acceptable solvent, such as ethanol or water, or a mixture of such solvents. If required, the formulation may additionally contain other pharmaceutical auxiliaries such as surfactants, emulsifiers and stabilizers as well as a propellant.

For subcutaneous or intravenous administration, the disclosed compounds, if desired with the substances customary therefore such as solubilizers, emulsifiers or further auxiliaries are brought into solution, suspension, or emulsion. The disclosed compounds may also be lyophilized and the lyophilizates obtained used, for example, for the production of injection or infusion preparations. Suitable solvents are, for example, water, physiological saline solution or alcohols, e.g. ethanol, propanol, glycerol, sugar solutions such as glucose or mannitol solutions, or mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, the formulations may be prepared by mixing the compounds with a suitable non-irritating excipient, such as cocoa butter, synthetic glyceride esters or polyethylene glycols, which are solid at ordinary temperatures, but liquefy and/or dissolve in the rectal cavity to release the drug.

In certain embodiments, it is contemplated that compositions comprising the disclosed compounds can be extended release formulations. Typical extended release formations utilize an enteric coating. Typically, a barrier is applied to oral medication that controls the location in the digestive system where it is absorbed. Enteric coatings prevent release of medication before it reaches the small intestine. Enteric coatings may contain polymers of polysaccharides, such as maltodextrin, xanthan, scleroglucan dextran, starch, alginates, pullulan, hyaloronic acid, chitin, chitosan and the like; other natural polymers, such as proteins (albumin, gelatin etc.), poly-L-lysine; sodium poly(acrylic acid); poly (hydroxyalkylmethacrylates) (for example poly(hydroxyethylmethacrylate)); carboxypolymethylene (for example Carbopol™); carbomer; polyvinylpyrrolidone; gums, such as guar gum, gum arabic, gum karaya, gum ghatti, locust bean gum, tamarind gum, gellan gum, gum tragacanth, agar, pectin, gluten and the like; poly(vinyl alcohol); ethylene vinyl alcohol; polyethylene glycol (PEG); and cellulose ethers, such as hydroxymethylcellulose (HMC), hydroxyethylcellulose (HEC), hydroxypropylcellulose (HPC), methylcellulose (MC), ethylcellulose (EC), carboxyethylcellulose (CEC), ethylhydroxyethylcellulose (EHEC), carboxymethylhydroxyethylcellulose (CMHEC), hydroxypropylmethyl-cellulose (HPMC), hydroxypropylethylcellulose (HPEC) and sodium carboxymethylcellulose (Na-CMC); as well as copolymers and/or (simple) mixtures of any of the above polymers. Certain of the above-mentioned polymers may further be crosslinked by way of standard techniques.

The choice of polymer will be determined by the nature of the active ingredient/drug that is employed in the composition of the disclosure as well as the desired rate of release. In particular, it will be appreciated by the skilled person, for example in the case of HPMC, that a higher molecular weight will, in general, provide a slower rate of release of drug from the composition. Furthermore, in the case of HPMC, different degrees of substitution of methoxyl groups and hydroxypropoxyl groups will give rise to changes in the rate of release of drug from the composition. In this respect, and as stated above, it may be desirable to provide compositions of the disclosure in the form of coatings in which the polymer carrier is provided by way of a blend of two or more polymers of, for example, different molecular weights in order to produce a particular required or desired release profile.

Microspheres of polylactide, polyglycolide, and their copolymers poly(lactide-co-glycolide) may be used to form sustained-release delivery systems. The disclosed compounds can be entrapped in the poly(lactide-co-glycolide) microsphere depot by a number of methods, including formation of a water-in-oil emulsion with water-borne compound and organic solvent-borne polymer (emulsion method), formation of a solid-in-oil suspension with solid compound dispersed in a solvent-based polymer solution (suspension method), or by dissolving the compound in a solvent-based polymer solution (dissolution method). One can attach poly(ethylene glycol) to compounds (PEGylation) to increase the in vivo half-life of circulating therapeutic proteins and decrease the chance of an immune response.

Liposomal suspensions (including liposomes targeted to viral antigens) may also be prepared by conventional methods to produce pharmaceutically acceptable carriers. This may be appropriate for the delivery of free nucleosides, acyl nucleosides or phosphate ester prodrug forms of the nucleoside compounds according to the present disclosure.

The exact amount of the compounds or compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products. A typical dosage of the disclosed vaccine used alone might range from about 1 μg/kg to up to 100 mg/kg of body weight or more per vaccination, such as 10 μg/kg to 50 mg/kg, or 50 μg/kg to 10 mg/kg, depending on the factors mentioned above.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Some of the disclosed compounds may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The pharmaceutical preparations of the disclosure are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the disclosure, e.g., about 10, 25, 50, 100, 200, 300 or 400 mg per unit dosage.

The disclosed compounds can also be used to supplement existing treatments. Therefore, the disclosed compositions can further include (or be administered in combination with) a second compound that can ameliorate, diminishing, reversing, treating or preventing cancer in a subject. For example, the disclosed compositions can further include (or be administered in combination with) one or more chemotherapeutic agents. In a specific embodiment, the disclosed compounds can be administered with (in combination in the same composition, in combination but in separate compositions, or sequentially) approved drugs for treating cancer.

The pharmaceutical compositions and formulations disclosed herein can be administered for prophylactic and/or therapeutic treatments. In therapeutic applications, compositions are administered to a subject already having a tumor.

The amount of pharmaceutical composition adequate to accomplish this is defined as a "therapeutically effective dose." The dosage schedule and amounts effective for this use, i.e., the "dosing regimen," will depend upon a variety of factors, including the stage of the condition, the severity of the condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods of the invention are correct and appropriate.

Methods for Synthesis

The compounds described herein can be prepared by a variety of methodologies. One approach involves using precursor-directed biosynthesis which harnesses the biosynthetic machinery of a microorganism by introducing analogous building blocks to those used naturally. For example, fluorinated verticillins were prepared by incorporating fluorinated amino acids such fluorinated 5-F-DL-tryptophan (5-F-DL-Trp) into culture media of the fungus *Clonostachys rogersoniana* (strain MSX59553) resulted in seven fluorinated analogues (compounds 4-10).

Another approach involves the acetylation of verticillins or verticillins derivatives such as the fluorinated verticillins (compounds 4-10). For example, verticillin H can be treated first with acetic anhydride under conditions similar to those previously reported resulting in the acylation of only a single alcohol moiety to generate compound 11.

A series of four additional ester analogues (compounds 12-15) were also generated, demonstrating the ability to generate both straight chain and branched chain derivatives. Despite the additional steric congestion, the pivaloyl derivative 14 was obtained in comparable or even better yield than the other ester analogues. This result suggests that although the conformation of the acylated derivatives precludes further reaction at the C11' position, there is no significant size limitation for the initial acylation event. The most interesting of these four examples, however, is the succinate 15. In this case, the ester was formed through addition into succinic anhydride rather than an acid chloride. The introduction of the succinic acid moiety is commonly employed for prodrug development and can dramatically impact the relative water solubility of the natural product. Similar to the esters, carbonate 16 was generated upon treatment of verticillin H with ethyl chloroformate. Carbamates 18 and 19, however, were generated through a two-step procedure involving initial acylation with carbonyldiimidazole and subsequent treatment with the desired amine precursor for the formation of the carbamate.

In some embodiments, the verticillin derivatives that are used as the starting materials are fluorinated verticillin derivatives 4-10. The fluorinated verticillin derivatives are reacted with reagents, as described for compounds 11 through 20.

Methods of Use

The present disclosure provides methods for treating or ameliorating at least one symptom or indication of cancer including administering to a subject in need thereof a pharmaceutical composition including a therapeutically effective amount of a compound described herein. In specific embodiments, the present disclosure provides methods for treating or ameliorating at least one symptom or indication, or inhibiting the growth of tumors. In certain embodiments, the present disclosure provides a method for inhibiting a histone methyltransferase.

The methods can comprise administering to a subject in need thereof an effective amount of a compound or composition disclosed herein. In some embodiments, the compounds and compositions can be in an effective amount to inhibit a histone methyltransferase. The methyltransferase can be selected from G9a, GLP, SUV39H1, SUV39H2, MLL1, or NSD2.

In certain embodiments, the cancer or tumor is a solid tumor or malignancy. The methods described herein can cause a therapeutic injury resulting in the reduction of at least one of surface area, the depth, and the amount of the tissue affected by the cancerous condition. In certain embodiments, the compounds and compositions can be used in the treatment of cancer of the bile duct, bone, bladder, head and neck, kidney, liver, gastrointestinal tissue, esophagus, ovary, endometrium, pancreas, skin, testes, thyroid, uterus, cervix and vulva, and of leukemias (including ALL and CML), multiple myeloma and lymphomas. In specific embodiments, the compounds and compositions can be used in the treatment of lung cancer, anal cancer, colorectal cancer, prostate cancer, melanoma, renal cancer, skin cancer, testicular cancer, ovarian cancer, breast cancer, endometrial cancer, kidney cancer, gastric cancer, sarcomas, bladder cancer, brain cancer, cervical cancer, gastrointestinal cancer, genitourinary cancer, esophageal cancer, pancreatic cancer, colon cancer, liver cancer, uterine cancer, bone cancer, stomach cancer, salivary gland cancer, head and neck cancers, myeloid leukemia, adrenal gland cancer, tumors of the central nervous system and their metastases, and also for the treatment of glioblastomas and myeloma. In some specific embodiments, the cancer is lung cancer.

In some embodiments, compounds and compositions disclosed herein could be used in the clinic either as a single agent by itself, in combination with radiation, additional chemotherapy agent, or in combination with both radiation and an additional chemotherapy agent. Such chemotherapy agent can include one or more of the following categories of anti-tumor agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); antitumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon;

(ii) cytostatic agents such as anti-estrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents that inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab), farnesyl transferase inhibitors, tyrosine kinase inhibitors and serine/threonine kinase inhibitors, for example inhibitors of the epidermal growth factor family (for example EGFR family tyrosine kinase inhibitors such as: N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors or phosphotidylinositol 3-kinase (PI3K) and for example inhibitors of mitogen activated protein kinase kinase (MEK1/2) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies, and approaches using the immunomodulatory drugs thalidomide and lenalidomide [Revlimid®].

Combination treatment with an additional chemotherapy agent can be achieved by way of the simultaneous, sequential or separate dosing of the individual components of the treatment. Such combination products employ the compounds or compositions of this disclosure, or pharmaceutically acceptable salts thereof, within the dosage range described hereinbefore and the other pharmaceutically-active agent within its approved dosage range.

The methods described herein are provided for treating or ameliorating at least one symptom or indication, or inhibiting the growth of cancer in a subject. In certain embodiments, methods are provided for increasing the overall or progression-free survival of a patient with cancer.

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

The following examples are set forth below to illustrate the compounds compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Generation of Fluorinated Epipolythiodioxopiperazine Alkaloids

Precursor-directed biosynthesis was used to generate a series of fluorinated epipolythiodioxopiperazine alkaloids. The biosynthesis of these verticillin analogues was monitored in situ via the droplet liquid micro-junction surface sampling probe (droplet probe), and a suite of NMR and mass spectrometry data were used for their characterization. All analogues demonstrated nanomolar $IC_{50}$ values vs a panel of cancer cell lines. This approach yielded novel compounds that would be difficult to generate via synthesis.

Background

Fluorine and nitrogen have similar natural abundances, yet only 12 secondary metabolites (five compound classes) have been discovered that include a fluorine, and none were fungal derived.[1] Interest in the fluorination of drug leads started in the 1950's after the success of 9-α-fluorohydrocortisone,[2] and this was followed by 5-fluorouracil, which is still used in chemotherapy.[3] The introduction of even a single fluorine often enhances pharmacological properties,[1a, 4] such as potency, pKa, membrane permeability, metabolism, and pharmacokinetics.[5] Fluorinated compounds increased from 2% of marketed drugs in the 1970's to approximately 20-30% today.[5b, 6] Notably, more than 30% of the most prescribed drugs contain fluorine,[6] including fluoxitine[7] (Prozac), ciprofloxacin[8] (Ciprobay), sitagliptin[9] (Januvia), and rosuvastatin (Crestor), which was the 13$^{th}$ most prescribed drug in 2013, surpassing its fluorinated predecessor, atorvastatin (Lipitor).[10]

Despite the advantages of fluorination, its incorporation in natural product derived drug leads is challenging.[11] Several strategies have been developed toward synthetic and semi-synthetic methods for selective fluorination.[12] However, this remains difficult in structurally complex natural products, which can be sensitive to degradation.[13]

As an alternative, precursor-directed biosynthesis harnesses the biosynthetic machinery of a microorganism by introducing analogous building blocks to those used naturally.[13-4] For example, incorporating fluorinated amino acids into culture media of the fungus *Beauveria bassiana* resulted in analogues with cytotoxicity against metastatic prostate cancer cells.[15] Another example was flurithromycin, a fluorinated analogue of erythromycin with improved bioavailability and longer half-life.[16] Recently, this technique was used for biosynthesizing fluorinated peptaibols.[17]

Given the potential benefit of fluorinating lead natural products, this approach was applied to the verticillins (1-3), fungal metabolites also termed epipolythiodioxopiperazine (ETP) alkaloids.[18] Verticillin A (3)[19] and its conjugates showed nanomolar cytotoxicity against a panel of cancer cell lines.[20] Compound 3 is a selective histone methyltransferase (HMTases) inhibitor.[21] In pancreatic cancer, 3 inhibited the methyltransferase enzyme MLL1 with an $IC_{50}$ of 0.8 μM resulting in demethylation of histone H3K4me3, consistent with a decrease of PD-L1 (programmed death ligand 1) expression. In vivo orthotropic tumors in mice transplanted with either PANC02-H7 or UN-KC-6141 cells had significantly smaller tumor size when treated with a combination of 3 and anti PD-L1.[22] In a separate study, a combined treatment of 3 and 5-fluorouracil in a murine model of metastatic colon carcinoma exhibited significantly smaller tumors compared to control.[21] In total, 3 has shown promise in both in vitro and in vivo cancer models.

Several ways to fluorinate verticillins could be envisaged. The Movassaghi group has made impressive progress on the synthesis of ETPs. However, they reported the total synthesis of 11, 11' dideoxyverticillin A, lacking key OH moieties.[23] Semisynthesis could suffer from disulfide bridge integrity under the fluorination conditions, resulting in a loss of activity.[24] In this example, the verticillins were investigated for precursor-directed biosynthesis by providing fluorinated 5-F-DL-tryptophan (5-FDL-Trp) to the fungus *Clonostachys rogersoniana* (strain MSX59553).

Materials and Methods

All solvents were obtained from Fisher Scientific and used without further purification. The 5-F-DL-Tryptophan was purchased from Acros Organics, 5-F-D-Tryptophan and 5-F-L-Tryptophan were purchased from Biosynth® NMR data were collected in CDCl3 using either a JEOL ECA-500 NMR spectrometer (JEOL USA, Inc.) operating at 500 MHz for 1H, 470 MHz for 19F and 125 MHz for 13C, an Agilent 700 MHz NMR spectrometer (Agilent technologies, Inc., Santa Clara, CA, USA) operating at 700 MHz for 1H and 175 MHz for 13C, or a Bruker AVANCE III 600 (Bruker Corp., USA) operating at 600 MHz spectrometer for 1H and 150 MHz for 13C. Chemical shift values were referenced to the residual solvent signals for CDCl3 (δH 7.25 and δC 77.2) and conveyed in 6 ppm; multiplicity was showed as: s=singlet, d=doublet, t=triplet and m=multiplet; coupling constants were reported in Hz. HRESIMS data were obtained using Thermo QExactive Plus mass spectrometer (Thermofisher, San Jose, CA, USA) with an electrospray ionization source. The higher energy dissociation (HCD) used a normalized energy of 30 for all the compounds to obtain MS/MS data. Droplet probe analysis for the in situ detection of the biosynthesis of secondary metabolites in fungal cultures was performed using a droplet-LMJ-SSP coupled with a Waters Acquity ultra performance liquid chromatography (UPLC) system (Waters corp.) coupled with a Thermo QE Plus via procedures described previously (Kertesz, V. et al., *Rapid Commun. Mass Spectrom.* 2014, 28, 1553; Kertesz, V., et al., *Anal. Bioanal. Chem.* 2015, 407, 2117; Sica, V. P., et al., *Anal. Methods* 2016, 8, 6143; Sica, V. P., et al., *J. Nat. Prod.* 2015, 78, 1926; Sica, V. P. et al., *J. Ind. Microbiol. Biotechnol.* 2016, 43, 1149; Sica, V. P. et al., *Front. Microbiol.* 2016, 7; Sica, V. P., et al., *Phytochemistry* 2017, 143, 45). Microextractions were performed using a droplet of 1:1 MeOH:H2O. Three different spots were extracted in triplicate by delivering 5 μL of the solvent from a syringe to the surface of the culture then aspiring it back after ~2 sec of interaction to be injected into the UPLC-MS system. The UPLC separation was performed using an Acquity BEH C18 column (50 mm×2.1 mm Id., 1.7 m) equilibrated at 40° C. and a flow rate set at 0.3 mL/min. The mobile phase comprised a linear gradient $CH_3CN$/H2O with 0.1% HCOOH starting at 15% CH3CN to 100% over 8 min. The mobile phase was held for another 1.5 min at 100% CH3CN before going back to the starting conditions. Flash column chromatography was carried out with a Teledyne ISCO combiflash Rf connected to ELSD and PDA detectors with UV detection set at 200-400 nm with a specific wavelength set at 300 nm. The HPLC separation was achieved using Varian ProStar HPLC system connected to a ProStar 335 photodiode array detector (PDA) with UV detection set at 240 nm and 300 nm. Preparative normal phase HPLC purification of samples was performed on a silica (5 m; 250×21.2 mm) column using a flow rate of 21.24 mL/min of a mobile phase consisting of EtOAc and Hexanes. Optical rotation data were acquired on a Rudolph Research Autopol III polarimeter (Rudolph Research Analytical, Flanders, NJ, USA). The UV data were acquired using a Varian Cary 100 Bio UV-Vis spectrometer (Varian Inc., Walnut Creek, CA, USA).

Fungal Strain Identification

Fungal strain MSX59553 from the Mycosynthetix culture collection was utilized in the present study. Strain MSX59553 was isolated by Dr Barry Katz in January 1992 from leaf litter (Figueroa, M., et al., *J. Antibiot.* 2012, 65, 559; Paguigan, N. D., et al., *J. Antibiot.* 2017, 70, 553 ("Paguigan, et al."); Amrine, C. S. M., et al., *J. Ind. Microbiol. Biotechnol.* 2018, 45, 1053 ("Amrine, et al.")). It was identified as *Clonostachys rogersoniana* (Hypocreales, Ascomycota) (Amrine, et al.). The sequence data for this fungal strain have been deposited in GenBank and accession numbers are cited in recent publications (Paguigan, N. D., et al., and Amrine, et al.).

Fermentation, Extraction, and Isolation

To prepare Petri dishes, fungal strain MSX59553 was grown on oatmeal agar (OMA, Difco). A small piece of agar along with mycelium from the growing edge of the colony was transferred onto oatmeal agar that was supplemented with either 5F-DL-Trp, 5F-D-Trp, or 5F-L-Trp (2 mL of filter sterilized 5F-Trp solution that was added to 150 mL of the oatmeal agar after autoclaving). The fungal strain was cultivated on this fluorine supplemented medium for few weeks and transferred two times during its growth onto newly prepared 5F-DL-Trp supplemented oatmeal agar Petri plates, so as to acclimatize the fungal strain to fluorinated building blocks. The same procedure was followed to prepare Petri dishes that contains separately one of the two stereoisomers of Trp separately.

Subsequently, flasks were prepared for the scale up of the site directed biosynthesis experiment, with the aim of isolating the new fluorinated analogues. A small piece of agar along with fungal mycelium grown on the 5F-DL-Trp fluorinated oatmeal agar was added to a YESD broth with 464 ppm of 5F-DL-Trp (660 μL of the 7500 ppm into 10 mL of YESD; 20 g soy peptone, 20 g dextrose, 5 g yeast extract, 1 L H2O). The fungus was grown for a period of 3 days at 23° C. agitated at 100 rpm using an orbital shaker. Fungal colonies grown in YESD broth were transferred into 250 mL Erlenmeyer flasks containing breakfast oatmeal (Old fashion Quaker oats). The oatmeal was prepared by adding 10 g of breakfast oatmeal with 17 mL of DI-H2O and autoclaved at 221° C. for 30 min. An additional 1.2 mL of the 7500 ppm 5F-DL-Trp solution was added to the breakfast oatmeal (495 ppm). The flasks were incubated statically at room temperature for approximately 3 weeks until the cultures showed completion of initial growth phase corresponding to the production of secondary metabolites.

After fermentation, 60 mL of 1:1 MeOH:CHCl3 was added to each growth flask, the culture was chopped using a spatula, and then shaken for 16 h at 100 rpm. The extract was filtrated under vacuum, and 90 mL of CHCl3 and 150 mL of H2O were added to the eluent. The solvents were transferred into a separatory funnel, and the organic layer was drawn off and evaporated in vacuo. This material was reconstituted using 100 mL of 1:1 MeOH:CH3CN and 100 mL of hexanes and then partitioned in a separatory funnel. The MeOH:CH3CN layer was drawn off and evaporated in vacuo. This defatted organic extract (3.9 g) was adsorbed on Celite 545 (Acros Organics) and fractionated via flash chromatography on a 40 g RediSep Rf Gold Si-gel column using a gradient solvent system of hexanes-CHCl3-MeOH at a flow rate of 40 mL/min over 53.3 column volumes (CV) for a duration of 63.9 min. Fractions were collected every 25.0 mL and pooled according to the UV and ELSD profiles, resulting in six fractions (F1-F6). Fraction F2 (750.11 mg) was observed to contain both the targeted masses of verticillins analogues and the high UV signal at 301 nm, which is characteristic of the presence of verticillins. As such, F2 was subjected to a second flash chromatography on three stack 4 g RediSep Rf Gold Si-gel column using a gradient solvent system of hexanes-CHCl3-MeOH at a flow rate of 18 mL/min over 155.0 column volumes (CV) for a duration of 41.3 min. Fractions were collected every 5.0 mL and pooled according to the UV and ELSD profiles, resulting in twelve fractions (F'1-F'12). MS-directed purification showed that fractions F'3, F'5 and F'7 contained both parent and fluorinated analogues of the verticillins. To purify these, fractions F'3, F'5 and F'7 were subjected to preparative normal phase HPLC using Silica column with an isocratic method at 30%, 25%, and 30% of EtOAc, respectively. The separations were performed with a flow rate of 21.24 mL/min over 25, 52 and 54 min for F'3, F'5 and F'7 respectively. This chromatography led to the isolation of compounds 1 (19.3 mg, tR=15.5 min), 4 (2.8 mg, tR=16.7 min) and 9 (0.2 mg, tR=18.5 min) from F'3, compounds 2 (24.8 mg, tR=33.5 min), 5 (2.7 mg, tR=36.2 min), 6 (1.8 mg, tR=41.0 min) and 10 (0.2 mg, tR=46.5 min) from F'5, and compounds 3 (9.3 mg, tR=27.0 min), 7 (1.3 mg, tR=30.5 min) and 8 (0.1 mg, tR=36.5 min) from F'7.

Cytotoxicity Assay

Human melanoma cancer cells (MDA-MB-435), human breast cancer cells (MDA-MB-231) and human ovarian cancer cells (OVCAR3) were obtained from the American Type Culture Collection (Manassas, VA). The cell lines were cultured in RPMI 1640 medium containing fetal 10% bovine serum, 100 unites/mL penicillin and 100 μg/mL streptomycin. The cells were grown at 37° C. under 5% CO2, and then harvested during the log-phase growth by trypsinization followed by two washing to remove all traces of enzymes. Cells were seeded in 96-well clear, flat-bottom plate (Microtest 96, Falcon) at a density of 5000 cells per well. Each plate was incubated overnight at 37° C. under 5% CO2. Samples dissolved in DMSO were diluted and added to the appropriate wells to give final concentrations of 20, 4, 0.8, 0.16, and 0.032 μM for pure compounds, and a total volume of 100 μL and 0.5% DMSO per well. The cells with the test samples were then incubated for 72 h at 37° C. Cell viability was examined using a commercial absorbance assay (CellTiter 96® AQueous One Solution Cell Proliferation Assay, Promega Corp, Madison, WI). IC50 values were determined as the concentration required to diminish cellular growth by 50% compared to the untreated controls after 72 h of continuous exposure. Taxol (Paclitaxel) was used as a positive control.

Results

Fermentation, Extraction, and Isolation

Strain MSX59553 was grown on oatmeal agar (OMA) with a racemic mixture of 5-F-$_{DL}$-Trp (375 ppm, FIG. 5). Those cultures were analyzed in situ via a droplet probe coupled to a UPLC-PDA-HRESIMS-MS/MS system.[26-27] The microextraction of the culture surface (control vs fluorinated medium) displayed characteristic peaks for verticillin H (1) [m/z 725.1345 ([M+H]$^+$)], Sch 52901 (2) [m/z 711.1185 ([M+H]$^+$)], and verticillin A (3) [m/z 697.1030 ([M+H]$^+$)]. In addition, in the medium containing 5-F-$_{DL}$-Trp, several peaks for analogues were detected. The substitution of F into the verticillins increased the molecular ion by 17.99 amu for monofluorination, as noted by m/z 743.1249, 729.1090, and 715.0933, corresponding to the incorporation of a fluorinated Trp unit in the biosynthesis of 1-3, respectively. Additionally, peaks that were shifted by twice 17.99 amu [i.e. m/z 761.1161, 747.0997 and 733.0856] were observed, indicating difluorination into the same three molecules, respectively.

To isolate material for structural characterization and bioassay, the same strain was grown on OMA containing 5-F-$_{DL}$-Trp (375 ppm). This culture was subjected to a couple transfers to the same fluorinated medium, allowing the microorganism to adapt. Then, the strain was cultured on oatmeal, since it was optimal for lab scale production of verticillins.[26] The growth flasks were supplemented with 500 ppm 5-F-$_{DL}$-Trp (FIG. 5), since this concentration was optimal for introducing fluorinated amino acids into peptaibols.[17]

After 28 days fermentation, the HRESIMS data of the organic extract of the culture confirmed incorporation of 5-F-Trp in 1-3 on one or both sides of the dimeric verticillins. Natural product purification yielded seven fluorinated analogues: 9-F-verticillin H (4), 9-F-Sch 52901 (5), 9'-F-Sch 52901 (6), 9-F-verticillin A (7), 9, 9'-diF-verticillin A (8), 9, 9'-diF-verticillin H (9) and 9, 9'-diF-Sch 52901 (10). The monofluorinated analogues were in a ratio of about 1:10 relative to the parents; difluorinated analogues were 1:200.

Compounds 1-10 were purified as light-yellow amorphous powders. The structures of compounds 1-3 were established by favorable comparisons of the HRESIMS and 1D-NMR data to literature.[20a, 20d] The protonated molecular ion [M+H]$^+$ of compounds 4-7 were noted at m/z 743.1231, 729.1071, 729.1064 and 715.0908 respectively. These data corresponded to a gain of 17.99 amu relative to the parents, indicating the replacement of a proton by a fluorine and representing the formulae: $C_{32}H_{31}FN_6O_6S_4$ (4), $C_{31}H_{29}FN_6O_6S_4$ (5), $C_{31}H_{29}FN_6O_6S_4$ (6) and $C_{30}H_{27}FN_6O_6S_4$ (7).

The structures of 4-8 were characterized via 1D and 2D NMR data, including $^{19}F$ NMR spectra. The non-fluorinated parents (i.e. 1 and 3) of 4 and 7, respectively, are symmetrical dimers and became asymmetric via monofluorination (FIG. 2). This was evident in the aromatic region ($\delta_H$ 6.5-8.0 ppm), where H-7, H-7', H-8, H-8', H-10 and H-10' resonated as individual peaks, and the H-9 signal was replaced by fluorine. Compound 2 is asymmetric, and thus monofluorination resulted in two possible analogues (5 and 6), whose aromatic protons exhibited distinct patterns, and as with 4 and 7, proton H-9 (in 5) or H-9' (in 6) were absent.

While in lower abundance, the characterization of the difluorinated analogues followed similar logic. For example, compounds 8-10 with m/z 733.0826, 761.1135 and 747.0983 respectively, demonstrated a gain of 35.99 amu relative to their parents (1-3), corresponding to $C_{30}H_{26}F_2N_6O_6S_4$ (8), $C_{32}H_{30}F_2N_6O_6S_4$ (9) and $C_{31}H_{28}F_2N_6O_6S_4$ (10). In the aromatic region of the $^1$H NMR spectra of 8 and 9 (FIG. 2) symmetry was evident, comparable to 3 and 1, while 10 remained asymmetric. Signals for protons H-9 and H-9' were absent in compounds 8-10 (FIG. 2).

$^{19}$F NMR experiments are beneficial for such studies,[28] and $^1$H-$^{19}$F couplings were supportive of the structural assignments. The $^1$H NMR spectra of compounds 4-7 (FIG. 2) showed resonances for seven aromatic protons in the range of 6.58-7.84 ppm, and three of those were coupled with the fluorine on the same ring system. Difluorinated 8-10 demonstrated only six signals in the aromatic region of the $^1$H NMR spectra with similar J values for $^1$H-$^{19}$F couplings.

The characterization of 4-10 was supported by 2D NMR data (COSY, HSQC and HMBC, FIG. 9-15). The position of fluorine was confirmed by the $^2J_{CH}$ and $^3J_{CH}$ HMBC correlations between the protons on the fluorinated benzene ring and C-9, which was a doublet due to $^{13}$C-$^{19}$F coupling ($\delta_c$ 157.6 ppm, J=235.3-236.9 Hz). As with the $^1$H NMR data, the $^{13}$C NMR spectra displayed a loss of symmetry for 4 and 7. Six carbon doublets were observed in the aromatic region (111.1-157.6 ppm), confirming the incorporation of fluorine. Moreover, in the $^{19}$F NMR experiment, the $\delta_F$ values were in the same range −123.2 to −123.0 ppm with a similar coupling pattern (td), consistent with the pattern observed in the fluorinated building block ($\delta_F$ −124.9 ppm). In addition, $^{19}$F-HMQC data demonstrated a clear correlation of the fluorine with the doublet carbon at C-9 or C-9'. Due to the symmetry in 8 and 9, one peak with a td splitting pattern was observed in the $^{19}$F NMR spectra. Alternatively, 10 showed two overlapping peaks (td) at −122.9 ppm due to asymmetry. Importantly, the HMBC data showed a $^3J_{CH}$ correlation between the aromatic proton H-7 and the doublet carbon peak at $\delta_c$~158 ppm in 8-10.

HRESIMS/MS experiments were used to distinguish between the incorporation of the fluorine into 5 vs 6, since those compounds were asymmetric. The fragmentation of these resulted in m/z 380.0555 and m/z 348.0452 for 5, and m/z 362.0608 and 366.0388 for 6, as predicted.

Figure 16:
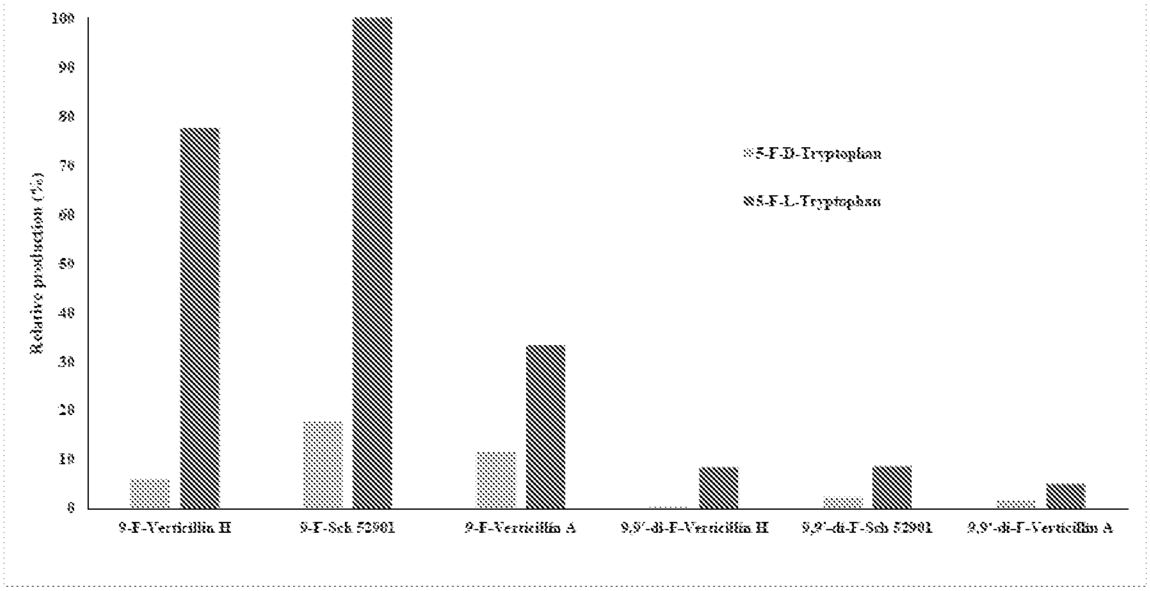
FIG. 16 is a bar graph showing relative production of fluorinated verticillin analogues via UPLC-HRMS analysis of extracted Petri dishes used previously for the droplet probe analysis. The in-situ extraction observed a detection of the expected masses of the fluorinated verticillin analogues in both 5-F-D-Trp and 5-F-L-Trp supplemented media. The relative percentages were normalized by multiplying the peak areas by the weight of their corresponding organic extracts. The results demonstrate that the 5-F-L-Trp was the building block that was preferably incorporated in the total production of the fluorinated verticillin analogues.
Figure 17:
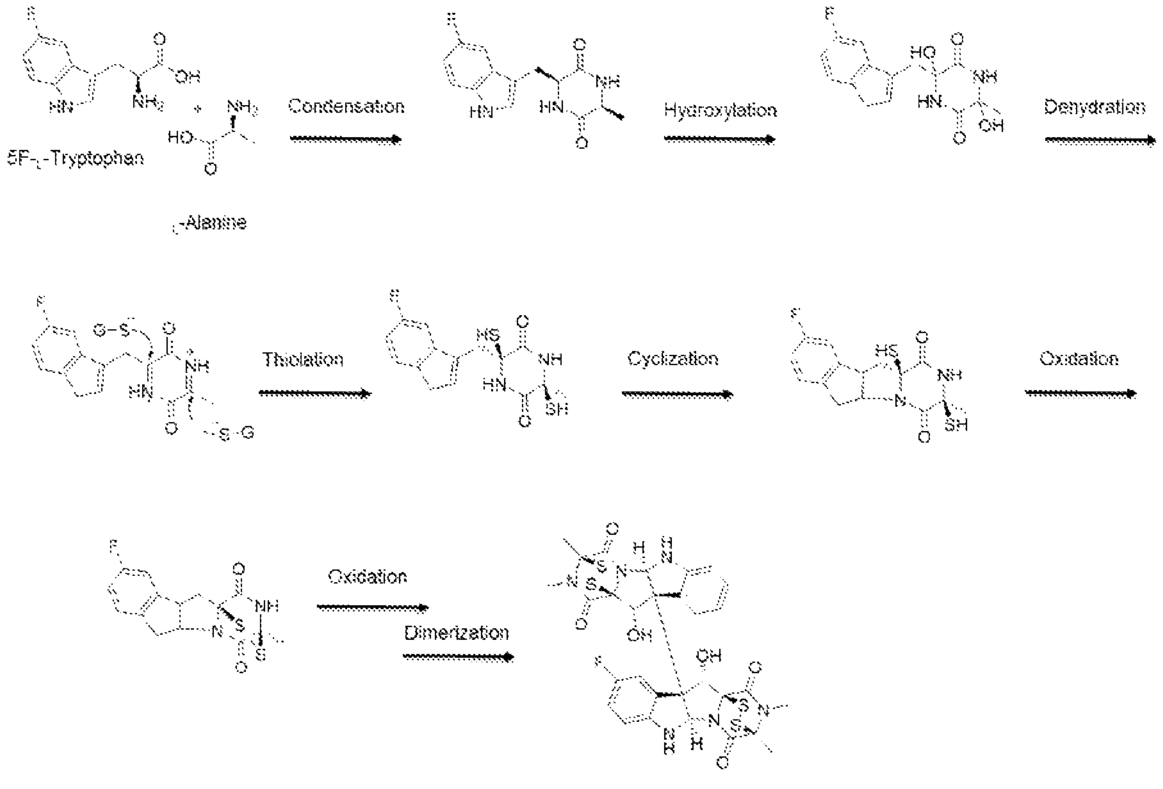
FIG. 17 is a scheme for the proposed biosynthetic pathway for 9-F-Verticillin A.
Figure 18:
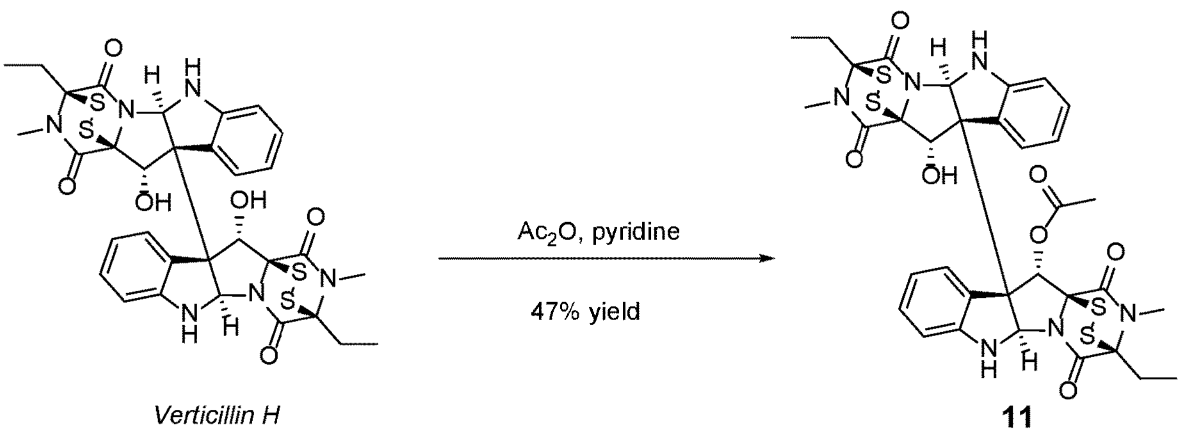
FIG. 18 is a scheme for the semi-synthesis of vertH-1 (11).
Figure 19:
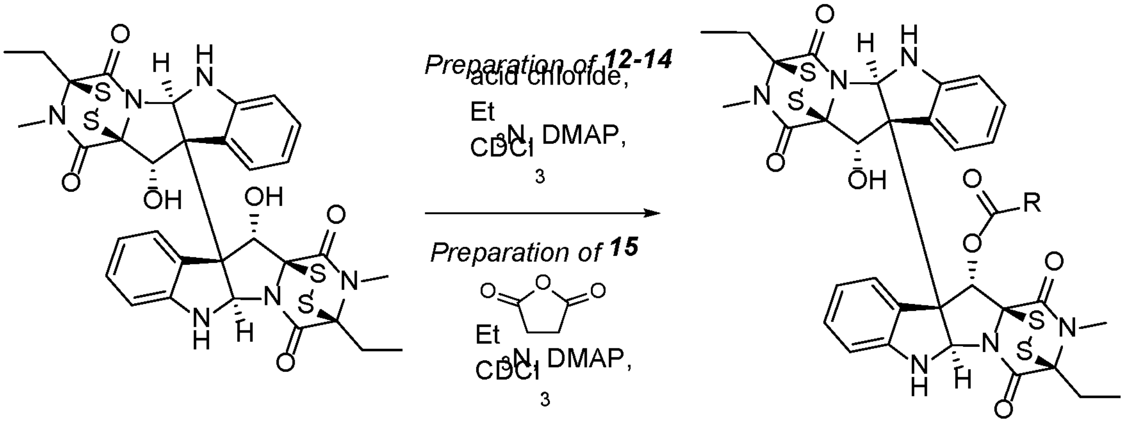
FIG. 19 is a scheme for the semi-synthesis of ester derivatives 12-14.
Figure 21:
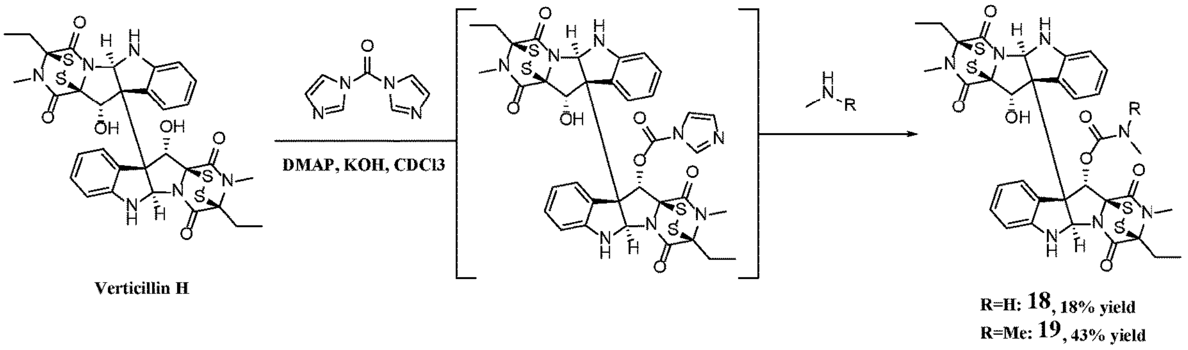
FIG. 21 is a scheme for the semi-synthesis of carbamate derivatives 18 and 19.
Figure 24:
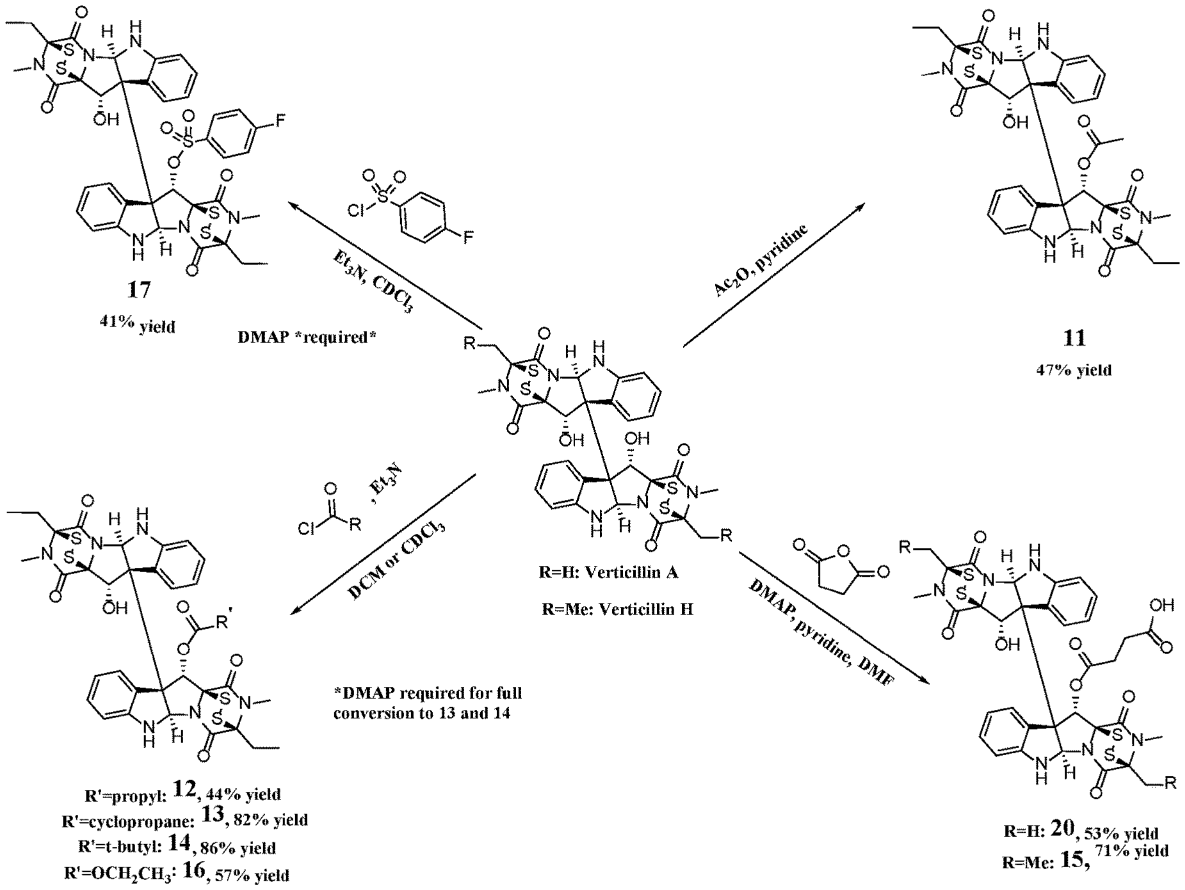
FIG. 24 is a synthetic scheme of compounds 11-17, and 20.
Figure 25:
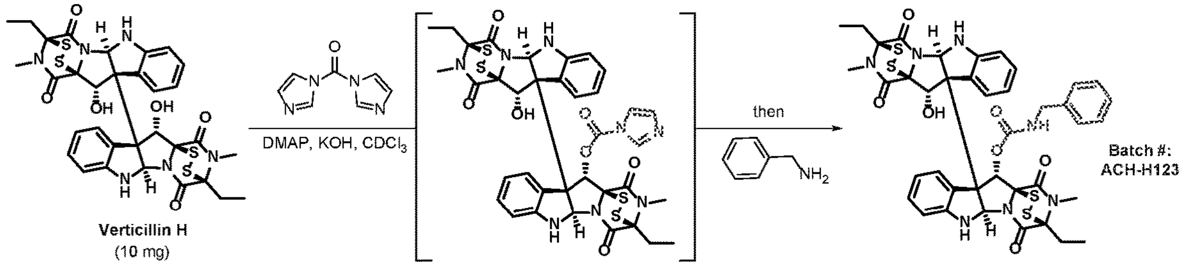
FIG. 25 is a synthetic scheme of VertH-10.

The NRPS pathway is characterized by the presence of epimerization domains to catalyze the conversion of L amino acids into D amino acids and vice versa,[29] suggesting the possible incorporation of both 5-F-Trp enantiomers. The proposed biosynthesis of diketopiperazine rings in gliotoxin,[30] and a study of acetylaranotin,[31] shows that the configuration at the α carbon of Trp is lost via hydroxylation followed by dehydration (FIG. 17). To test this, two biological replicates were analyzed using 5-F-D-Trp, 5-F-L-Trp or 5-F-DL-Trp doped separately into OMA media, along with a control. In situ analysis via droplet probe demonstrated signals for 1-3 in the control, and in all three fluorination experiments, signals for 1-10 were observed. Mutually supportive data was noted by traditional natural products extraction of the same plates via measuring relative peak areas of 1-10 (FIG. 16). The highest incorporations were observed with 5-F-L-Trp.[17]

9-F-Verticillin H (4). Light yellow powder, $[\alpha]_{D26}$+567 (c 0.3, $CHCl_3$); UV (MeOH) λmax (log ε) 223 (3.22) nm, 309 (2.90) nm; $_1$H NMR ($CDCl_3$, 700 MHz) δ=1.22 (t, J=7.2 Hz, 3H), 1.25 (t, J=7.2 Hz, 3H), 2.17 (m, 2H), 2.38 (m, 2H), 3.02 (s, 3H), 3.03 (s, 3H), 5.05 (s, 1H), 5.14 (s, 1H), 5.15 (s, 1H), 5.16 (s, 1H), 5.59 (s, 1H), 5.64 (s, 1H), 5.68 (s, 1H), 5.70 (s, 1H), 6.58 (dd, J=8.6 Hz, 4.4 Hz, 1H), 6.65 (dd, J=7.6 Hz, 1.0 Hz, 1H), 6.83 (td, =7.6 Hz, 1.0 Hz, 1H), 6.86 (td, J=8.6 Hz, 2.7 Hz, 1H), 7.15 (td, J=7.6 Hz, 1.2 Hz, 1H), 7.63 (dd, J=9.4 Hz, 2.7 Hz, 1H), 7.83 (dd, J=7.6 Hz, 1.2 Hz, 1H); 13C NMR (CDCl3, 175 MHz), δ=9.8, 9.9, 24.5, 24.6, 28.0, 65.5, 65.9 (d, J=1.9 Hz), 76.6, 76.7, 77.4, 77.5, 81.9, 82.0, 83.0, 83.8, 110.8, 111.1 (d, J=8.5 Hz), 115.5 (d, J=25.4 Hz), 116.6 (d, J=24.5 Hz), 120.5, 128.2, 128.9, 130.1, 130.8 (d, J=8.5 Hz), 144.9 (d, J=1.3 Hz), 148.8, 157.6 (d, J=235.6 Hz), 161.4, 167.1 HRESIMS m/z 743.1231 $[M+H]^+$ (calcd for C32H32F1N6O6S4, m/z 743.1245).

Figure 10:
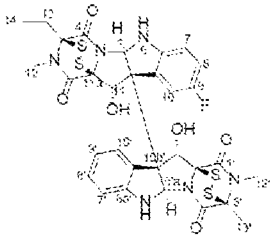
FIG. 10 is a table showing the $^{1}$H, $^{13}$C and HMBC NMR data for 9-F-Sch 52901 (5) in $CDCl_3$ [700 MHz for $^{1}$H and 175 MHz for $^{13}$C].

9-F-Sch 52901 (5). Light yellow powder, [α]D26+595 (c 0.2, CHCl3); UV (MeOH) λmax (log ε) 242 (3.67) nm, 310 (3.56) nm; 1H NMR (CDCl3, 700 MHz) δ=1.22 (t, J=7.2 Hz, 3H), 1.90 (s, 3H), 2.17 (m, 2H), 2.37 (m, 2H), 3.01 (s, 3H), 3.02 (s, 3H), 5.05 (s, 1H), 5.10 (s, 1H), 5.13 (s, 1H), 5.15 (s, 1H), 5.59 (s, 1H), 5.67 (s, 1H), 5.70 (s, 1H), 5.74 (s, 1H), 6.58 (dd, J=8.6 Hz, 4.4 Hz 1H), 6.66 (dd, J=7.7 Hz, 1.0 Hz, 1H), 6.84 (td, J=7.7 Hz, 1.0 Hz, 1H), 6.86 (td, J=8.6 Hz, 2.7 Hz, 1H), 7.15 (td, J=7.7 Hz, 1.2 Hz, 1H), 7.61 (dd, J=9.4 Hz, 2.7 Hz, 1H), 7.84 (dd, J=7.7 Hz, 1.2 Hz, 1H); 13C NMR (CDCl3, 175 MHz), δ=9.8, 17.5, 24.5, 27.2, 28.0, 65.6, 65.9 (d, J=1.9 Hz), 72.9, 76.4, 76.6, 77.5, 81.9, 82.0, 82.8, 83.7, 110.8, 111.1 (d, J=8.5 Hz), 115.5 (d, J=25.7 Hz), 116.6 (d, J=23.6 Hz), 120.5, 128.3, 128.9, 130.2, 130.8 (d, J=8.6 Hz), 144.9 (d, J=1.1 Hz), 148.7, 157.6 (d, J=236.3 Hz), 161.4, 162.3, 166.1, 167.1 (FIG. 10); HRESIMS m/z 729.1071 $[M+H]^+$ (calcd for C31H30F1N6O6S4, m/z 729.1088).

Figure 11:
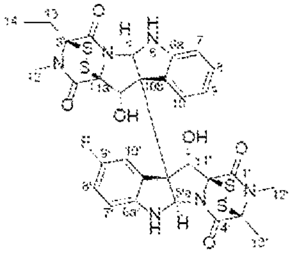
FIG. 11 is a table showing the $^{1}$H, $^{13}$C and HMBC NMR data for 9'-F-Sch 52901 (6) in $CDCl_3$ [700 MHz for $^{1}$H and 175 MHz for $^{13}$C].

9'-F-Sch 52901 (6). Light yellow powder, [α]D26+543 (c 0.21, CHCl3); UV (MeOH) λmax (log ε) 236 (3.58) nm, 309 (3.41) nm; 1H NMR (CDCl3, 700 MHz) δ=1.25 (t, J=7.2 Hz, 3H), 1.89 (s, 3H), 2.18 (m, 2H), 2.39 (m, 2H), 2.99 (s, 3H), 3.03 (s, 3H), 4.99 (s, 1H), 5.13 (s, 1H), 5.15 (s, 2H), 5.63 (s, 1H), 5.68 (s, 1H), 5.70 (s, 2H), 6.58 (dd, J=8.6 Hz, 4.4 Hz, 1H), 6.65 (dd, J=7.7 Hz, 1.0 Hz, 1H), 6.81 (td, J=7.7 Hz, 1.0 Hz, 1H), 6.87 (td, J=2.7 Hz, 8.6 Hz, 1H), 7.13 (td, J=7.7 Hz, 1.3 Hz, 1H), 7.64 (dd, J=9.4 Hz, 2.7 Hz, 1H), 7.81 (dd, J=7.7 Hz, 1.3 Hz, 1H); 13C NMR (CDCl3, 175 MHz), δ=9.8, 17.5, 24.6, 27.2, 28.0, 65.6, 66.0 (d, J=1.9 Hz), 73.0, 76.3, 76.7, 77.4, 81.9, 82.0, 83.0, 83.6, 110.8, 111.2 (d, J=8.5 Hz), 115.6 (d, J=25.5 Hz), 116.6 (d, J=23.8 Hz), 120.5, 128.2, 128.9, 130.1, 130.8 (d, J=8.6 Hz), 144.8 (d, J=1.4 Hz), 148.7, 157.6 (d, J=236.0 Hz), 161.4, 162.3, 166.1, 167.1 (FIG. 11); HRESIMS m/z 729.1064 [M+H]+ (calcd for C31H30F1N6O6S4, m/z 729.1088).

Figure 12:
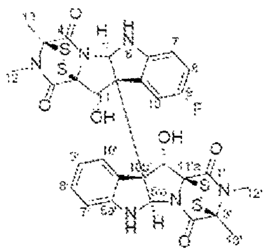
FIG. 12 is a table showing the $^{1}$H, $^{13}$C and HMBC NMR data for 9-F-verticillin A (7) in $CDCl_3$ [700 MHz for $^{1}$H and 175 MHz for $^{13}$C].

9-F-Verticillin A (7). Light yellow powder, [α]D26+700 (c 0.13, CHCl3); UV (MeOH) λmax (log ε) 239 (3.90) nm, 309 (3.43) nm; 1H NMR (CDCl3, 500 MHz) δ=1.88 (s, 3H), 1.90 (s, 3H), 2.99 (s, 3H), 3.01 (s, 3H), 4.99 (s, 1H), 5.10 (s, 1H), 5.12 (s, 1H), 5.14 (s, 1H), 5.67 (s, 1H), 5.69 (s, 2H), 5.73 (s, 1H), 6.58 (dd, J=8.6 Hz, 4.4, 1H), 6.65 (dd, J=7.7 Hz, 1.0 Hz, 1H), 6.82 (td, J=J=7.7 Hz, 1.0 Hz, 1H), 6.86 (td, J=8.6 Hz, 2.7 Hz, 1H), 7.14 (td, J=7.7 Hz, 0.9 Hz, 1H), 7.61 (dd, J=9.4 Hz, 2.7 Hz, 1H), 7.82 (dd, J=7.7 Hz, 0.9 Hz, 1H); 13C NMR (CDCl3, 175 MHz), δ=17.4, 27.18, 27.2, 65.7, 66.0 (d, J=1.6 Hz), 72.9, 73.0, 76.3, 76.4, 81.9, 82.0, 82.8, 83.6, 110.8, 111.2 (d, J=8.6 Hz), 115.5 (d, J=25.5 Hz), 116.6 (d, J=24.7 Hz), 120.5, 128.2, 128.9, 130.1, 130.8 (d, J=8.6 Hz), 144.8 (d, J=1.2 Hz), 148.6, 157.6 (d, J=236.2 Hz), 162.2, 162.3, 166.1 (FIG. 12); HRESIMS m/z 715.0908 [M+H]+ (calcd for C30H28F1N6O6S4, m/z 715.0932).

Figure 13:
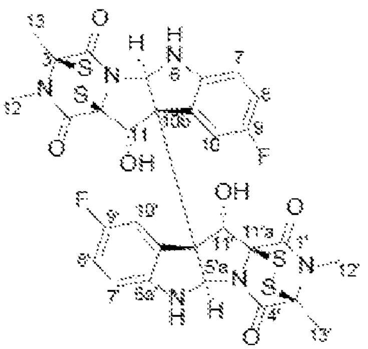
FIG. 13 is a table showing the $^{1}$H (700 MHz), $^{13}$C (175 MHz) and HMBC NMR data for 9, 9'-di F-verticillin A

9, 9'-diF-Verticillin A (8). Light yellow powder, [α]D26+400 (c 0.14, CHCl3); UV (MeOH) λmax (log ε) 239 (3.66) nm, 315 (3.50) nm; 1H NMR (CDCl3, 700 MHz) δ=1.91 (s, 6H), 3.01 (s, 6H), 5.01 (s, 2H), 5.13 (s, 2H), 5.65 (s, 2H), 5.76 (s, 2H), 6.59 (dd, J=8.6 Hz, 4.4 Hz, 2H), 6.86 (td, J=8.6 Hz, 2.7 Hz, 2H), 7.60 (dd, J=9.4 Hz, 2.7 Hz, 2H); 13C NMR (CDCl3, 175 MHz), δ=17.5, 27.2, 65.8 (d, J=1.6 Hz), 73.0, 76.2, 81.9, 83.4, 111.3 (d, J=8.3 Hz), 115.6 (d, J=26.6 Hz), 116.7 (d, J=23.9 Hz), 130.4 (d, J=8.7 Hz), 144.8, 157.6 (d, J=236.9 Hz), 162.3, 166.0 (FIG. 13); HRESIMS m/z 733.0826 [M+H]+ (calcd for $C_{30}H_{27}F_2N_6O_6S_4$, m/z 733.0837).

Figure 14:
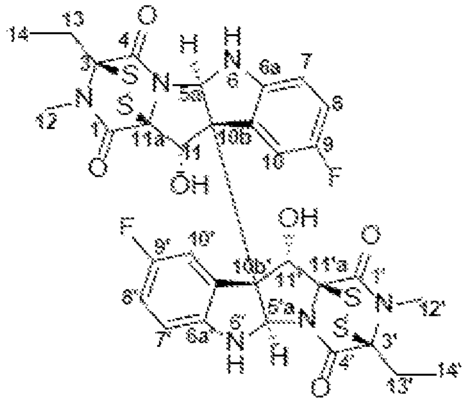
FIG. 14 is a table showing the $^{1}$H and HMBC NMR data for 9,9'-di F-verticillin H (9) in $CDCl_3$ [500 MHz].

9, 9'-diF-Verticillin H (9). Light yellow powder, [α]D26+1360 (c 0.1, CHCl3); UV (MeOH) λmax (log ε) 234 (3.21) nm, 309 (2.95) nm; 1H NMR (CDCl3, 500 MHz) δ=1.26 (t, J=7.1 Hz, 6H), 2.19 (m, 1H), 2.39 (m, 1H), 3.04 (s, 6H), 5.07 (s, 2H), 5.15 (s, 2H), 5.66 (s, 4H), 6.59 (dd, J=8.6 Hz, 4.4 Hz, 2H), 6.88 (td, J=8.6 Hz, 2.6 Hz, 2H), 7.60 (dd, J=9.4 Hz, 2.6 Hz, 2H); (FIG. 14); HRESIMS m/z 761.1135 [M+H]+ (calcd for $C_{32}H_{31}F_2N_6O_6S_4$, m/z 761.1150).

Figure 15:
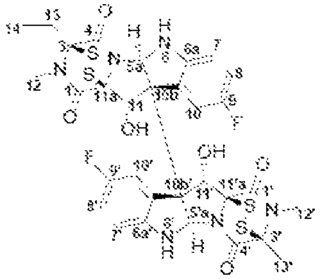
FIG. 15 is a table showing the $^{1}$H and HMBC NMR data for 9,9'-di F-Sch 52901 (10) in $CDCl_3$ [500 MHz].

9, 9'-diF-Sch 52901 (10). Light yellow powder, [α]D26+1890 (c 0.1, CHCl3); UV (MeOH) λmax (log ε) 226 (3.23) nm, 315 (2.97) nm; 1H NMR (CDCl3, 500 MHz) δ=1.26 (t, J=7.0 Hz, 3H), 1.91 (s, 3H), 2.19 (m, 1H), 2.39 (m, 1H), 3.02 (s, 3H), 3.04 (s, 3H), 5.05 (s, 1H), 5.07 (s, 1H), 5.14 (s, 1H), 5.15 (s, 1H), 5.66 (s, 3H), 5.77 (s, 1H), 6.59 (m, J=8.8 Hz, 4.4 Hz, 2H), 6.86 (td, J=8.8 Hz, 2.8 Hz, 1H), 6.88 (td, J=8.8 Hz, 2.8 Hz, 1H), 7.61 (m, J=9.4 Hz, 2.8 Hz, 1H), 7.63 (m, J=9.4 Hz, 2.8 Hz, 1H); (FIG. 15); HRESIMS m/z 747.0983 [M+H]+ (calcd for $C_{31}H_{29}F_2N_6O_6S_4$, m/z 747.0994).

Cytotoxicity Assay

The cytotoxicity of 1-10 was assessed against three cell lines: melanoma (MDA-MB-435), breast (MDA-MB-231) and ovarian (OVCAR3) cancers.[20d, 32] The fluorinated analogues were equipotent to the parent compounds, with $IC_{50}$'s ranging from 30 to 900 nM (FIG. 4). This indicated that fluorination did not negatively impact cytotoxicity.

This the first study using a precursor-directed biosynthetic approach to generate analogues of verticillins, including the first report of fluorination in any manner. Importantly, these compounds displayed nanomolar cytotoxicity in vitro. As observed via in situ monitoring of the fungal cultures, the incorporation of 5-F-L-Trp was higher than 5-F-D-Trp, but a racemic mixture was used for cost effectiveness and because the configuration at the α carbon was likely ablated during biosynthesis.

REFERENCES 1. (a) Yamazaki, T.; Taguchi, T., Ojima, I. Eds.: Ojima, I., Ed.; John Wiley & Sons: Wiltshire Great Britain, 2009; p 3. (b) O'Hagan, D., Deng, H., *Chem. Rev.* 2015, 115, 634.
2. Boland, E. W., *Ann. N. Y. Acad. Sci.* 1959, 82, 887.
3. (a) Cohen, S. S.; Flaks, J. G.; Barner, H. D.; Loeb, M. R., Lichtenstein, J., Proc. *Natl. Acad Sci.* 1958, 44, 1004. (b) Duschinsky, R.; Pleven, E., Heidelberger, C., *J. Am. Chem. Soc.* 1957, 79, 4559.
4. Gillis, E. P.; Eastman, K. J.; Hill, M. D.; Donnelly, D. J., Meanwell, N. A., *J. Med Chem.* 2015, 58, 8315.
5. (a) Purser, S.; Moore, P. R.; Swallow, S., Gouverneur, V., *Chem. Soc. Rev.* 2008, 37, 320. (b) Müller, K.; Faeh, C., Diederich, F., *Science* 2007, 317, 1881. (c) Meanwell, N. A., *J. Med Chem.* 2018, 61, 5822.
6. Wang, J.; Sánchez-Roselló, M.; Aceña, J. L.; del Pozo, C.; Sorochinsky, A. E.; Fustero, S.; Soloshonok, V. A., Liu, H., *Chem. Rev.* 2014, 114, 2432.
7. Wong, D. T.; Perry, K. W., Bymaster, F. P., *Nat. Rev. Drug Discovery* 2005, 4, 764.
8. (a) Chin, N.-X., Neu, H. C., Antimicrob. Agents Chemother. 1984, 25, 319. (b) Sharma, P. C.; Jain, A.; Jain, S.; Pahwa, R., Yar, M. S., *J. Enzyme Inhib. Med Chem.* 2010, 25, 577.
9. Kim, D.; Wang, L.; Beconi, M.; Eiermann, G. J.; Fisher, M. H.; He, H.; Hickey, G. J.; Kowalchick, J. E.; Leiting, B.; Lyons, K.; Marsilio, F.; McCann, M. E.; Patel, R. A.; Petrov, A.; Scapin, G.; Patel, S. B.; Roy, R. S.; Wu, J. K.; Wyvratt, M. J.; Zhang, B. B.; Zhu, L.; Thornberry, N. A., Weber, A. E., *J. Med. Chem.* 2005, 48, 141.
10. Zhou, Y.; Wang, J.; Gu, Z.; Wang, S.; Zhu, W.; Aceña, J. L.; Soloshonok, V. A.; Izawa, K., Liu, H., *Chem. Rev.* 2016, 116, 422.
11. Kirk, K. L., *Org. Process Res. Dev.* 2008, 12, 305.
12. (a) Romanov-Michailidis, F.; Guenee, L., Alexakis, A., *Angew. Chem.* 2013, 125, 9436. (b) Halperin, S. D.; Kwon, D.; Holmes, M.; Regalado, E. L.; Campeau, L.-C.; DiRocco, D. A., Britton, R., *Org. Lett.* 2015, 17, 5200.
13. Walker, M. C., Chang, M. C., *Chem. Soc. Rev.* 2014, 43, 6527.
14. (a) Nilanonta, C.; Isaka, M.; Kittakoop, P.; Trakulnaleamsai, S.; Tanticharoen, M., Thebtaranonth, Y., *Tetrahedron* 2002, 58, 3355. (b) Thiericke, R., Rohr, J., *Nat. Prod. Rep.* 1993, 10, 265.
15. Xu, Y.; Zhan, J.; Wijeratne, E. K.; Burns, A. M.; Gunatilaka, A. L., Molnár, I., *J. Nat. Prod.* 2007, 70, 1467.
16. (a) Saverino, D.; Debbia, E. A.; Pesce, A.; Lepore, A. M., Schito, G. C., *J. Antimicrob. Chemother.* 1992, 30, 261. (b) Toscano, L.; Fioriello, G.; Spagnoli, R.; Cappelletti, L., Zanuso, G., *J. Antibiot.* 1983, 36, 1439.
17. Rivera-Chávez, J.; Raja, H. A.; Graf, T. N.; Burdette, J. E.; Pearce, C. J., Oberlies, N. H., *J. Nat. Prod.* 2017, 80, 1883.
18. Gardiner, D. M.; Waring, P., Howlett, B. J., *Microbiology* 2005, 151, 1021.
19. Katagiri, K.; Sato, K.; Hayakawa, S.; Matsushima, T., Minato, H., *J. Antibiot.* 1970, 23, 420.
20. (a) Chu, M.; Truumees, I.; Rothofsky, M. L.; Patel, M. G.; Gentile, F.; Das, P. R., Puar, M. S., J. Antibiot. 1995, 48, 1440. (b) Jordan, T. W., Cordiner, S. J., *Trends Pharmacol. Sci.* 1987, 8, 144. (c) Zhang, Y.; Chen, Y.; Guo, X.; Zhang, X.; Zhao, W.; Zhong, L.; Zhou, J.; Xi, Y.; Lin, Z., Ding, J., *Anti-Cancer Drugs* 2005, 16, 515. (d) Figueroa, M.; Graf, T. N.; Ayers, S.; Adcock, A. F.; Kroll, D. J.; Yang, J.; Swanson, S. M.; Munoz-Acuna, U.; Carcache de Blanco, E. J.; Agrawal, R.; Wani, M. C.; Darveaux, B. A.; Pearce, C. J., Oberlies, N. H., *J. Antibiot.* 2012, 65, 559.
21. Paschall, A. V.; Yang, D.; Lu, C.; Choi, J.-H.; Li, X.; Liu, F.; Figueroa, M.; Oberlies, N. H.; Pearce, C.; Bollag, W. B.; Nayak-Kapoor, A., Liu, K., *J. Immunol.* 2015, 195, 1868.
22. Lu, C.; Paschall, A. V.; Shi, H.; Savage, N.; Waller, J. L.; Sabbatini, M. E.; Oberlies, N. H.; Pearce, C., Liu, K., *J. Natl. Cancer Inst.* 2017, 109, djw283.
23. (a) Kim, J., Movassaghi, M., *Acc. Chem. Res.* 2015, 48, 1159. (b) Kim, J.; Ashenhurst, J. A., Movassaghi, M., *Science* 2009, 324, 238.
24. Boyer, N.; Morrison, K. C.; Kim, J.; Hergenrother, P. J., Movassaghi, M., *Chem. Sci.* 2013, 4, 1646.
25. (a) Fox, E. M., Howlett, B. J., *Mycol. Res.* 2008, 112, 162. (b) Süssmuth, R. D., Mainz, A., *Angew. Chem. Int. Ed* 2017, 56, 3770.
26. Amrine, C. S. M.; Raja, H. A.; Darveaux, B. A.; Pearce, C. J., Oberlies, N. H., *J. Ind. Microbiol. Biotechnol.* 2018, 45, 1053.
27. (a) Sica, V. P.; Figueroa, M.; Raja, H. A.; El-Elimat, T.; Darveaux, B. A.; Pearce, C. J., Oberlies, N. H., *J. Ind. Microbiol. Biotechnol.* 2016, 43, 1149. (b) Sica, V. P.; Rees, E. R.; Tchegnon, E.; Bardsley, R. H.; Raja, H. A., Oberlies, N. H., *Front. Microbiol.* 2016, 7, DOI: 10.3389/fmicb.2016.00544. (c) Kertesz, V., Berkel, G. J. V., *Rapid Commun. Mass Spectrom.* 2014, 28, 1553. (d) Sica, V. P.;

Raja, H. A.; El-Elimat, T.; Kertesz, V.; Van Berkel, G. J.; Pearce, C. J., Oberlies, N. H., *J. Nat. Prod.* 2015, 78, 1926.

28. McAlpine, J. B.; Chen, S.-N.; Kutateladze, A.; MacMillan, J. B.; Appendino, G.; Barison, A.; Beniddir, M. A.; Biavatti, M. W.; Bluml, S.; Boufridi, A.; Butler, M. S.; Capon, R. J.; Choi, Y. H.; Coppage, D.; Crews, P.; Crimmins, M. T.; Csete, M.; Dewapriya, P.; Egan, J. M.; Garson, M. J.; Genta-Jouve, G.; Gerwick, W. H.; Gross, H.; Harper, M. K.; Hermanto, P.; Hook, J. M.; Hunter, L.; Jeannerat, D.; Ji, N.-Y.; Johnson, T. A.; Kingston, D. G. I.; Koshino, H.; Lee, H.-W.; Lewin, G.; Li, J.; Linington, R. G.; Liu, M.; McPhail, K. L.; Molinski, T. F.; Moore, B. S.; Nam, J.-W.; Neupane, R. P.; Niemitz, M.; Nuzillard, J.-M.; Oberlies, N. H.; Ocampos, F. M. M.; Pan, G.; Quinn, R. J.; Reddy, D. S.; Renault, J.-H.; Rivera-Chávez, J.; Robien, W.; Saunders, C. M.; Schmidt, T. J.; Seger, C.; Shen, B.; Steinbeck, C.; Stuppner, H.; Sturm, S.; Taglialatela-Scafati, O.; Tantillo, D. J.; Verpoorte, R.; Wang, B.-G.; Williams, C. M.; Williams, P. G.; Wist, J.; Yue, J.-M.; Zhang, C.; Xu, Z.; Simmler, C.; Lankin, D. C.; Bisson, J., Pauli, G. F., *Nat. Prod. Rep.* 2019, DOI: 10.1039/C8NP90041H.
29. (a) Kim, W. E.; Patel, A.; Hur, G. H.; Tufar, P.; Wuo, M. G.; McCammon, J. A., Burkart, M. D., *ChemBioChem* 2019, 20, 147. (b) Tanner, M. E., *Acc. Chem. Res.* 2002, 35, 237.
30. Gu, B.; He, S.; Yan, X., Zhang, L., *Appl. Microbiol. Biotechnol.* 2013, 97, 8439.
31. Guo, C.-J.; Yeh, H.-H.; Chiang, Y.-M.; Sanchez, J. F.; Chang, S.-L.; Bruno, K. S., Wang, C. C. C., *J. Am. Chem. Soc.* 2013, 135, 7205.
32. (a) El-Elimat, T.; Figueroa, M.; Raja, H. A.; Graf, T. N.; Swanson, S. M.; Falkinham III, J. O.; Wani, M. C.; Pearce, C. J., Oberlies, N. H., *Eur. J. Org. Chem* 2015, 2015, 109. (b) El-Elimat, T.; Raja, H. A.; Day, C. S.; Chen, W.-L.; Swanson, S. M., Oberlies, N. H., *J. Nat. Prod.* 2014, 77, 2088.
33. Harrison, C., *Nat. Biotechnol.* 2014, 32, 403.

Example 2. Acetylation of Epipolythiodioxopiperazine Alkaloids (Verticillins)

The verticillins are a class of epipolythiodioxopiperazine alkaloids (ETP) that recently attracted attention due to their potent anticancer activity and recently elucidated mechanism of action. While there are about 20 verticillin analogues in the literature, all are isolated natural products. This study took a semi-synthetic approach toward the generation of analogues, using isolated natural products as the starting materials. Verticillin H (1) and verticillin A (3) were used to form the core of nine analogues of the former (11-19) and one analogue of the latter (20). The synthetic reactions were monitored via $^1$H NMR. The synthesized compounds and their corresponding starting materials were screened for activity against a panel of cancer cell lines; MDA-MB-435, MDA-MB-231, and OVCAR3. Compounds 12, 14, and 16 showed more potent $IC_{50}$ values in comparison with 1. In addition to potency, the solubility of the analogues was improved relative to the natural product parents.

Background

In 2019, it is estimated that over 1.7 million cases of cancer will be diagnosed in the United States alone. Moreover, cancer is predicted to result in over 600 thousand deaths, making it the second leading cause of death in the country.[1] Despite significant advances in both the detection and treatment of the disease made over the course of the last four decades, some types of cancer, such as triple negative breast cancer and ovarian cancer, are still extremely difficult to treat effectively.[2] With this in mind, there is still a need for new drug discovery and development efforts to tackle this problem. One possible method to address this need is to consider known compounds that have shown promising anticancer activity, but for one reason or another have also faced challenges in overcoming the hurdles associated with modern drug development.

From a historical perspective, the origins of over 60% of the current FDA approved anticancer drugs can be traced back to natural products.[3, 4] What may be less obvious from that statistic and an understanding of the utility of natural products themselves is that a staggering 40% of the approved small-molecule drugs to reach the market between 1981 and 2014, including 22% of new anticancer agents, are actually structural derivatives of those natural compounds, including primarily semi-synthetic derivatives of the natural leads.[5] The value of these semi-synthetic analogues[6, 7] lies in their ability to retain the privileged scaffolds afforded by nature, complete with their complex ring architectures and stereochemical diversity.[8, 9] Exploiting these naturally engineered scaffolds frequently expedites the study of structure-activity relationships[10-12] and has the potential to facilitate more rapid drug development by improving drug properties including solubility, overcoming challenges like drug resistance,[13] and supplying material on larger scales.[14-17] Examples of semisynthetic analogues that have gained FDA approval for cancer therapy, including taxotere,[18, 19] ixabepilone,[20-22] and the camptothecin derivatives irinotecan (also known as CPT-11)[23, 24] and topotecan,[17, 25, 26] serve as both validation and inspiration for the application of semisynthetic approaches to other highly potent natural compounds.

The verticillins, fungal metabolites and key members of the epipolythiodioxopiperazine alkaloids (ETP)[27-29] isolated from cultures of the *Verticillium* sp., *Penicillium* sp., and *Gliocladium* sp.,[30] for example, represent an attractive class of compounds for the application of this strategy. These intricate natural compounds are characterized by their dimeric pyrroloindoline cores, cis-fused five membered rings, and the sulfur bridges across their diketopiperizine rings.[31] Verticillin A, the parent compound and arguably the most widely studied of the class, was first isolated in 1970. Although this compound has shown very promising in vitro and in vivo activity against a variety of cancer cell lines, the relatively low availability of the compound through culture from natural sources has hampered its development. Over the past decade, however, interest in verticillin A and related compounds has increased dramatically both from a biological and chemical perspective. In fact, the creative efforts of Movassaghi and others have recently established elegant total syntheses of (+)-11,11'-dideoxyverticillin A and a number of related compounds including (+)-gliocladin C, (+)-chaetocin, and bionectin. These syntheses, however, are clearly not trivial and, despite their efforts, the production of the quantities of material necessary for thorough biological evaluation via synthetic means remains a significant challenge. Adding to this challenge is the potential need for subsequent structural modification and optimization to explore structure-activity relationships and overcome limitations associated with their drug properties, particularly their poor solubility, potentially increasing the complexity of these efforts. This has led to methods to more efficiently increase the production of various members of the verticillin class[32]. With quantities of these compounds in hand, semi-synthesis has ultimately become an option to further explore the unique properties of these compounds.

Materials and Methods

All solvents were obtained from Fisher Scientific. NMR data were collected in $CDCl_3$ using either a JEOL ECS-400 spectrometer (JEOL USA, Inc.) operating at 400 MHz for $^1H$ and 100 MHz for $^{13}C$, or JEOL ECA-500 NMR spectrometer (JEOL USA, Inc.) operating at 500 MHz for $^1H$, 470 MHz for $^{19}F$ and 125 MHz for $^{13}C$, or an Agilent 700 MHz NMR spectrometer (Agilent technologies, Inc., Santa Clara, CA, USA) operating at 700 MHz for $^1H$ and 175 MHz for $^{13}C$. Chemical shift values were referenced to the residual solvent signals for $CDCl_3$ ($\delta_H$ 7.25 and $\delta_C$ 77.2) and reported in 6 ppm; multiplicity was showed as: s=singlet, d=doublet, t=triplet, q=quartet and m=multiplet; coupling constants were conveyed in Hz. Thermo QExactive Plus mass spectrometer (Thermofisher, San Jose, CA, USA) with an electrospray ionization source was utilized to collect HRESIMS data. The UPLC separation was achieved using an Acquity BEH Cis column (50 mm×2.1 mm I.d., 1.7 μm) equilibrated at 40° C. and a flow rate set at 0.3 mL/min. The mobile phase comprised a linear gradient $CH_3CN/H_2O$ with 0.1% HCOOH starting at 15% $CH_3CN$ to 100% over 8.5 min. Flash column chromatography was carried out with a Teledyne ISCO combiflash Rf connected to ELSD and PDA detectors with UV detection set at 200-400 nm with a specific wavelength set at 300 nm. The HPLC separation was achieved using Varian ProStar HPLC system connected to a ProStar 335 photodiode array detector (PDA) with UV detection set at 240 nm and 300 nm. Semi-preparative reverse phase HPLC purification of samples was performed on a Luna 5 μm silica (2) (100 A°; 250×10.0 mm) column using a flow rate of 4.6 mL/min of a mobile phase consisting of $H_2O$ with 1% formic acid and MeOH.

Fermentation, Extraction, and Isolation

A fungal strains MSX59553 from the Mycosynthetix culture collection identified to be *Clonostachys rogersoniana* was utilized in the present study (Amrine, C. S. M., et al., *J. Ind. Microbiol. Biotechnol.* 2018, 45, 1053; Paguigan, N. D., et al., *J. Antibiot.* 2017, 70, 553). Erlenmeyer flasks containing 10 g of breakfast oatmeal were used in fermentating MSX59553 fungal strains over 11 days. Those solid media were extracted with 60 mL of acetone, each flask culture was chopped using a spatula, and then shaken for 16 h at 100 rpm. The extract was filtrated under vacuum and then evaporated, the solid extract was reconstituted in 90 mL of EtOAc partitioned against 150 mL of $H_2O$. The solvents were transferred into a separatory funnel, and the organic layer was drawn off and evaporated in vacuo. This material was re-formed using 100 mL of 1:1 MeOH:$CH_3CN$ and 100 mL of hexanes. The MeOH:$CH_3CN$ layer was drawn off and evaporated in vacuo. The defatted organic extract was adsorbed on Celite 545 (Acros Organics) and fractionated via flash chromatography on a 40 g RediSep Rf Gold Si-gel column using a gradient solvent system of hexanes-$CHCl_3$-MeOH at a flow rate of 40 mL/min over 53.3 column volumes (CV) for a duration of 63.9 min. Fractions were collected every 25.0 mL and pooled according to the UV and ELSD profiles, resulting in six fractions ($F_1$-$F_6$). Fraction $F_1$ and $F_3$ was observed to contain both the targeted masses of verticillin H and verticillin A, respectively. $F_1$ and $F_3$ was subjected to further purifications via partitions of MeOH:$CH_3CN$ against hexanes. The semisynthetic products were purified via reverse phase chromatography with a flow rate of 21.24 mL/min over 20 to 55 min.

Cytotoxicity Assay

Human melanoma cancer cells (MDA-MB-435), human breast cancer cells (MDA-MB-231) and human ovarian cancer cells (OVCAR3) were produced from the American Type Culture Collection (Manassas, VA). RPMI 1640 medium (fetal 10% bovine serum, 100 unites/mL penicillin and 100 μg/mL streptomycin) was used to culture cell lines. The cells were grown at 37° C. under 5% $CO_2$, then harvested during the log-phase growth by trypsinization followed by two washing to remove all traces of enzymes. 96-well clear, flat-bottom plate (Microtest 96, Falcon) was used to seed the cells at a density of 5000 cells per well. Each plate was incubated overnight at 37° C. under 5% $CO_2$. Sample concentrations of 20, 4, 0.8, 0.16, and 0.032 μM of were prepared by dissolving the pure compounds in DMSO, and a total volume of 100 μL and 0.5% DMSO were added to the appropriate wells. The cells with the test samples were incubated for 72 h at 37° C. Cell viability was examined using a commercial absorbance assay (CellTiter 96® AQ$_{ueous}$ One Solution Cell Proliferation Assay, Promega Corp, Madison, WI). $IC_{50}$ values were designated as the concentration required to reduce cellular growth by 50% compared to the untreated controls after 72 h of continuous exposure. Parents compounds; verticillin H and verticillin A were tested in comparison with the synthetic compounds and Taxol (Paclitaxel) was used as a positive control.

Synthesis of Compounds 11-20

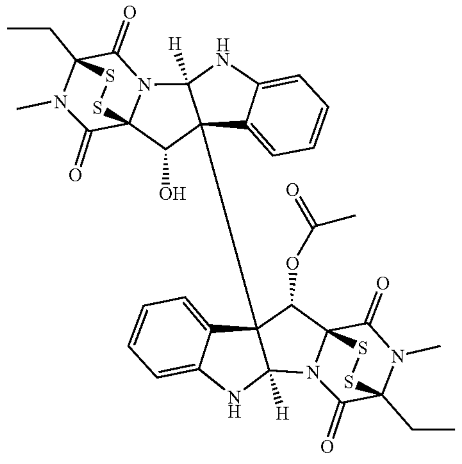 [SMILES: CC[C@@]12SS[C@]3(C(=O)N1C)[C@@H](O)[C@]1([C@@]45c6ccccc6N[C@@H]4N4C(=O)[C@]6(CC)SS[C@]4(C(=O)N6C)[C@H]5OC(C)=O)c4ccccc4N[C@@H]1N3C2=O]

Compound 11: Following the procedure reported for the acetylation of Verticillin D, (Joshi, B. K., et al., *J. Nat. Prod.* 1999, 62, 730). A solution of Verticillin H (1) (4 mg, 0.006 mmol), pyridine (0.2 mL), and acetic anhydride (1.5 mL) was stirred overnight at room temperature. The reaction was quenched with water and extracted with ethyl acetate. The combined organics were rinsed with 2M HCl, brine, and then dried over sodium sulfate, and concentrated in vacuo. The remaining solid was purified by HPLC to afford 11 (2.2 mg, 0.0028 mmol, 47% yield) as light-yellow powder. $^{1}H$ NMR ($CDCl_3$, 700 MHz) δ=1.20 (t, J=7.2 Hz, 3H), 1.21 (t, J=7.2 Hz, 3H), 2.12 (m, 1H), 2.16 (m, 1H), 2.36 (m, 2H), 2.46 (s, 3H), 2.94 (s, 3H), 3.00 (s, 3H), 5.02 (d, J=1.2 Hz, 1H), 5.17 (s, 1H), 5.17 (s, 1H), 5.18 (s, 1H), 5.22 (s, 1H), 5.43 (d, J=1.2 Hz, 1H), 6.64 (d, J=7.6 Hz, 1H), 6.68 (d, J=7.7 Hz, 1H), 6.85 (td, =7.6 Hz, 1.1 Hz, 1H), 6.88 (td, J=7.7 Hz, 1.0 Hz, 1H), 6.95 (s, 1H), 7.15 (td, J=7.6 Hz, 1.2 Hz, 1H), 7.19 (td, J=7.7 Hz, 1.2 Hz, 1H), 7.65 (d, J=7.7 Hz, 1H), 7.93 (d, J=7.6 Hz, 1H); $^{13}C$ NMR ($CDCl_3$, 175 MHz), δ=9.8 (2C), 22.1, 24.5, 24.7, 28.0, 28.5, 65.0, 65.9, 75.2, 76.7, 77.7, 78.3, 80.1, 81.9, 82.5, 83.1, 110.5, 111.1, 120.5, 120.7, 125.9, 128.4, 128.6, 129.0, 130.3, 130.5, 148.5, 149.0, 161.2, 161.3, 164.1, 166.8, 168.3. HRESIMS m/z 767.1433 $[M+H]^+$ (calcd for $C_{34}H_{35}N_6O_7S_4$, m/z 767.1450).

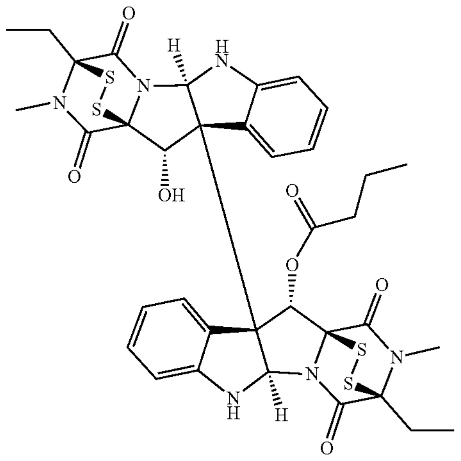 [SMILES: CCCC(=O)O[C@H]1[C@]2([C@@]34c5ccccc5N[C@@H]3N3C(=O)[C@]5(CC)SS[C@]3(C(=O)N5C)[C@H]4O)c3ccccc3N[C@@H]2N2C(=O)[C@]3(CC)SS[C@]12C(=O)N3C]

Compound 12: A solution of Verticillin H (1) (1 mg, 0.002 mmol), butyryl chloride (50 equiv., 0.01 mL), and triethylamine (70 equiv., 0.02 mL) in dichloromethane (0.25 mL) was stirred at rt for 4 hours before being quenched with water and extracted with ethyl acetate. The combined organic layers were dried over sodium sulfate and concentrated in vacuo prior to purification by HPLC to afford 12 (0.7 mg, 0.0009 mmol, 44% yield). as an off-white powder. $^{1}H$ NMR ($CDCl_3$, 500 MHz) δ=1.11 (t, J=7.4 Hz, 3H), 1.20 (t, J=7.2 Hz, 3H), 1.21 (t, J=7.2 Hz, 3H), 1.93 (m, 2H), 2.13 (m, 2H), 2.37 (m, 2H), 2.61 (m, 1H), 2.74 (m, 1H), 2.93 (s, 3H), 3.00 (s, 3H), 5.03 (d, J=1.2 Hz, 1H), 5.16 (s, 1H), 5.18 (s, 1H), 5.19 (s, 1H), 5.22 (s, 1H), 5.42 (d, J=1.2 Hz, 1H), 6.64 (d, J=7.6 Hz, 1H), 6.68 (d, J=7.7 Hz, 1H), 6.86 (td, J=7.7 Hz, 1.1 Hz, 1H), 6.90 (td, J=7.6 Hz, 1.1 Hz, 1H), 7.00 (s, 1H), 7.16 (td, J=7.6 Hz, 1.3 Hz, 1H), 7.20 (td, J=7.7 Hz, 1.2 Hz, 1H), 7.70 (d, J=7.6 Hz, 1H), 7.92 (d, J=7.7 Hz, 1H); $^{13}C$ NMR ($CDCl_3$, 175 MHz), δ=9.8, 13.9, 18.0, 24.5, 24.8, 28.0, 28.5, 29.7 (2 C), 65.1, 65.9, 75.2, 76.6, 77.7, 78.4, 79.9, 81.7, 82.5, 83.1, 110.5, 111.1, 120.6, 120.7, 126.0, 128.3, 128.7, 129.1, 130.3, 130.4, 148.5, 148.9, 161.2, 161.3, 164.0, 166.8, 171.1. HRESIMS m/z 795.1715 $[M+H]^+$ (calcd for $C_{36}H_{39}N_6O_7S_4$, m/z 795.1763).

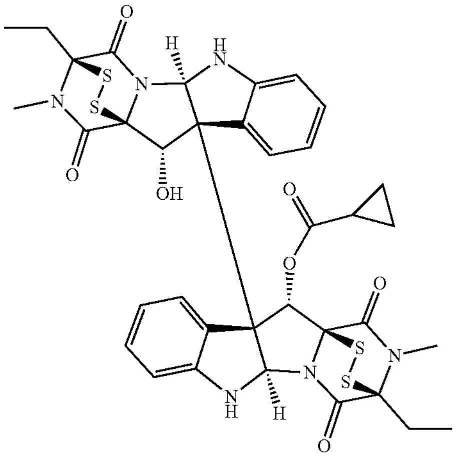 [SMILES: CC[C@@]12SS[C@]3(C(=O)N1C)[C@@H](O)[C@]1([C@@]45c6ccccc6N[C@@H]4N4C(=O)[C@]6(CC)SS[C@]4(C(=O)N6C)[C@H]5OC(=O)C4CC4)c4ccccc4N[C@@H]1N3C2=O]

Compound 13: A solution of Verticillin H (1) (3 mg, 0.004 mmol), cyclopropanecarbonyl chloride (5 equiv., 0.002 mL), and triethylamine (10 equiv., 0.006 mL) in chloroform-d (1 mL) was added to an NMR tube. The reaction was monitored for completion by looking for desymmetrization of the aromatic region in the NMR (completion observed as early as 30 minutes). After 3 hours at room temperature, the reaction mixture was then concentrated in vacuo providing a residue that was purified by HPLC to afford 13 (2.6 mg, 0.003 mmol, 82% yield) as an off-white powder. $^{1}H$ NMR ($CDCl_3$, 500 MHz) δ=1.13 (m, 2H), 1.21 (m, 6H), 1.25 (m, 1H), 1.48 (m, 1H), 1.96 (m, 1H), 2.13 (m, 2H), 2.36 (m, 2H), 2.95 (s, 3H), 3.00 (s, 3H), 5.13 (d, J=1.3 Hz, 1H), 5.18 (s, 1H), 5.20 (s, 2H), 5.22 (s, 1H), 5.36 (d, J=1.3 Hz, 1H), 6.65 (d, J=7.6 Hz, 1H), 6.69 (d, J=7.7 Hz, 1H), 6.85 (t, J=7.6 Hz, 1H), 6.89 (t, J=7.7 Hz, 1H), 6.94 (s, 1H), 7.15 (td, J=7.7 Hz, 1.2 Hz, 1H), 7.20 (td, J=7.6 Hz, 1.0 Hz, 1H), 7.84 (d, J=7.6 Hz, 1H), 7.90 (d, J=7.7 Hz, 1H); $^{13}C$ NMR ($CDCl_3$, 125 MHz), δ=9.2, 9.5, 9.8, 9.9, 13.6, 24.6, 24.9, 28.1, 28.7, 29.8, 65.3, 66.0, 75.3, 77.9, 78.6, 80.3, 81.7, 82.6, 83.4, 110.6, 111.2, 120.7, 120.8, 126.2, 128.4, 128.9, 129.2, 130.4, 130.6, 148.6, 149.0, 161.3, 161.4, 164.3, 166.9, 172.7. HRESIMS m/z 793.1582 $[M+H]^+$ (calcd for $C_{36}H_{37}N_6O_7S_4$, m/z 793.1606).

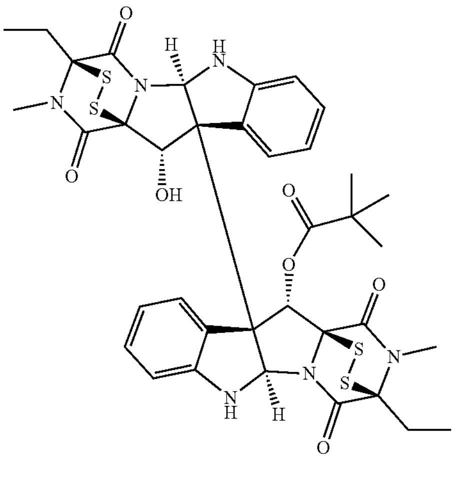 [SMILES: CC[C@@]12SS[C@]3(C(=O)N1C)[C@@H](O)[C@]1([C@@]45c6ccccc6N[C@@H]4N4C(=O)[C@]6(CC)SS[C@]4(C(=O)N6C)[C@H]5OC(=O)C(C)(C)C)c4ccccc4N[C@@H]1N3C2=O]

Compound 14: A solution of Verticillin H (1) (5 mg, 0.007 mmol), pivaloyl chloride (10 equiv., 0.009 mL), triethylamine (15 equiv., 0.015 mL), and dimethylaminopyridine (0.25 equiv., 0.01 mL of a 0.2 M solution in chloroform-d) in chloroform-d (1 mL) was stirred 22 hours at room temperature, after which transfer to an NMR tube confirmed consumption of starting material. The reaction mixture was then concentrated in vacuo providing a residue that was purified by HPLC to afford 14 (4.88 mg, 0.006 mmol, 86% yield). as an off-white powder. $^1$H NMR ($CDCl_3$, 400 MHz) δ=1.21 (m, 6H), 1.46 (s, 9H), 2.14 (m, 2H), 2.36 (m, 2H), 2.92 (s, 3H), 2.98 (s, 3H), 5.13 (s, 1H), 5.16 (s, 1H), 5.17 (s, 2H), 5.19 (s, 1H), 5.30 (s, 1H), 6.63 (d, J=7.6 Hz, 1H), 6.69 (d, J=7.7 Hz, 1H), 6.85 (t, J=7.6 Hz, 1H), 6.91 (t, J=7.7 Hz, 1H), 7.11 (s, 1H), 7.14 (t, J=7.7 Hz, 1H), 7.20 (t, J=7.6 Hz, 1H), 7.83 (d, J=7.6 Hz, 1H), 7.90 (d, J=7.7 Hz, 1H); $^{13}$C NMR ($CDCl_3$, 100 MHz), δ=9.9 (2 C), 24.7, 24.9, 27.7 (3 C), 28.0, 28.6, 29.8, 39.4, 64.8, 66.1, 75.7, 77.9, 78.7, 80.9, 81.1, 82.7, 83.4, 110.7, 111.4, 120.5, 120.8, 125.9, 128.2, 129.1, 129.9, 130.4, 130.5, 148.3, 148.7, 161.4, 161.5, 164.0, 166.9, 176.8. HRESIMS m/z 809.1894 $[M+H]^+$ (calcd for $C_{37}H_{41}N_6O_7S_4$, m/z 809.1919).

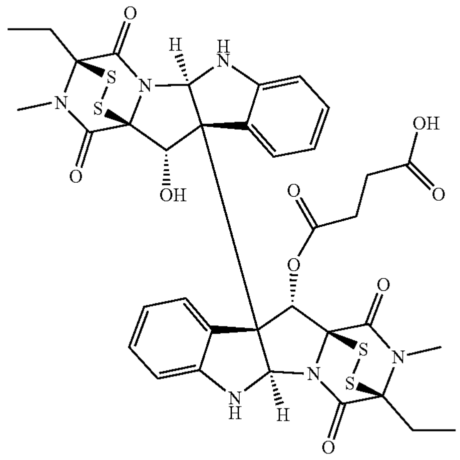 [SMILES: CC[C@@]12SS[C@]3(C(=O)N1C)[C@@H](O)[C@]1([C@@]45c6ccccc6N[C@@H]4N4C(=O)[C@]6(CC)SS[C@]4(C(=O)N6C)[C@H]5OC(=O)CCC(=O)O)c4ccccc4N[C@@H]1N3C2=O]

Compound 15: General Procedure for Succinates: A suspension of Verticillin H (1) (17 mg, 0.023 mmol), succinic anhydride (50 equiv., 38 mg), 4-dimethylaminopyridine (0.25 equiv., 0.009 mL of a 0.2 M solution in chloroform-d), and pyridine (50 equiv., 0.030 mL) in dimethylformamide (1 mL) was stirred at room temperature overnight, during which time the mixture became a clear solution. Solvent was then removed by vacuum distillation and the remaining solid was purified by HPLC to afford 15 (10 mg, 0.012 mmol, 53% yield). as a light-yellow powder. $^1$H NMR ($CDCl_3$, 700 MHz) δ=1.20 (t, J=7.4 Hz, 3H), 1.21 (t, J=7.2 Hz, 3H), 2.14 (m, 2H), 2.36 (m, 2H), 2.68 (dt, J=17.5, 4.1 Hz, 1H), 2.88 (dt, J=17.1, 4.1 Hz, 1H), 2.92 (s, 3H), 3.00 (s, 3H), 3.06 (ddd, J=17.1, 12.1, 4.1 Hz, 1H), 3.18 (ddd, J=17.5, 12.1, 4.1 Hz, 1H), 5.02 (d, J=1.9 Hz, 1H), 5.17 (s, 1H), 5.18 (s, 1H), 5.18 (s, 1H), 5.20 (s, 1H), 5.52 (d, J=1.9 Hz, 1H), 6.64 (d, J=7.7 Hz, 1H), 6.67 (d, J=7.8 Hz, 1H), 6.84 (t, =7.7 Hz, 1H), 6.90 (t, J=7.8 Hz, 1H), 7.00 (s, 1H), 7.14 (t, J=7.7 Hz, 1H), 7.19 (td, J=7.8 Hz, 1.2 Hz, 1H), 7.76 (d, J=7.7 Hz, 1H), 7.92 (d, J=7.8 Hz, 1H); $^{13}$C NMR ($CDCl_3$, 175 MHz), δ=9.7, 9.8, 24.5, 24.7, 28.1, 28.4, 28.5, 30.1, 65.1, 65.7, 75.0, 77.3, 77.9, 78.3, 80.4, 81.0, 82.5, 83.1, 110.5, 111.0, 120.6, 120.7, 126.1, 128.2, 128.9, 129.2, 130.3, 130.4, 148.4, 148.8, 161.2, 161.2, 164.2, 166.7, 170.9, 173.9. HRESIMS m/z 825.1502 $[M+H]^+$ (calcd for $C_{36}H_{37}N_6O_9S_4$, m/z 825.1504).

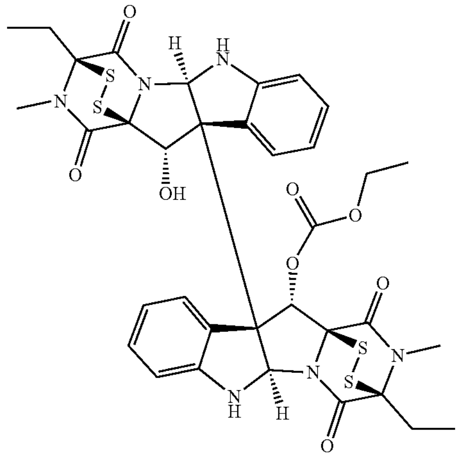 [SMILES: CCOC(=O)O[C@H]1[C@]2([C@@]34c5ccccc5N[C@@H]3N3C(=O)[C@]5(CC)SS[C@]3(C(=O)N5C)[C@H]4O)c3ccccc3N[C@@H]2N2C(=O)[C@]3(CC)SS[C@]12C(=O)N3C]

Compound 16: A solution of Verticillin H (1) (5 mg, 0.007 mmol), ethyl chloroformate (5 equiv., 0.003 mL), triethylamine (10 equiv., 0.01 mL), and dimethylaminopyridine (0.25 equiv., 0.009 mL of a 0.2 M solution in chloroform-d) in chloroform-d (1 mL) was added to an NMR tube. After 3 hours (consumption of starting material observed after 90 minutes) at room temperature, the reaction mixture was concentrated in vacuo providing a residue that was purified by HPLC to afford 16 (2.7 mg, 0.004 mmol, 57% yield) as an off-white powder. $^1$H NMR ($CDCl_3$, 500 MHz) δ=1.18 (t, J=7.2 Hz, 3H), 1.22 (t, J=7.2 Hz, 3H), 1.49 (t, J=7.1 Hz, 3H), 2.14 (m, 2H), 2.36 (m, 2H), 2.95 (s, 3H), 3.01 (s, 3H), 4.54 (q, J=7.1 Hz, 2H), 5.10 (s, 1H), 5.14 (s, 1H), 5.18 (s, 1H), 5.19 (s, 1H), 5.22 (s, 1H), 5.52 (d, J=1.2 Hz, 1H), 6.65 (m, 2H), 6.75 (s, 1H), 6.88 (m, 2H), 7.16 (m, 2H), 7.79 (d, J=7.7 Hz, 1H), 7.92 (d, J=7.8 Hz, 1H); $^{13}$C NMR ($CDCl_3$, 125 MHz), δ=9.9 (2 C), 14.6, 24.6, 24.8, 28.1, 28.6, 29.8, 65.3, 65.6, 66.0, 75.5, 76.7, 77.7, 78.5, 82.0, 82.5, 83.3, 84.0, 110.7, 111.0, 120.8, 121.1, 127.0, 128.4, 128.6, 128.7, 130.5, 148.7, 148.9, 153.7, 161.2, 161.3, 164.4, 167.0. HRESIMS m/z 809.1894 $[M+H]^+$ (calcd for $C_{35}H_{37}N_6O_8S_4$, m/z 809.1919).

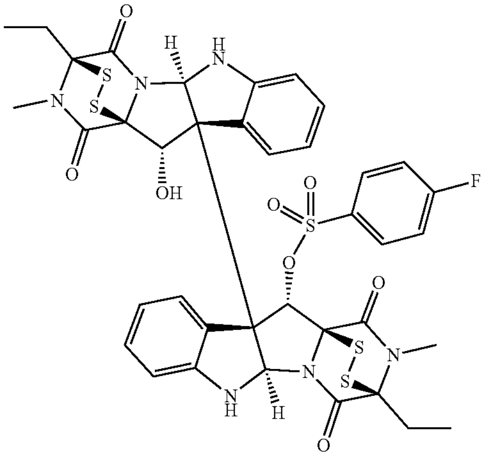 [SMILES: CC[C@@]12SS[C@]3(C(=O)N1C)[C@@H](O)[C@]1([C@@]45c6ccccc6N[C@@H]4N4C(=O)[C@]6(CC)SS[C@]4(C(=O)N6C)[C@H]5OS(=O)(=O)c4ccc(F)cc4)c4ccccc4N[C@@H]1N3C2=O]

Compound 17: A solution of Verticillin H (1) (6 mg, 0.008 mmol), 4-fluorobenzenesulfonyl chloride (5 equiv., 8 mg), triethylamine (10 equiv., 0.012 mL), and dimethylaminopyridine (0.25 equiv., 0.01 mL of a 0.2 M solution in chloroform-d) in chloroform-d (1 mL) was stirred 22 hours at room temperature, after which transfer to an NMR tube confirmed consumption of starting material. The reaction mixture was then concentrated in vacuo providing a residue that was purified by HPLC to afford 17 (2.9 mg, 0.003 mmol, 41% yield). as an off-white powder. $^1$H NMR ($CDCl_3$, 500 MHz) δ=1.13 (t, J=7.0 Hz, 3H), 1.21 (t, J=7.2 Hz, 3H), 2.05 (m, 1H), 2.17 (m, 1H), 2.30 (m, 1H), 2.37 (m, 1H), 2.66 (s, 3H), 3.00 (s, 3H), 5.16 (s, 1H), 5.17 (s, 1H), 5.21 (s, 2H), 5.69 (s, 2H), 6.61 (d, J=7.8 Hz, 1H), 6.66 (d, J=7.7 Hz, 1H), 6.73 (s, 1H), 6.85 (t, J=7.8 Hz, 1H), 6.94 (t, J=7.7 Hz, 1H), 7.14 (t, J=7.7 Hz, 1H), 7.22 (m, J=8.6 Hz, 8.0 Hz 3H), 7.87 (d, J=7.8 Hz, 1H), 7.94 (d, J=7.7 Hz, 1H), 8.11 (m, J=8.6 Hz, 4.8 Hz, 2H); $^{13}$C NMR ($CDCl_3$, 125 MHz), δ=9.9 (2 C), 24.7 (2 C), 28.1, 28.4, 66.0, 66.8, 76.4, 77.3, 77.8, 79.6, 80.7, 82.1, 83.6, 88.7, 110.7, 111.0, 115.9, 116.1, 120.5, 120.9, 126.7, 128.4 (2 C), 129.1, 130.5 (2 C), 130.6, 130.7, 148.8, 149.0, 160.8, 161.4, 162.4, 164.5, 166.6 (d, J=194.9 Hz), 166.9. HRESIMS m/z 883.1171 $[M+H]^+$ (calcd for $C_{38}H_{36}FN_6O_8S_5$, m/z 883.1182).

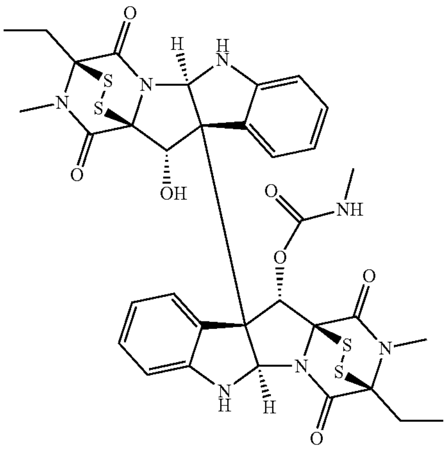 [SMILES: CC[C@@]12SS[C@]3(C(=O)N1C)[C@@H](O)[C@]1([C@@]45c6ccccc6N[C@@H]4N4C(=O)[C@]6(CC)SS[C@]4(C(=O)N6C)[C@H]5OC(=O)NC)c4ccccc4N[C@@H]1N3C2=O]

Compound 18: General Procedure for Carbamates (Rannard, S. P., et al., *Org. Lett.* 2000, 2, 2117): A slurry of Verticillin H (1) (5 mg, 0.007 mmol), carbonyldiimidazole (15 equiv., 34 mg), potassium hydroxide (cat., 2 mg), and dimethylaminopyridine (0.25 equiv., 0.014 mL of a 0.2 M solution in chloroform-d) in chloroform-d (1 mL) was stirred at 50-55° C. (eventually becoming a clear solution) for 2 hours at which time transfer to an NMR tube confirmed consumption of starting material. After transferring back into the reaction vessel, methylamine (5 equiv., 0.008 mL) was added and the resulting reaction mixture was stirred overnight at room temperature. The reaction mixture was then concentrated in vacuo providing a residue that was dissolved in ethyl acetate and washed with several portions of water (back extracted with ethyl acetate). The combined organics were rinsed with brine, dried over sodium sulfate, and concentrated in vacuo prior to purification by HPLC to afford Compound 18 (1 mg, 0.0013 mmol, 18% yield). as an off-white powder. $^1$H NMR ($CDCl_3$, 700 MHz) δ=1.18 (t, J=7.2 Hz, 3H), 1.21 (t, J=7.2 Hz, 3H), 2.12 (m, 2H), 2.36 (m, 2H), 2.93 (s, 3H), 2.99 (s, 3H), 3.06 (d, J=4.8 Hz, 3H), 4.86 (m, 1H), 5.12 (d, J=1.9 Hz, 1H), 5.15 (s, 1H), 5.18 (s, 1H), 5.19 (s, 1H), 5.21 (s, 1H), 5.32 (d, J=1.9 1H), 6.64 (d, J=7.7 Hz, 1H), 6.67 (d, J=7.7 Hz, 1H), 6.85 (m, 2H), 6.88 (s, 1H), 7.14 (t, J=7.7 Hz, 1H), 7.18 (t, J=7.7 Hz, 1H), 7.48 (d, J=7.7 Hz, 1H), 7.94 (d, J=7.7 Hz, 1H); $^{13}$C NMR ($CDCl_3$, 175 MHz), δ=9.8 (2 C), 24.6, 24.7, 28.0, 28.5, 28.6, 29.7, 50.9, 65.1, 65.8, 76.1, 77.9, 78.4, 81.4, 81.5, 82.5, 83.2, 110.6, 111.1, 120.2, 120.7, 128.6, 128.8, 129.1, 130.2, 130.4, 148.5, 149.1, 155.2, 161.2, 161.3, 164.3, 166.5. HRESIMS m/z 782.1550 $[M+H]^+$ (calcd for $C_{34}H_{36}N_7O_7S_4$, m/z 782.1559).

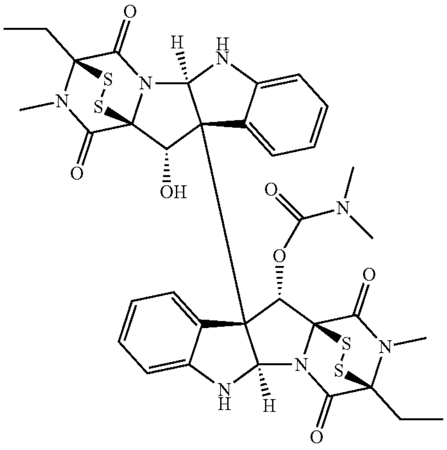 [SMILES: CC[C@@]12SS[C@]3(C(=O)N1C)[C@@H](O)[C@]1([C@@]45c6ccccc6N[C@@H]4N4C(=O)[C@]6(CC)SS[C@]4(C(=O)N6C)[C@H]5OC(=O)N(C)C)c4ccccc4N[C@@H]1N3C2=O]

Compound 19: Utilizing dimethylamine, in the general procedure for carbamates, Verticillin H (1) (10 mg, 0.014 mmol) afforded 19 (4.5 mg, 0.006 mmol, 43% yield). as an off-white powder. $^1$H NMR ($CDCl_3$, 500 MHz) δ=1.20 (t, J=7.4 Hz, 6H), 2.13 (m, 2H), 2.36 (m, 2H), 2.92 (s, 3H), 2.98 (s, 3H), 3.01 (s, 3H), 3.14 (s, 3H), 5.14 (d, J=2.9 Hz, 1H), 5.20 (s, 2H), 5.21 (s, 1H), 5.24 (s, 1H), 5.33 (d, J=3.0, 1H), 6.65 (d, J=7.8 Hz, 1H), 6.67 (d, J=7.8 Hz, 1H), 6.84 (m, 2H), 6.96 (s, 1H), 7.15 (m, 2H), 7.50 (d, J=7.7 Hz, 1H), 7.96 (d, J=7.7 Hz, 1H); $^{13}$C NMR ($CDCl_3$, 125 MHz), δ=9.9 (2 C), 24.7, 24.8, 28.1, 28.6, 65.2, 65.5, 77.0, 77.2, 77.3, 77.8, 78.2, 78.6, 81.0, 82.1, 82.7, 83.6, 110.9, 111.4, 120.1, 120.9, 126.4, 128.9, 129.0, 129.4, 130.3, 130.5, 148.7, 149.3, 155.7, 161.4, 161.6, 164.5, 166.3. HRESIMS m/z 796.1724 $[M+H]^+$ (calcd for $C_{35}H_{38}N_7O_7S_4$, m/z 796.1715).

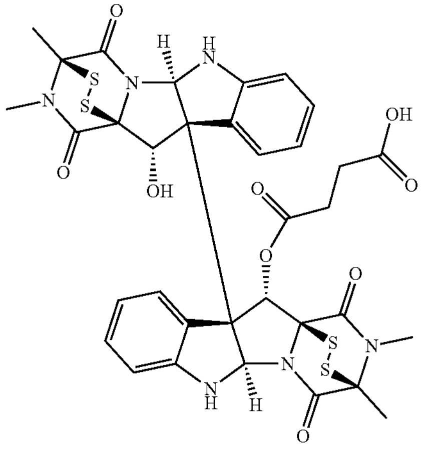

Compound 20: Utilizing the general procedure for succination previously described, Verticillin A (3) (5 mg, 0.008 mmol) afforded 20 (4.5 mg, 0.006 mmol, 71% yield). as a white powder. $^1$H NMR ($CDCl_3$, 400 MHz) δ=1.87 (s, 3H), 1.88 (s, 3H), 2.66 (dt, J=17.3 Hz, 3.7 Hz, 1H), 2.85 (dt, J=17.3 Hz, 3.7 Hz, 1H), 2.90 (s, 3H), 2.97 (s, 3H), 3.04 (dt, J=17.3 Hz, 3.7 Hz, 1H), 3.18 (dt, J=17.3 Hz, 3.7 Hz, 1H), 5.11 (s, 1H), 5.15 (s, 3H), 5.52 (d, J=1.8 Hz, 1H), 6.64 (d, J=7.7 Hz, 1H), 6.67 (d, J=7.7 Hz, 1H), 6.84 (t, J=7.7 Hz, 1H), 6.88 (t, =7.7 Hz, 1H), 6.98 (s, 1H), 7.16 (m, 2H), 7.73 (d, J=7.7 Hz, 1H), 7.90 (d, J=7.7 Hz, 1H); $^{13}$C NMR ($CDCl_3$, 100 MHz), δ=17.6, 17.8, 27.4, 27.7, 28.5, 30.2, 65.3, 66.0, 73.4, 73.8, 74.8, 77.3, 80.4, 81.1, 82.4, 83.0, 110.7, 111.2, 120.7, 120.8, 126.2, 128.3, 129.0, 129.3, 130.4, 130.5, 148.4, 148.8, 162.2, 162.3, 163.2, 165.8, 171.0, 174.2. HRESIMS m/z 797.11584 $[M+H]^+$ (calcd for $C_{34}H_{33}N_6O_9S_4$, m/z 797.1191).

Results

Verticillin H was selected as the substrate for these studies based on 1) the relative abundance/production of the compound upon culture of the fungus MSX59553[32] and 2) the symmetric nature of the substitution of the ketopiperizine ring. This symmetry would potentially assist with the purification and data analysis in the event of substitution at only a single position on the dimeric structure of the analogue, potentially avoiding the formation of two closely related regioisomeric product. To this end, initial analysis of the structure of verticillin H suggested the C11/C11' hydroxy substituents as the most appropriate and accessible functional groups for semi-synthetic functionalization. This was further supported by findings from the initial isolation papers for both verticillin A and verticillin D, which both showed that acetylation of only one of these "central" alcohols could be accomplished on treatment of the natural compounds with acetic anhydride and pyridine. To explain this finding, Gloer and Wicklow specifically indicated a potential "conformational bias" that precluded reaction at the C11' position.

In an effort to confirm this interesting reactivity, verticillin H was first treated with acetic anhydride under conditions similar to those previously reported. The acetylation reaction proceeded smoothly, resulting in the acylation of only a single alcohol moiety to generate compound 11. Formation of the mono-acetylated product could easily be confirmed via analysis of the $^1$H NMR spectrum, which indicated desymmetrization of the aromatic protons through apparent "doubling" of the diagnostic peaks between 6.5 and 8.0 ppm. LC/MS analysis of the crude reaction mixture in this case failed to show any evidence of bis-acetylation. Attempts to acylate both the C11 and C11' alcohols utilizing the more reactive acetyl chloride also failed, likewise resulting primarily in the formation of the mono-acetylated product. Interestingly, in this case, compound 11 was also accompanied by the formation of a byproduct with the same molecular mass as the desired bis-acetylated product. The $^1$H NMR that was obtained, however, still indicated the acylation of only a single alcohol due to the observation of a similar pattern in the aromatic region and the presence of only three methyl groups in the spectrum. Although not unambiguously established, the appearance of two new sets of doublets between 3.75 and 4.0 suggested the formation of an unanticipated ketoester byproduct derived from acylation of the initially introduced C11-acetyl group. This result clearly demonstrated the high barrier to reactivity at this second alcohol position.

Having successfully acylated the C-11 position, however, the strategy for further manipulation of verticillin H shifted to the introduction of alternative groups that would demonstrate the versatility of reactivity at this position and would be predicted to affect the physicochemical properties of the molecule, specifically through manipulation of solubility and relative stability. This was anticipated to include several ester derivatives with various substitution patterns, as well as the formation of carbonate, carbamate, and sulfonate analogues. Based on the diagnostic NMR shifts of the aromatic protons during the previous reaction and the small scale on which subsequent reactions would initially be carried out, these acylation reactions would be run in NMR tubes and monitored by tracking the desymmetrization of the aromatic protons. After a simple workup, the crude reaction mixtures would then be purified utilizing a UPLC system.

Using this approach, a series of four additional ester analogues (compounds 12-15) were generated, demonstrating the ability to generate both straight chain and branched chain derivatives. Despite the additional steric congestion, the pivaloyl derivative 14 was obtained in comparable or even better yield than the other ester analogues. This result suggests that although the conformation of the acylated derivatives precludes further reaction at the C11' position, there is no significant size limitation for the initial acylation event. The most interesting of these four examples, however, is the succinate 15. In this case, the ester was formed through addition into succinic anhydride rather than an acid chloride. The introduction of the succinic acid moiety is commonly employed for prodrug development and can dramatically impact the relative water solubility of the natural product. Similar to the esters, carbonate 16 was generated upon treatment of verticillin H with ethyl chloroformate. Carbamates 18 and 19, however, were generated through a two-step procedure involving initial acylation with carbonyldiimidazole and subsequent treatment with the desired amine precursor for the formation of the carbamate.

As noted above for compound 11, the $^1$H NMR spectra of the ester derivatives (11-15 and 20), carbonate (16), sulfonate (17), and the carbamates (18 and 19) were similarly characterized by a notable doubling of signals that illustrated the loss of symmetry of the starting material. A distinct singlet peak in the range between 6.73 and 7.11 ppm was observed in all $^1$H NMR spectra and was found to represent H-11. The downfield shift of this peak compared to H-11' (~5 ppm) of the same molecule and the parent compound H-11 (δ=5.2), further confirms the linkage of the new groups to OH-11. In addition to the doubling of the peaks in the $^1$H NMR spectra, doubling of peaks could also clearly be observed in the $^{13}$C spectra for each analogue.

Cytotoxicity Assay

The antiproliferative properties of the newly synthesized analogues were evaluated against human melanoma cancer cells (MDA-MB-435), human breast cancer cells (MDA-MB-231), and human ovarian cancer cells (OVCAR3). Growth inhibition was measured after a 72 h exposure to the compound as previously described.[33, 34] The results of this screening showed that in nearly every case, the acylated verticillin H derivatives 11-19 performed as well or better than the parent compound. The lone exception across the three cell lines was compound 17, which showed a 1.6 fold loss of potency in the MDA-MB-231 cells. Surprisingly, however, even this compound was 2.9 times more potent in the OVCAR3 cells. Compounds that showed the greatest potency changes were compound 16 in the 231 cells and compound 19 in the OVCAR3 cells, with 4.4 and 12.0 fold increases, respectively. Overall, the fact that activity against these cell lines was retained was surprising, but shows that this is a viable strategy to not only introduce groups that may increase solubility in a prodrug sense, but also that have the potential to show greater metabolic stability as in the case of the carbonate and carbamate derivatives.

In summary, a series of verticillin analogues were synthesized with ester, carbonate, sulfonate, and carbamate linkages. These reactions were monitored essentially via $^1$H NMR to investigate the completion of the reaction. These compounds retained cytotoxic potency at the nM level. Most importantly, the addition of the linkages on the parent metabolites enhanced the solubility of this class of compounds in a solution of phosphate buffer saline (PBS, 7.4 pH).

REFERENCES

1. Siegel, R. L.; Miller, K. D.; Jemal, A., Cancer statistics, 2019. *CA: A cancer journal for clinicians* 2019, 69 (1), 7-34.
2. Society, A. C., American Cancer Society: Cancer Facts & FIGS. 2019. *Atlanta, Ga.: American Cancer Society* 2019.
3. Cragg, G. M.; Newman, D. J., Natural products as sources of anticancer agents: Current approaches and perspectives. In *Natural Products as Source of Molecules with Therapeutic Potential*, Springer: 2018; pp 309-331.
4. Kinghorn, A. D.; Carcache De Blanco, E. J.; Lucas, D. M.; Rakotondraibe, H. L.; Orjala, J.; Soejarto, D. D.; Oberlies, N. H.; Pearce, C. J.; Wani, M. C.; Stockwell, B. R.; Burdette, J. E.; Swanson, S. M.; Fuchs, J. R.; Phelps, M. A.; Xu, L.; Zhang, X.; Shen, Y. Y., Discovery of anticancer agents of diverse natural origin. *Anticancer research* 2016, 36 (11), 5623-5637.
5. Newman, D., J.; Cragg, G., M., Natural products as sources of new drugs from 1981 to 2014. *Journal of Natural Products* 2016, 79 (3), 629-661.
6. Fakhouri, L.; El-Elimat, T.; Hurst, D. P.; Reggio, P. H.; Pearce, C. J.; Oberlies, N. H.; Croatt, M. P., Isolation, semisynthesis, covalent docking and transforming growth factor beta-activated kinase 1 (TAK1)-inhibitory activities of (5Z)-7-oxozeaenol analogues. *Bioorganic & Medicinal Chemistry* 2015, 23 (21), 6993-6999.
7. Altmann, K.-H.; Gaugaz, F. Z.; Schiess, R., Diversity through semisynthesis: the chemistry and biological activity of semisynthetic epothilone derivatives. *Molecular diversity* 2011, 15 (2), 383-399.
8. Nicolaou, K.; Pfefferkorn, J.; Roecker, A.; Cao, G.-Q.; Barluenga, S.; Mitchell, H., Natural product-like combinatorial libraries based on privileged structures. 1. General principles and solid-phase synthesis of benzopyrans. *Journal of the American Chemical Society* 2000, 122 (41), 9939-9953.
9. Harvey, A. L.; Clark, R. L.; Mackay, S. P.; Johnston, B. F., Current strategies for drug discovery through natural products. *Expert opinion on drug discovery* 2010, 5 (6), 559-568.
10. Yoshioka, T.; Murakami, K.; Ido, K.; Hanaki, M.; Yamaguchi, K.; Midorikawa, S.; Taniwaki, S.; Gunji, H.; Irie, K., Semisynthesis and structure-activity studies of uncarinic acid C isolated from uncaria rhynchophylla as a specific inhibitor of the nucleation phase in amyloid β42 aggregation. *Journal of natural products* 2016, 79 (10), 2521-2529.
11. Bian, L.; Cao, S.; Cheng, L.; Nakazaki, A.; Nishikawa, T.; Qi, J., Semi-synthesis and structure-activity relationship of neuritogenic oleanene derivatives. *ChemMedChem* 2018, 13 (18), 1972-1977.
12. Xu, H.; Wang, J.; Sun, H.; Lv, M.; Tian, X.; Yao, X.; Zhang, X., Semisynthesis and quantitative structure-activity relationship (QSAR) study of novel aromatic esters of 4'-demethyl-4-deoxypodophyllotoxin as insecticidal agents. *Journal of agricultural and food chemistry* 2009, 57 (17), 7919-7923.
13. Lee, R. E.; Hurdle, J. G.; Liu, J.; Bruhn, D. F.; Matt, T.; Scherman, M. S.; Vaddady, P. K.; Zheng, Z.; Qi, J.; Akbergenov, R., Spectinamides: a new class of semisynthetic antituberculosis agents that overcome native drug efflux. *Nature medicine* 2014, 20 (2), 152.
14. Newman, D. J., Developing natural product drugs: Supply problems and how they have been overcome. *Pharmacology & therapeutics* 2016, 162, 1-9.
15. Kung, S. H.; Lund, S.; Murarka, A.; McPhee, D.; Paddon, C. J., Approaches and recent developments for the commercial production of semi-synthetic artemisinin. *Frontiers in plant science* 2018, 9, 87.
16. McElroy, C.; Jennewein, S., Taxol® biosynthesis and production: from forests to fermenters. In *Biotechnology of Natural Products*, Springer: 2018; pp 145-185.
17. Oberlies, N. H.; Kroll, D. J., Camptothecin and taxol: historic achievements in natural products research. *Journal of natural products* 2004, 67 (2), 129-135.
18. Ringel, I.; Horwitz, S. B., Studies with RP 56976 (taxotere): a semisynthetic analogue of taxol. *JNCI: Journal of the National Cancer Institute* 1991, 83 (4), 288-291.
19. Guenard, D.; Gueritte-Voegelein, F.; Potier, P., Taxol and taxotere: discovery, chemistry, and structure-activity relationships. *Accounts of chemical research* 1993, 26 (4), 160-167.
20. Walko, C. M.; Lindley, C., Capecitabine: a review. *Clinical therapeutics* 2005, 27 (1), 23-44.
21. Puhalla, S.; Brufsky, A., Ixabepilone: a new chemotherapeutic option for refractory metastatic breast cancer. *Biologics: targets & therapy* 2008, 2 (3), 505.
22. Fumoleau, P.; Coudert, B.; Isambert, N.; Ferrant, E., Novel tubulin-targeting agents: anticancer activity and pharmacologic profile of epothilones and related analogues. *Annals of oncology* 2007, 18 (suppl_5), v9-v15.
23. O'Leary, J.; Muggia, F., Camptothecins: a review of their development and schedules of administration. *European Journal of Cancer* 1998, 34 (10), 1500-1508.
24. Tsuruo, T.; Matsuzaki, T.; Matsushita, M.; Saito, H.; Yokokura, T., Antitumor effect of CPT-11, a new derivative of camptothecin, against pleiotropic drug-resistant tumors in vitro and in vivo. *Cancer chemotherapy and pharmacology* 1988, 21 (1), 71-74.
25. Kawato, Y.; Furuta, T.; Aonuma, M.; Yasuoka, M.; Yokokura, T.; Matsumoto, K., Antitumor activity of a camptothecin derivative, CPT-11, against human tumor xenografts in nude mice. *Cancer chemotherapy and pharmacology* 1991, 28 (3), 192-198.
26. FDA approves irinotecan as first-line therapy for colorectal cancer. *Oncology* (*Williston Park*) 2000, 14 (5), 652, 654.
27. Iwasa, E.; Hamashima, Y.; Sodeoka, M., Epipolythiodiketopiperazine alkaloids: Total syntheses and biological activities. *Israel Journal of Chemistry* 2011, 51 (3-4), 420-433.
28. Zewdu, A.; Lopez, G.; Braggio, D.; Kenny, C.; Constantino, D.; Bid, H. K.; Batte, K.; Iwenofu, O. H.; Oberlies, N. H.; Pearce, C. J.; Strohecker, A. M.; Lev, D.; Pollock, R. E., Verticillin A inhibits leiomyosarcoma and malignant peripheral nerve sheath tumor growth via induction of apoptosis. *Clinical & experimental pharmacology* 2016, 6 (6), 221-234.
29. Jordan, T. W.; Cordiner, S. J., Fungal epipolythiodioxopiperazine toxins have therapeutic potential and roles in disease. *Trends in Pharmacological Sciences* 1987, 8 (4), 144-149.

30. Gardiner, D. M.; Waring, P.; Howlett, B. J., The epipolythiodioxopiperazine (ETP) class of fungal toxins: distribution, mode of action, functions and biosynthesis. *Microbiology* 2005, 151 (4), 1021-1032.
31. Liu, F.; Wu, S.; Chen, Y.; Yang, L.; Wu, P., Verticillin chloroform solvate. *Acta Crystallographica, Section E: Structure Reports Online* 2006, 62 (3), 974-976.
32. Amrine, C. S. M.; Raja, H. A.; Darveaux, B. A.; Pearce, C. J.; Oberlies, N. H., Media studies to enhance the production of verticillins facilitated by in situ chemical analysis. *Journal of Industrial Microbiology & Biotechnology* 2018, 45 (12), 1053-1065.
33. Figueroa, M.; Graf, T. N.; Ayers, S.; Adcock, A. F.; Kroll, D. J.; Yang, J.; Swanson, S. M.; Munoz-Acuna, U.; Carcache de Blanco, E. J.; Agrawal, R.; Wani, M. C.; Darveaux, B. A.; Pearce, C. J.; Oberlies, N. H., Cytotoxic epipolythiodioxopiperazine alkaloids from filamentous fungi of the Bionectriaceae. *Journal of Antibiotics* 2012, 65 (11), 559-564.
34. El-Elimat, T.; Figueroa, M.; Raja, H. A.; Graf, T. N.; Swanson, S. M.; Falkinham III, J. O.; Wani, M. C.; Pearce, C. J.; Oberlies, N. H., Biosynthetically distinct cytotoxic polyketides from *Setophoma terrestris. European journal of organic chemistry* 2015, 2015 (1), 109-121.

Example 3. Acetylation of Fluorinated Epipolythiodioxopiperazine Alkaloids

Acetylation of fluorinated epipolythiodioxopiperazine alkaloids (verticillins) is accomplished by a variety of methodologies. One approach involves using precursor-directed biosynthesis which harnesses the biosynthetic machinery of a microorganism by introducing analogous building blocks to those used naturally. For example, fluorinated verticillins can be prepared by incorporating fluorinated amino acids such fluorinated 5-F-DL-tryptophan (5-F-$_{DL}$-Trp) into culture media of the fungus *Clonostachys rogersoniana* (strain MSX59553) as described in example 1, to generate seven fluorinated analogues (compounds 4-10).

Acetylation of the fluorinated verticillins derivatives (compounds 4-10) is achieved following conditions similar to those previously described in example 2 for the synthesis of compounds 11-20.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A compound having Formula I:

Formula I

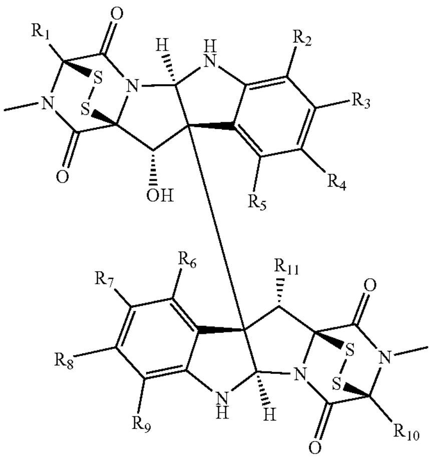

wherein $R_1$ and $R_{10}$ are independently unsubstituted alkyl;

$R_4$ and $R_7$ are both halogen or hydrogen; $R_4$ is hydrogen and $R_7$ is halogen; or $R_4$ is halogen and $R_7$ is hydrogen;

$R_2$, $R_3$, $R_5$, $R_6$, $R_8$, and $R_9$ are independently hydrogen; halogen; amino; hydroxy; thiol; ester; carbamate; carbonate; sulfonate; substituted or unsubstituted alkyl, alkenyl, alkynyl, or alkoxy; and $R_{11}$ is a hydroxy, ester, carbamate, carbonate, or sulfonate;

wherein when $R_{11}$ is a hydroxy, then $R_4$ and $R_7$ are both halogen, $R_4$ is hydrogen and $R_7$ is halogen, or $R_4$ is halogen and $R_7$ is hydrogen;

wherein when $R_1$ and $R_{10}$ are methyl, $R_2$, $R_3$, $R_5$, $R_6$, $R_8$, and $R_9$ are H, and $R_{11}$ is

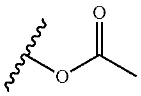, then $R_4$ and $R_7$ are both halogen; $R_4$ is hydrogen and $R_7$ is halogen; or $R_7$ is halogen and $R_4$ is hydrogen;

or a pharmaceutically acceptable salt thereof.

2. A compound having Formula II:

Formula II

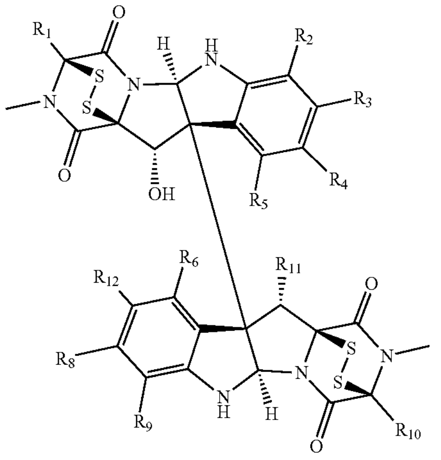

wherein $R_1$ and $R_{10}$ are independently substituted or unsubstituted alkyl;

$R_{12}$ and $R_{13}$ are both halogen; $R_{12}$ is hydrogen and $R_{13}$ is halogen; or $R_{12}$ is halogen and $R_{13}$ is hydrogen;

$R_2$, $R_3$, $R_5$, $R_6$, $R_8$, and $R_9$ are independently hydrogen; halogen; amino; hydroxy; thiol; ester; carbamate; carbonate; sulfonate; substituted or unsubstituted alkyl, alkenyl, alkynyl, or alkoxy; and $R_{11}$ is a hydroxy, ester, carbamate, carbonate, or sulfonate;

or a pharmaceutically acceptable salt thereof.

3. A compound having Formula III:

Formula III

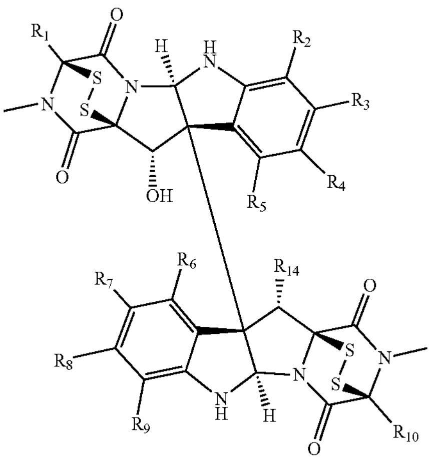

wherein $R_1$ and $R_{10}$ are independently unsubstituted alkyl;

$R_4$ and $R_7$ are both halogen or hydrogen; $R_4$ is hydrogen and $R_7$ is halogen; or $R_4$ is halogen and $R_7$ is hydrogen;

$R_2$, $R_3$, $R_5$, $R_6$, $R_8$, and $R_9$ are independently hydrogen; halogen; amino; hydroxy; thiol; ester; carbamate; carbonate; sulfonate; substituted or unsubstituted alkyl, alkenyl, alkynyl, or alkoxy; and $R_{14}$ is an ester, carbamate, carbonate, or sulfonate;

wherein when $R_1$ and $R_{10}$ are methyl, $R_2$, $R_3$, $R_5$, $R_6$, $R_8$, and $R_9$ are H, and $R_{14}$ is,

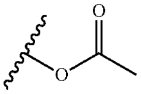, then $R_4$ and $R_7$ are both halogen; $R_4$ is hydrogen and $R_7$ is halogen; or $R_7$ is halogen and $R_4$ is hydrogen;

or a pharmaceutically acceptable salt thereof.

4. The compound of claim 1, wherein $R_{11}$ is a carbamate or an ester.

5. The compound of claim 3, wherein $R_{14}$ is a carbamate or an ester.

6. The compound of claim 1, wherein $R_{11}$ is selected from one of the following:

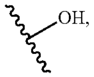 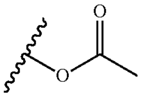, 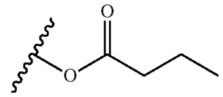,

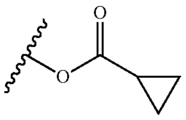, 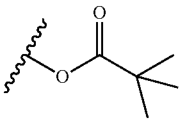,

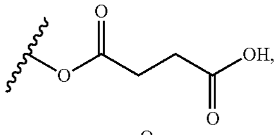 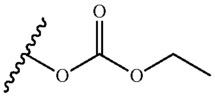,

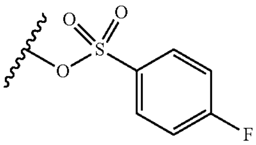, 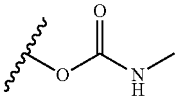,

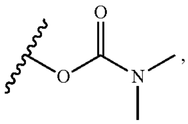, 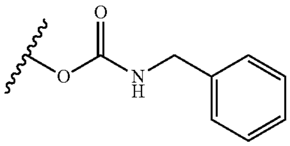, and

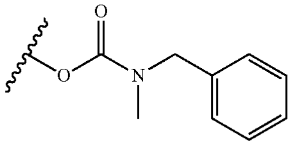.

7. The compound of claim 3, wherein $R_{14}$ is selected from one of the following:

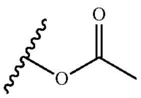, 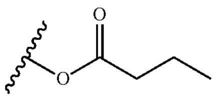,

-continued
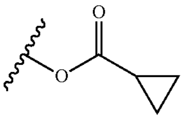, 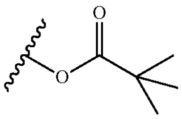,
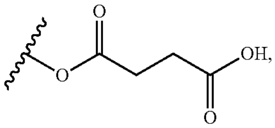, 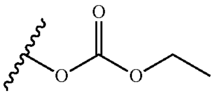,
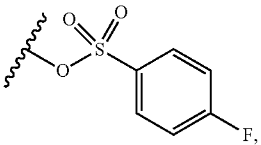, 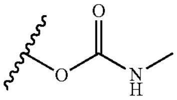,
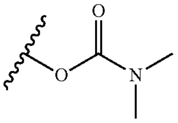, 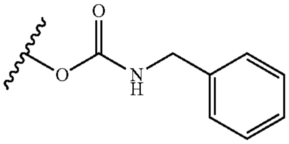, and
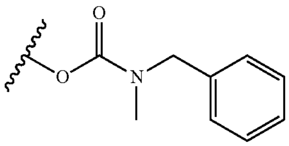.
8. The compound of claim 1, wherein $R_1$ and $R_{10}$ are independently methyl, ethyl, or a combination thereof.
9. The compound of claim 1, wherein $R_4$ and $R_7$ are halogen, hydrogen, or a combination thereof.
10. The compound of claim 1, wherein $R_2$, $R_3$, $R_5$, $R_6$, $R_8$, and $R_9$ are hydrogen.
11. The compound of claim 1, wherein the compound is:
4
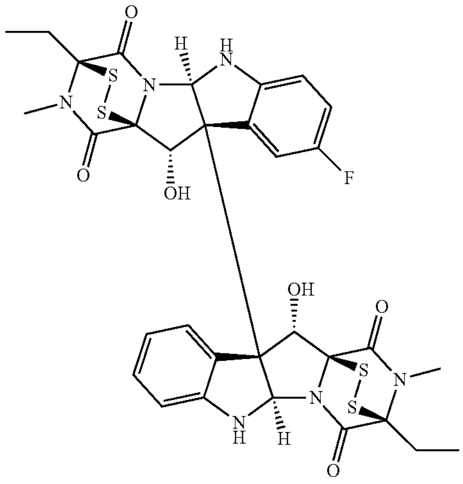,
-continued
5
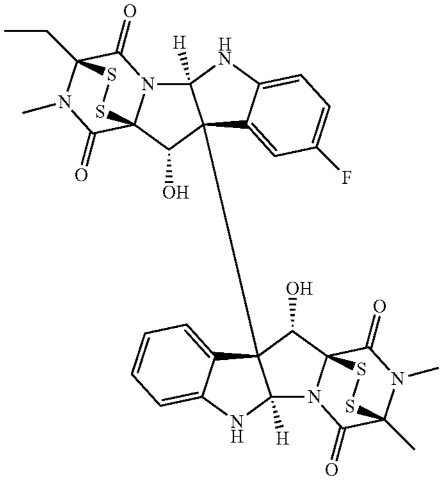,
6
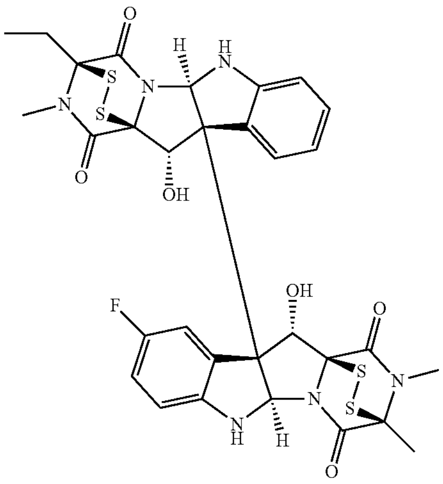,
7
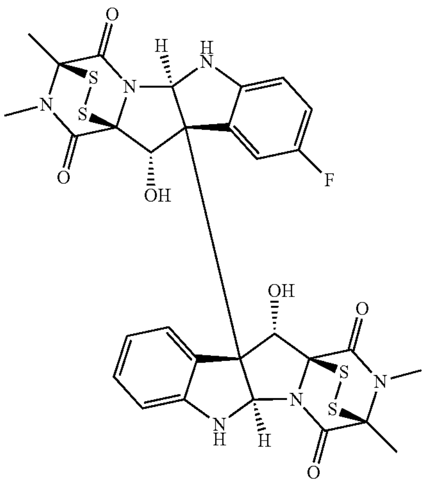, -continued
8
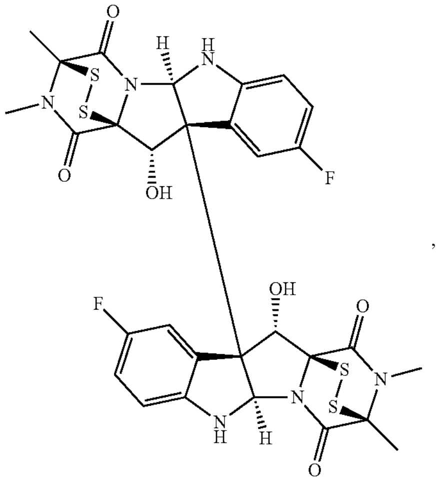
,
9
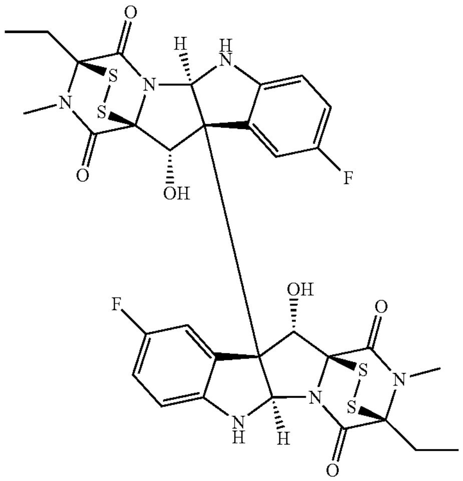
,
10
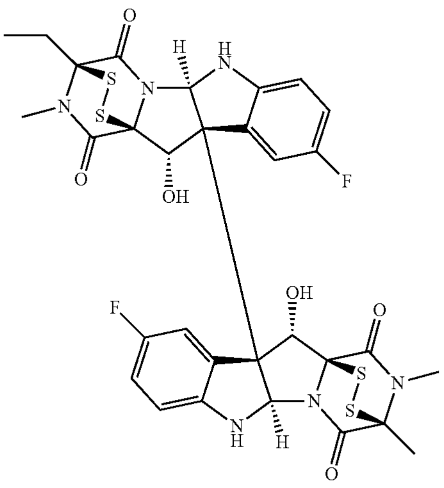
,
or a pharmaceutically acceptable salt thereof.
12. The compound of claim 1, wherein the compound is:
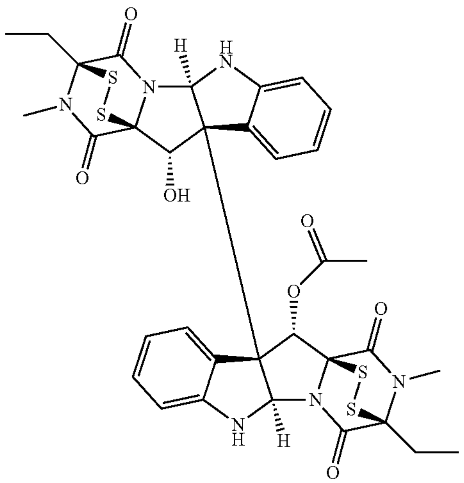
,
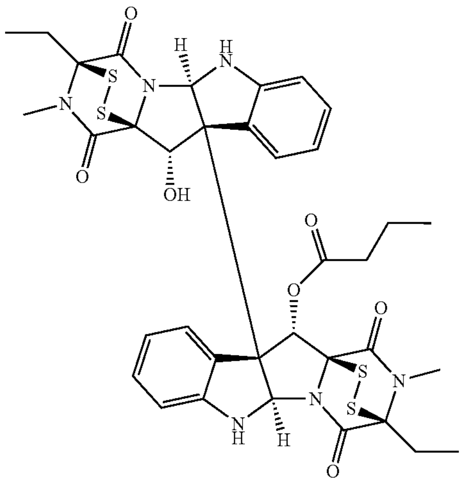
,
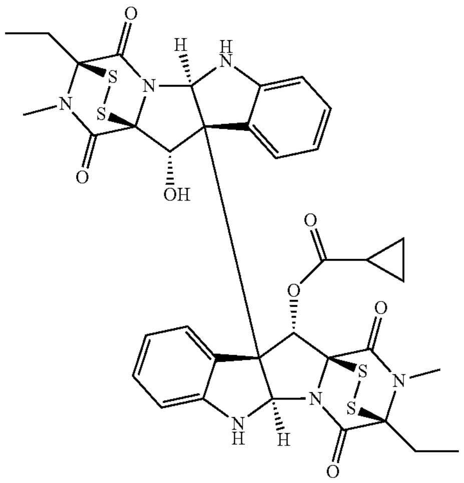
, -continued
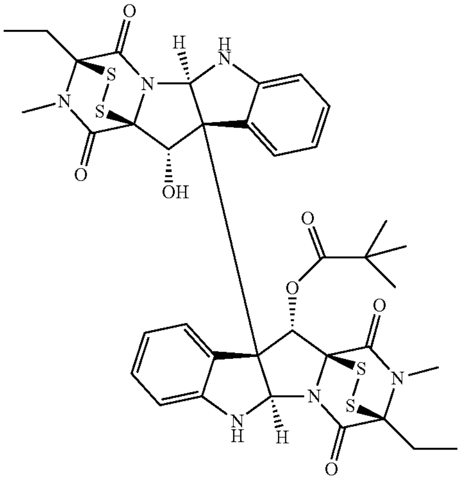
,
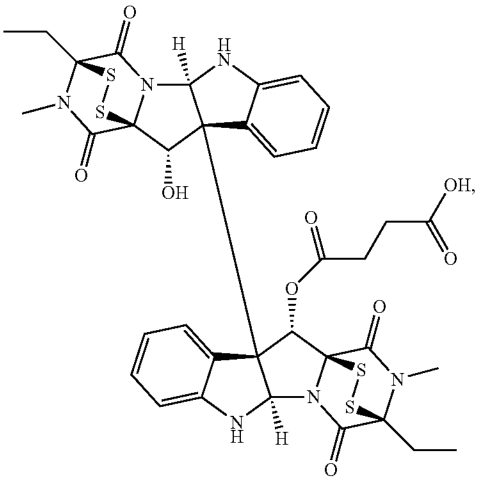
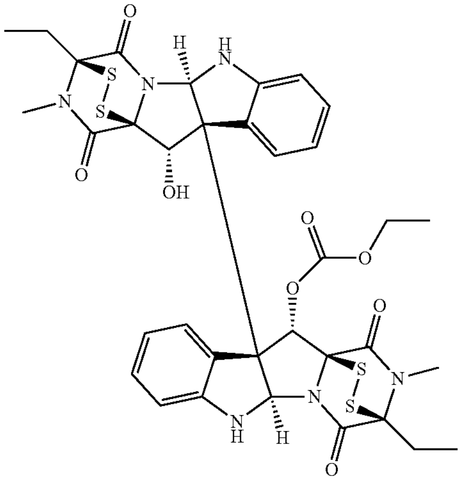
,
-continued
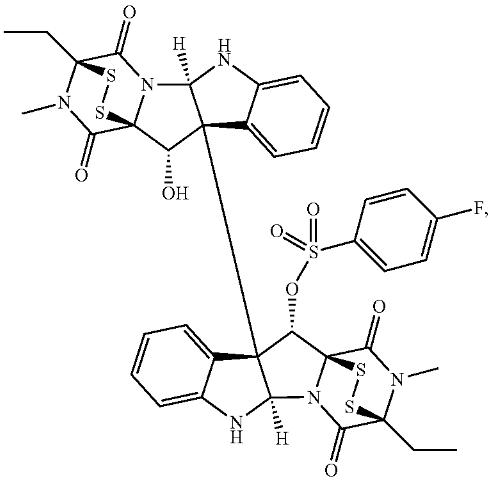
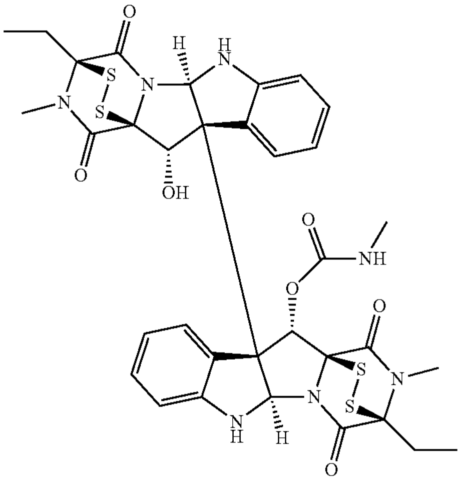
,
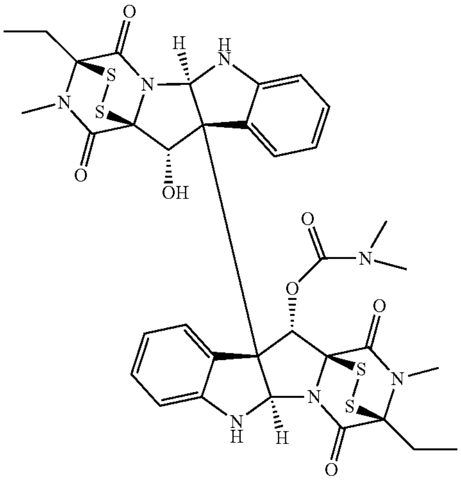
, -continued
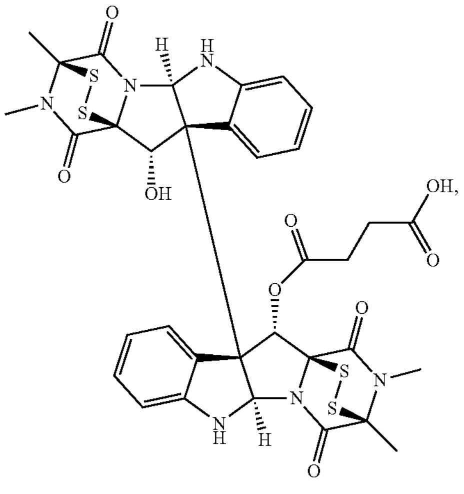 [SMILES: CN1C(=O)[C@]23SS[C@@]1(C)C(=O)N2[C@H]1Nc2ccccc2[C@@]1([C@@]12c4ccccc4N[C@@H]1N1C(=O)[C@]4(C)SS[C@]1(C(=O)N4C)[C@H]2OC(=O)CCC(=O)O)[C@@H]3O]
or a pharmaceutically acceptable salt thereof.
13. The compound of claim 1, wherein the compound is:
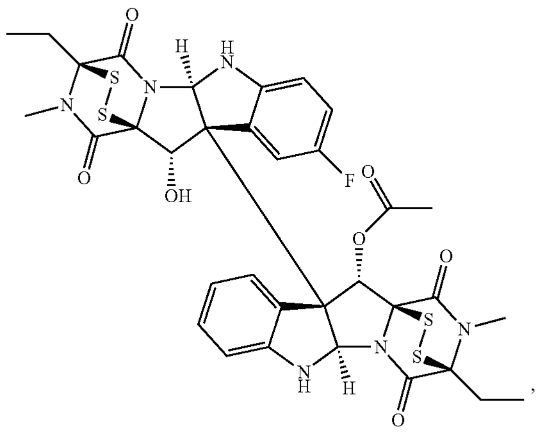
,
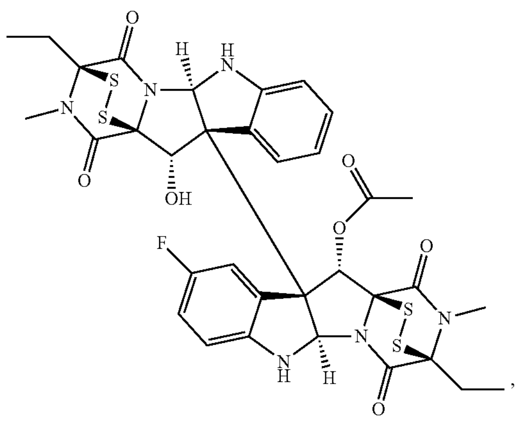
,
-continued
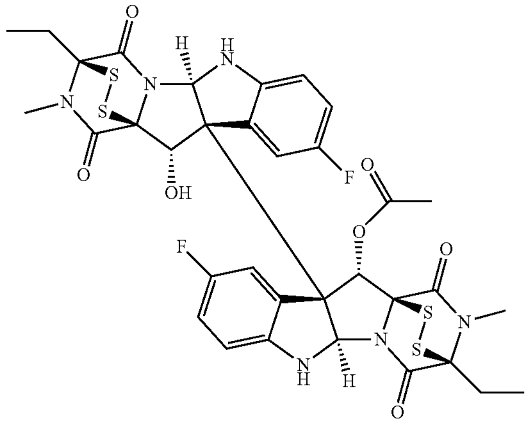
,
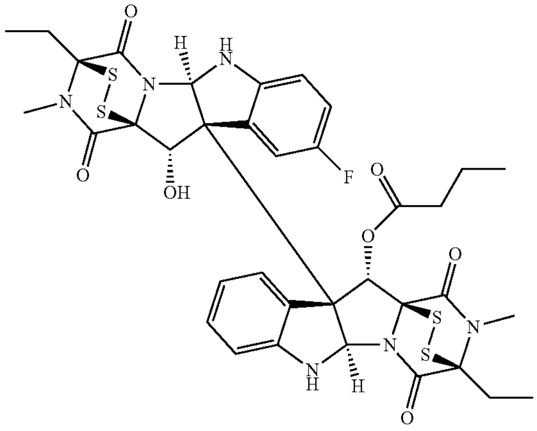
,
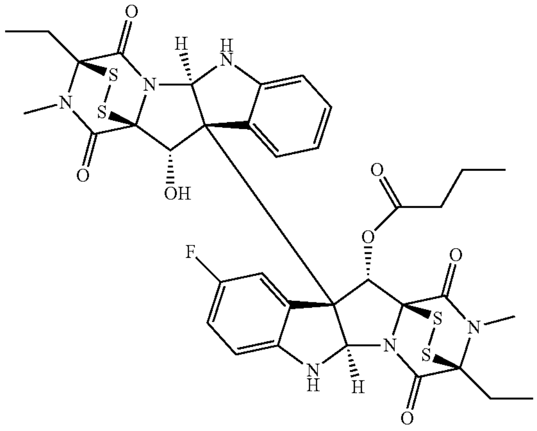
,
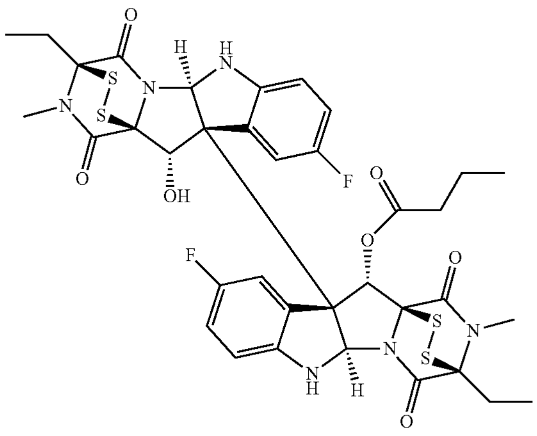
, -continued
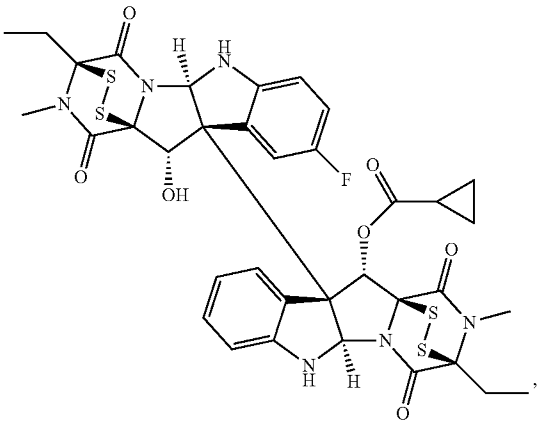
,
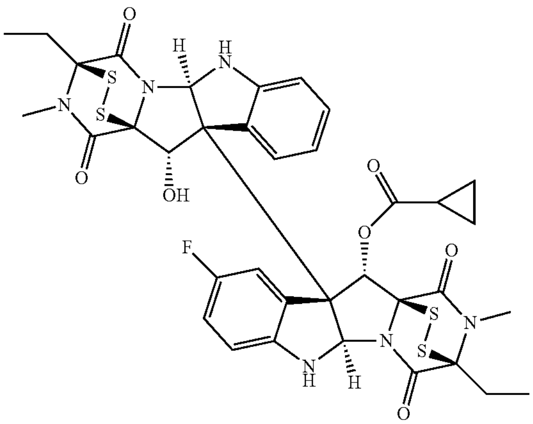
,
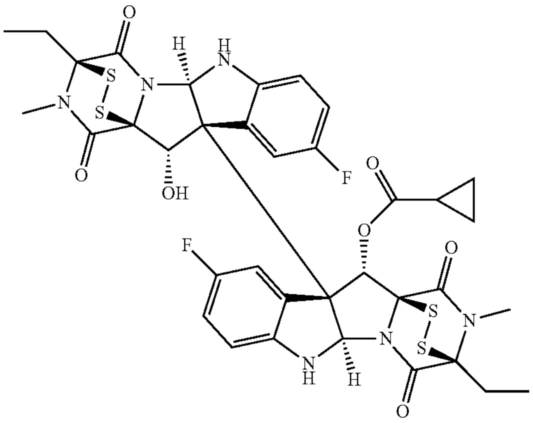
,
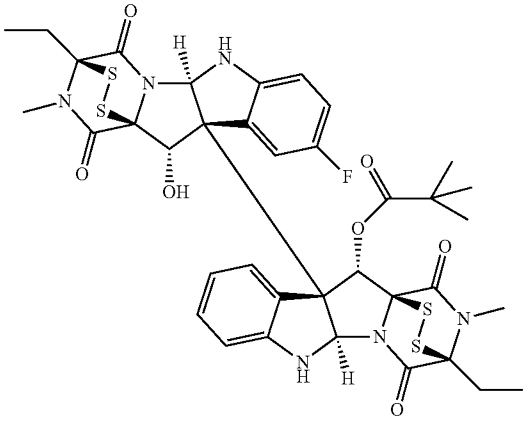
,
-continued
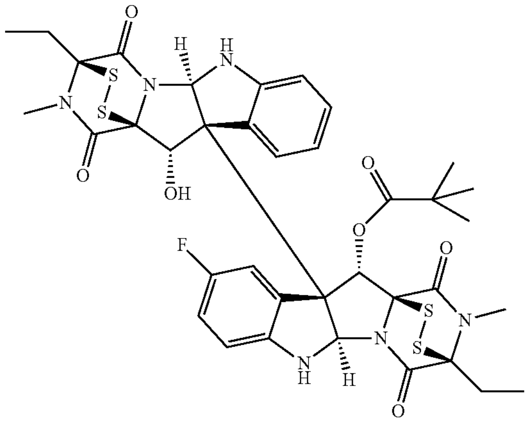
,
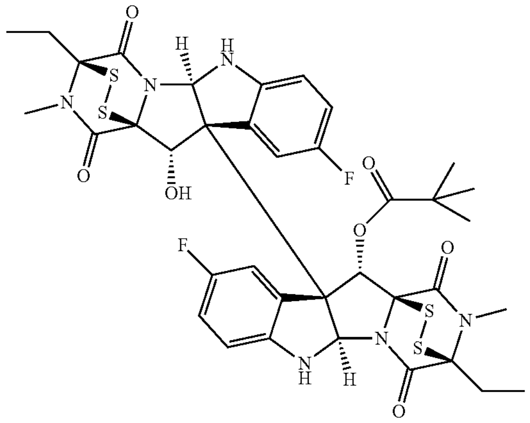
,
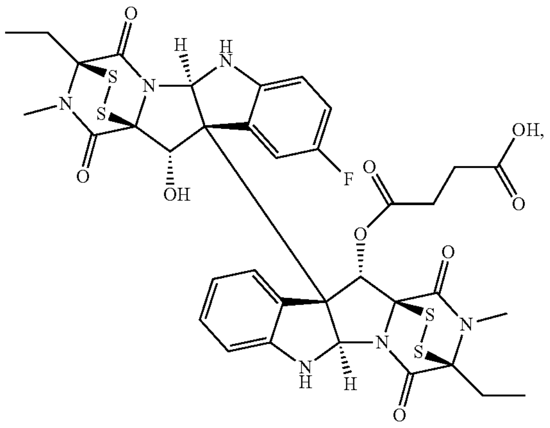
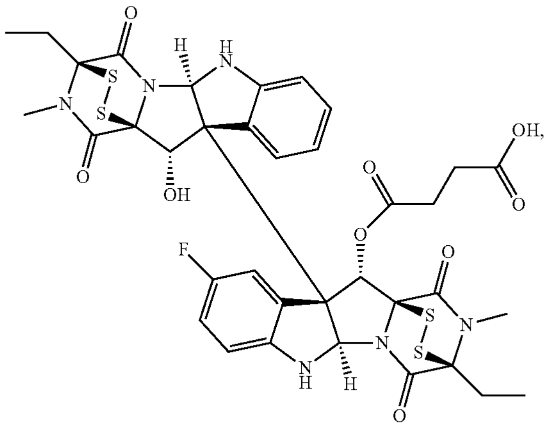

-continued
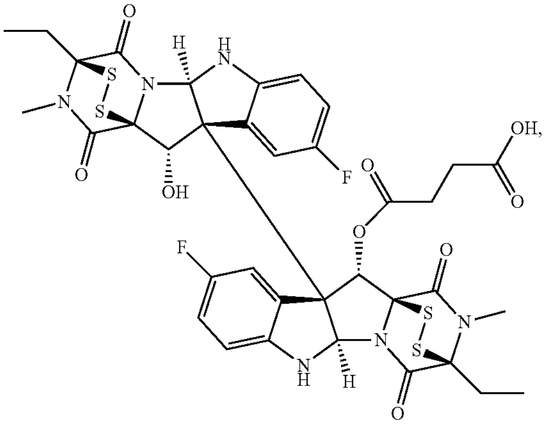
,
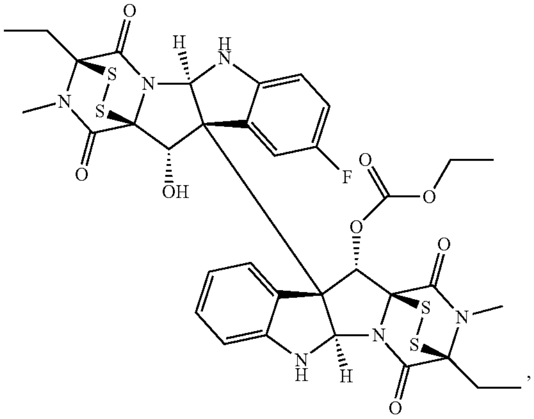
,
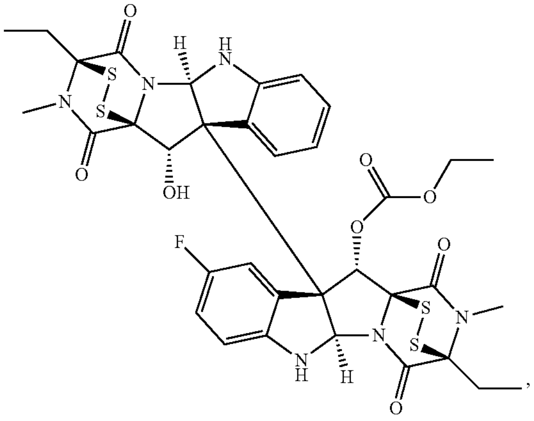
,
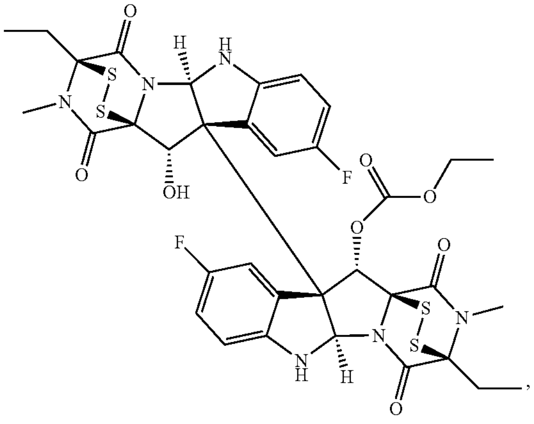
,
-continued
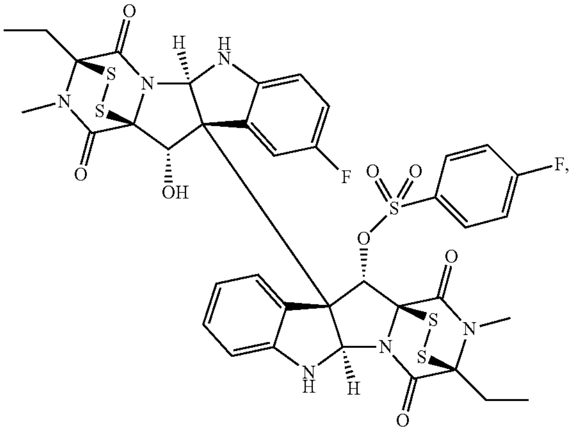
,
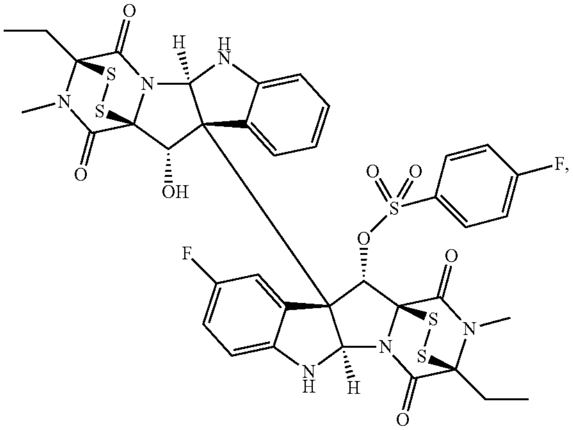
,
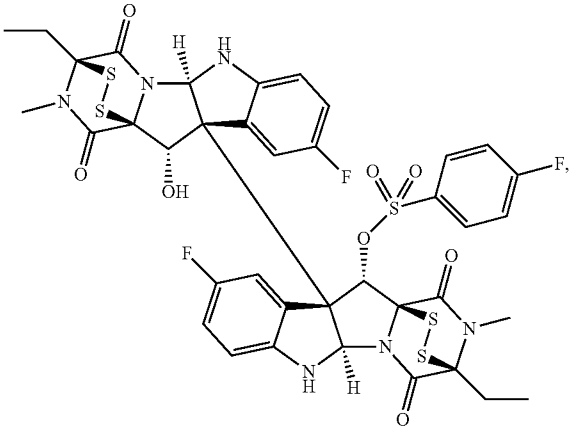
,
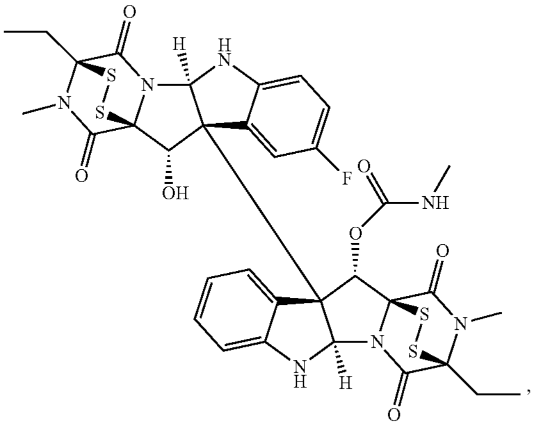
, -continued
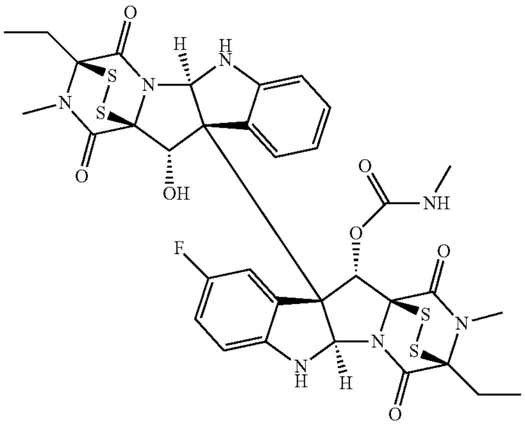
,
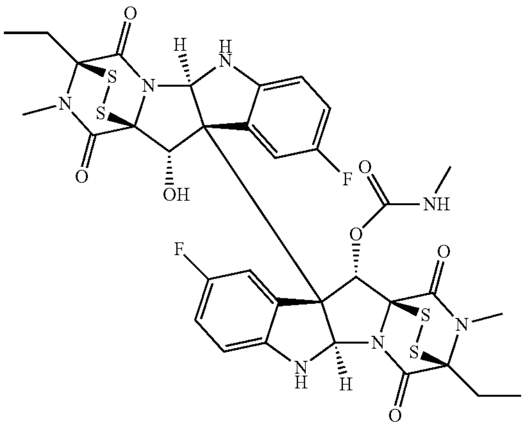
,
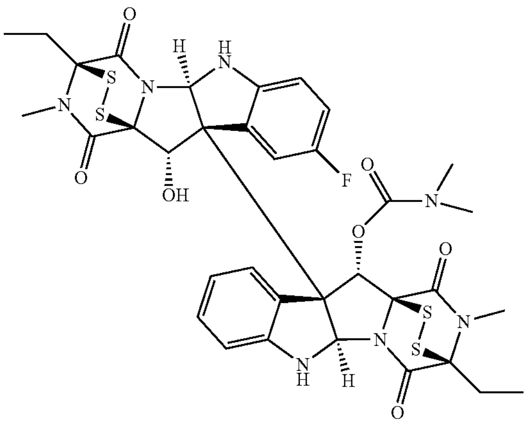
,
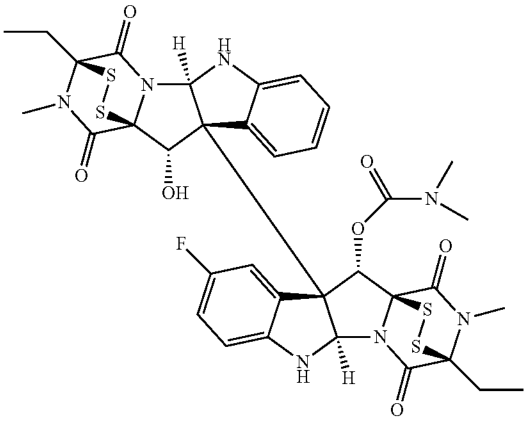
,
-continued
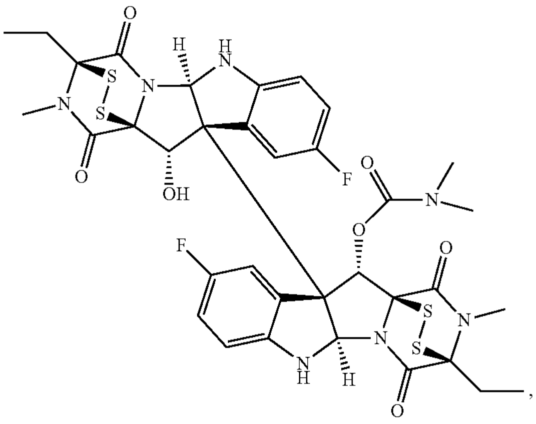
,
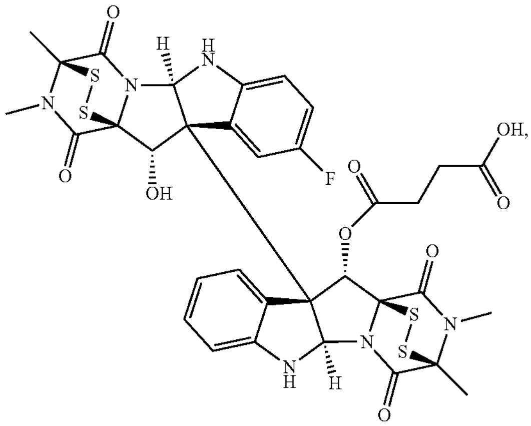
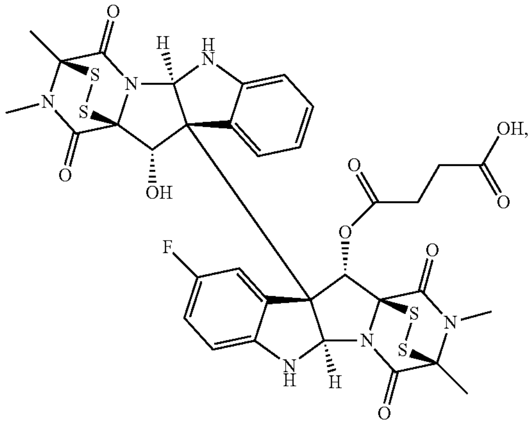
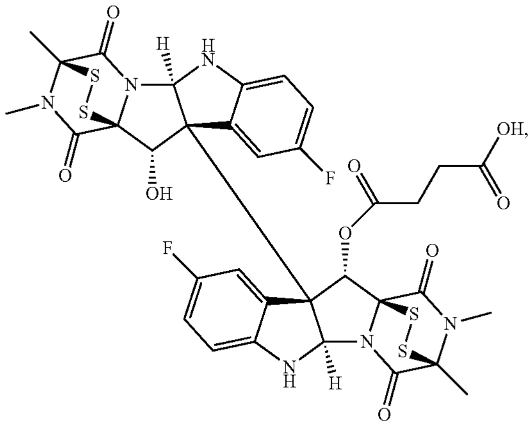

-continued
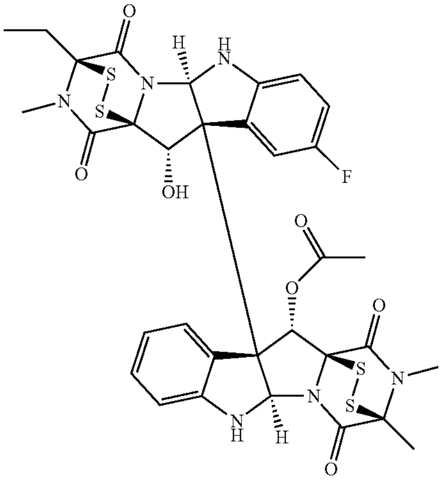
,
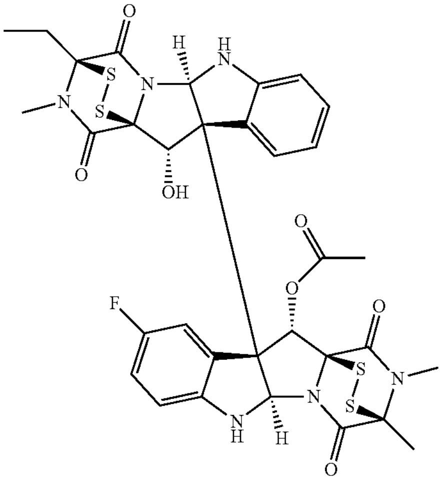
,
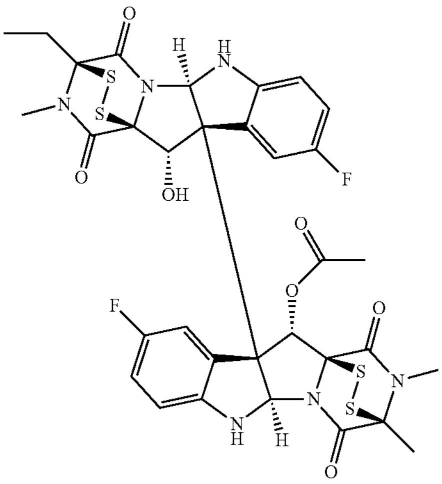
,
-continued
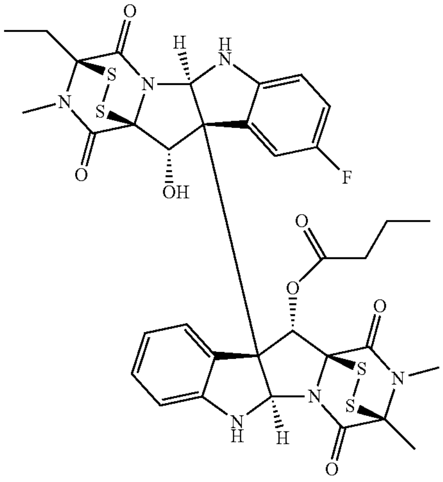
,
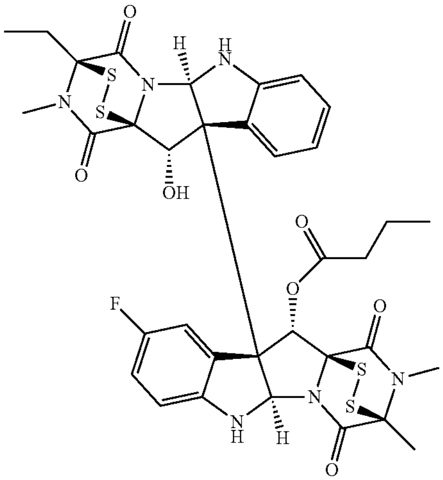
,
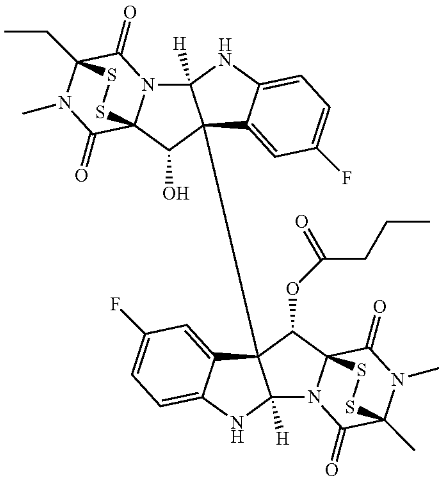
, -continued
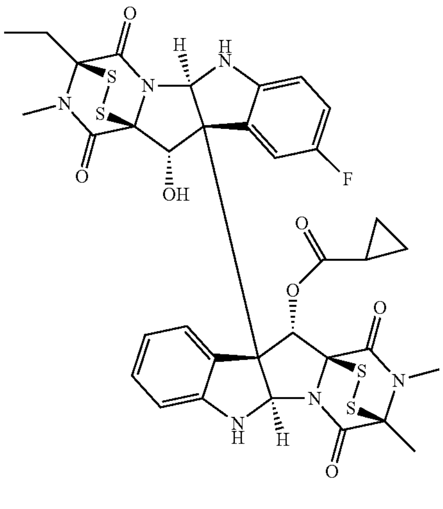
,
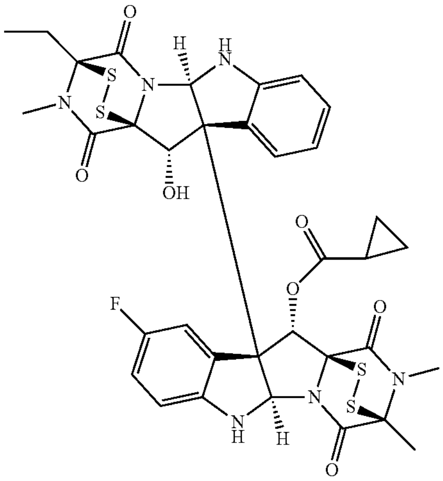
,
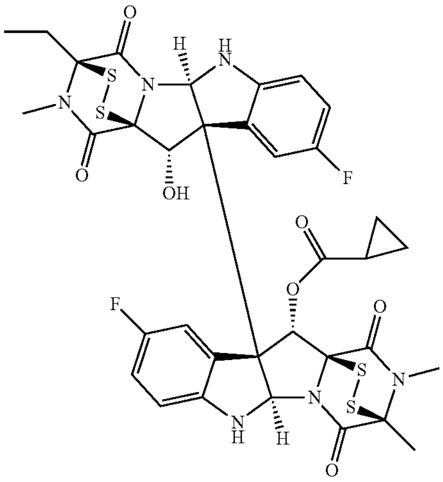
,
-continued
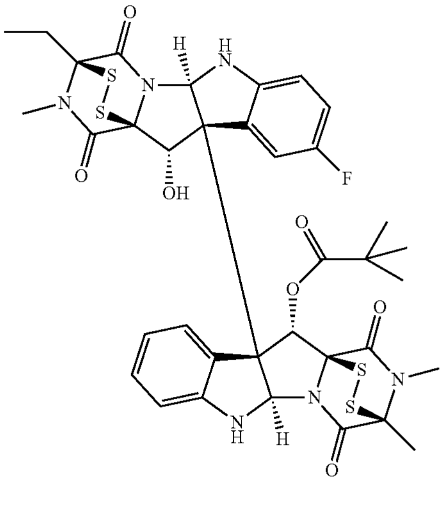
,
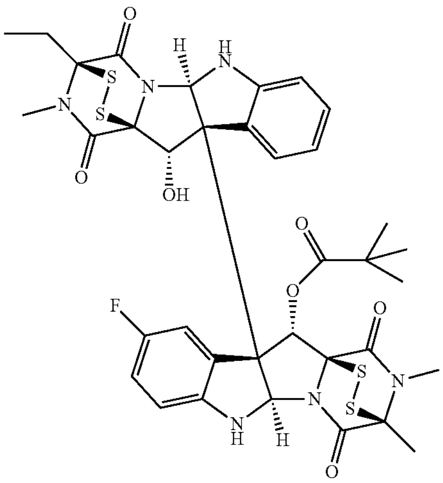
,
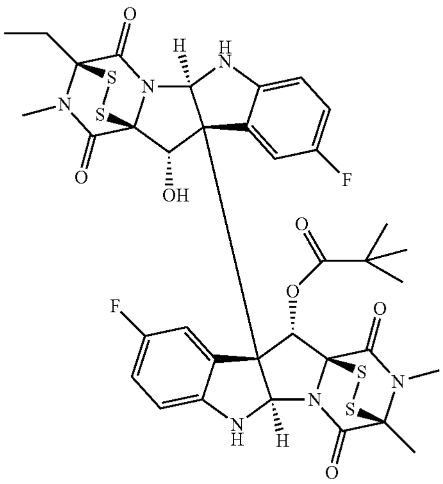
, -continued
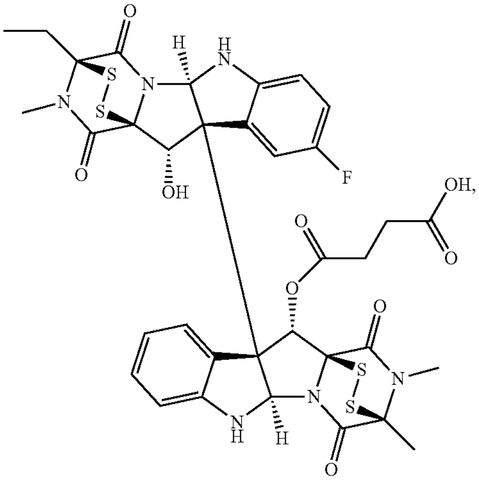
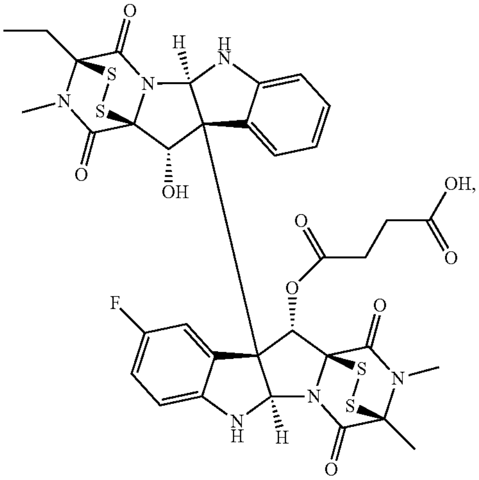
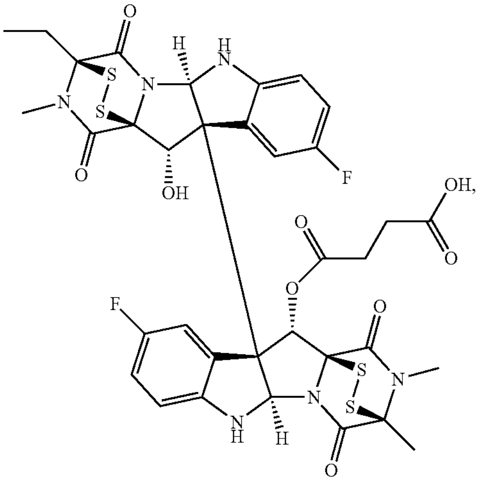
-continued
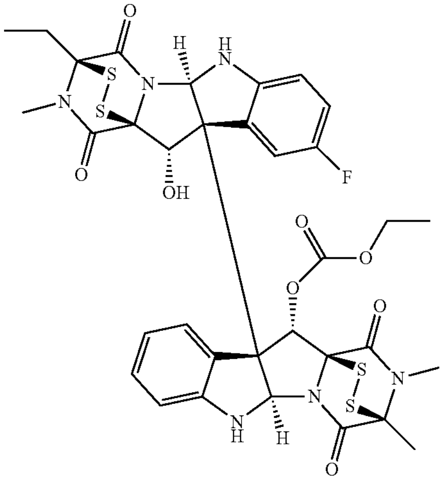
,
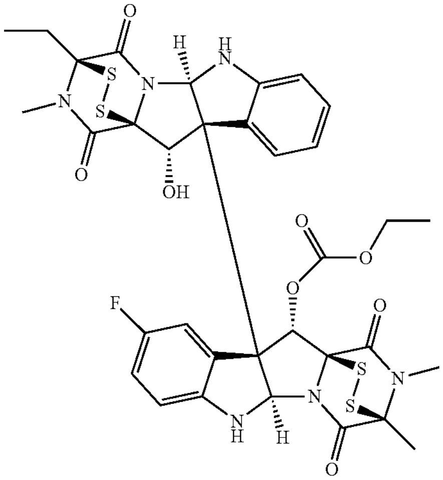
,
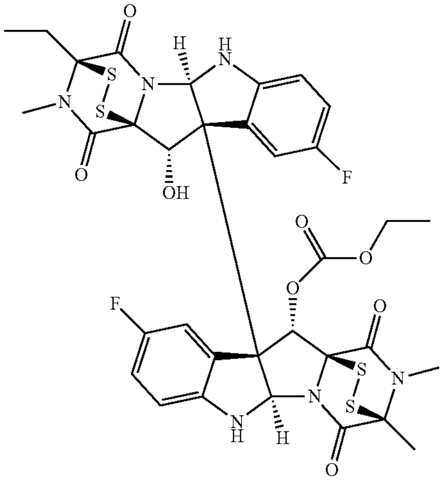
, -continued
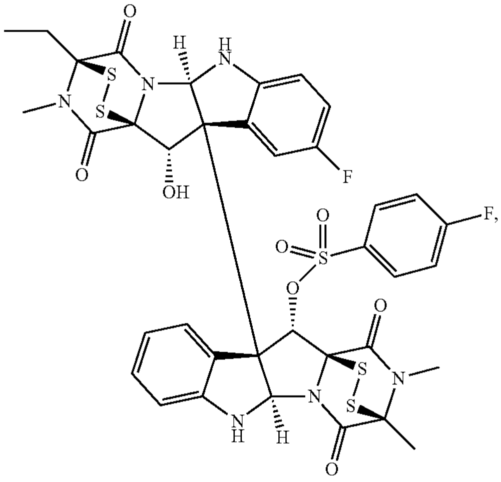
,
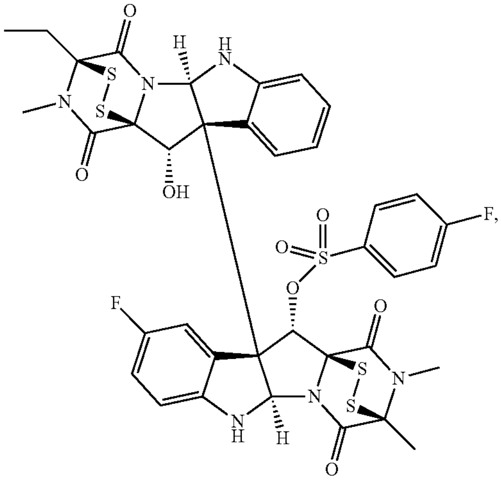
,
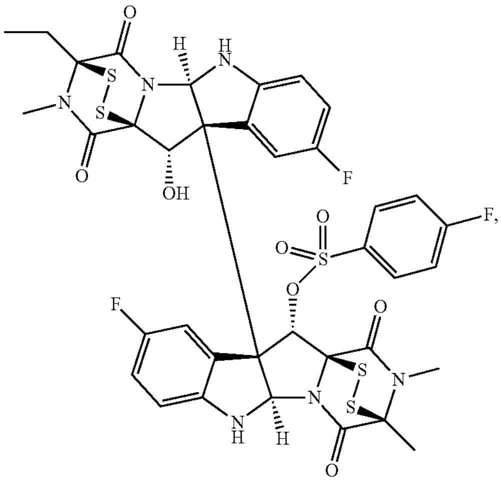
,
-continued
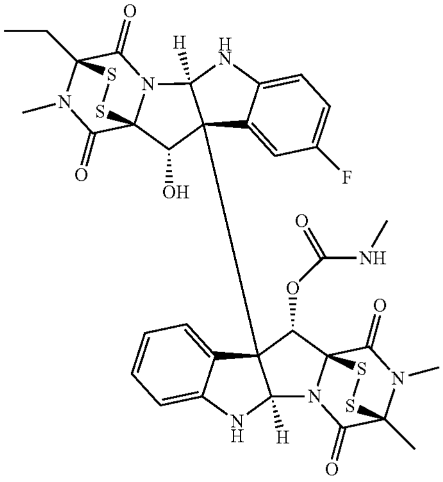
,
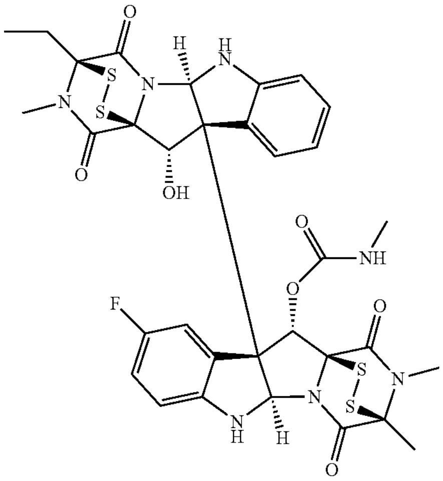
,
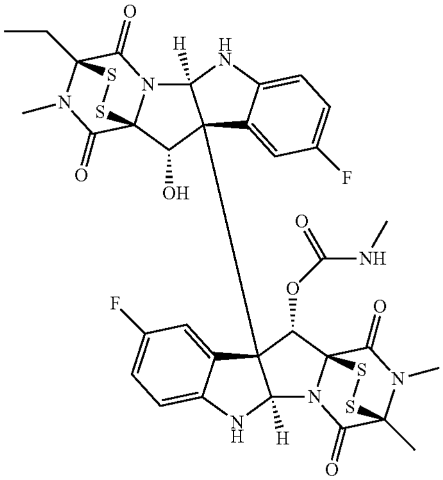
, -continued
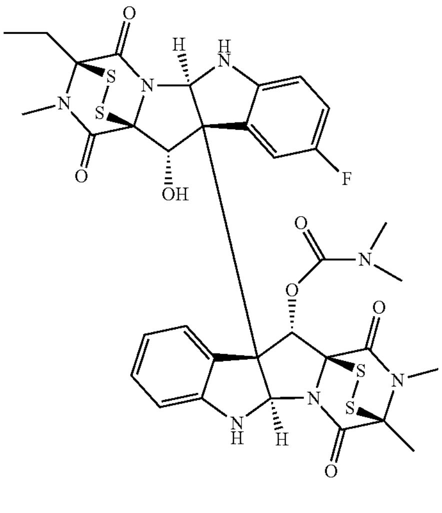
,
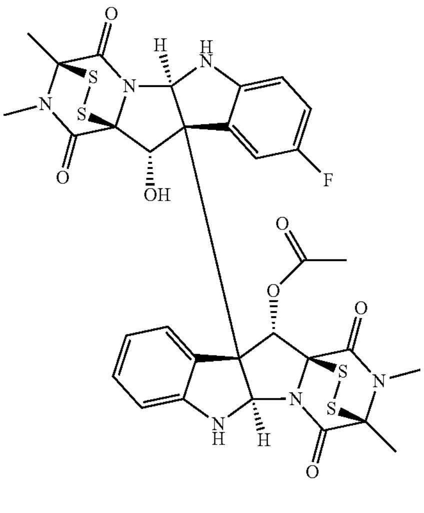
,
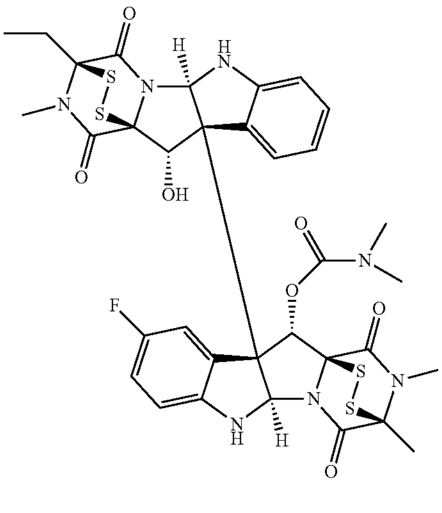
,
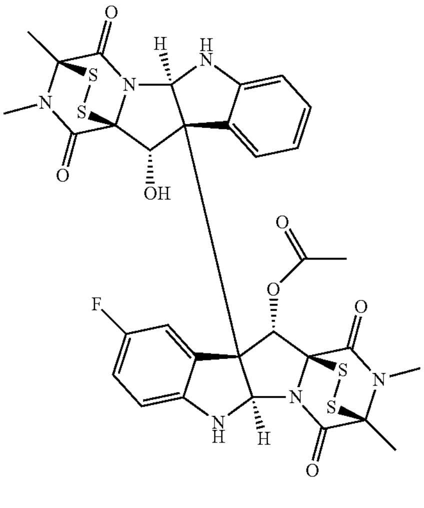
,
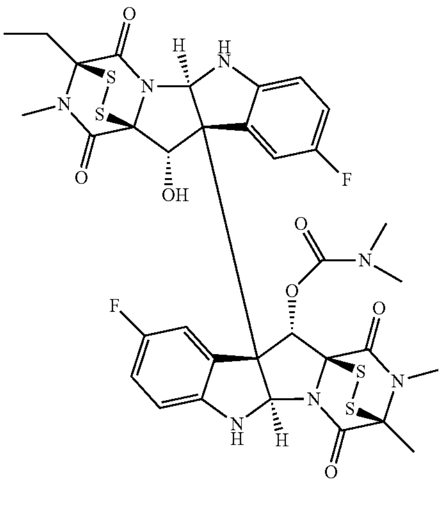
,
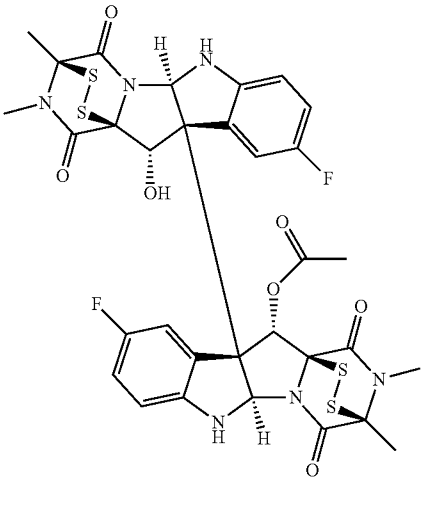
,

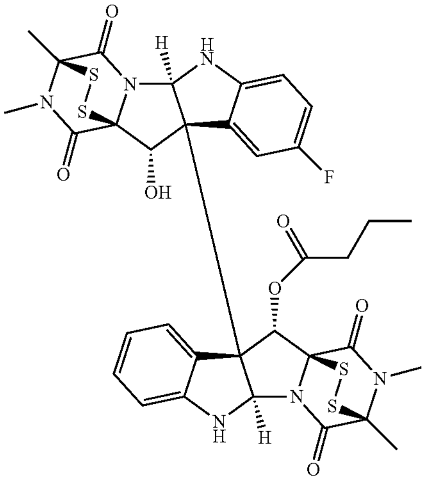
,
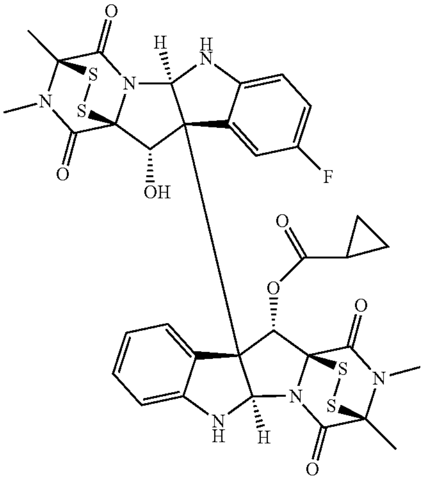
,
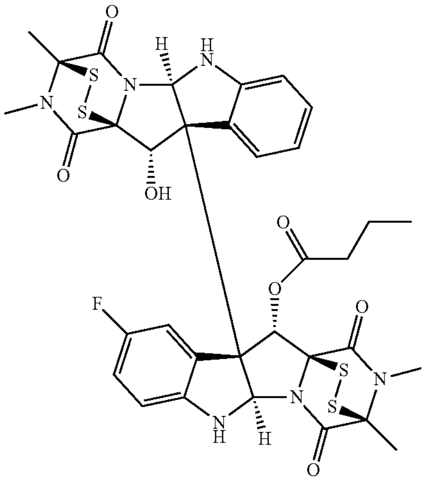
,
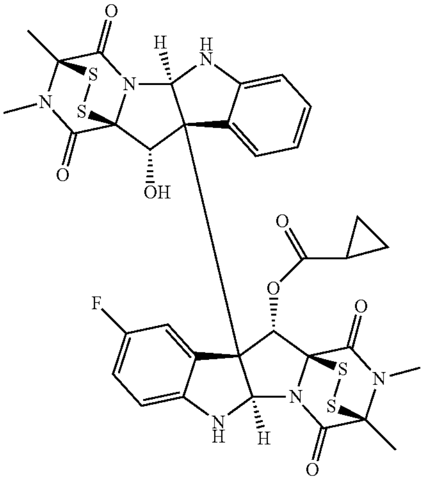
,
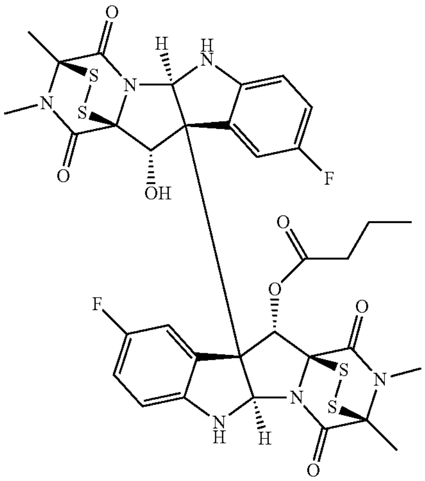
,
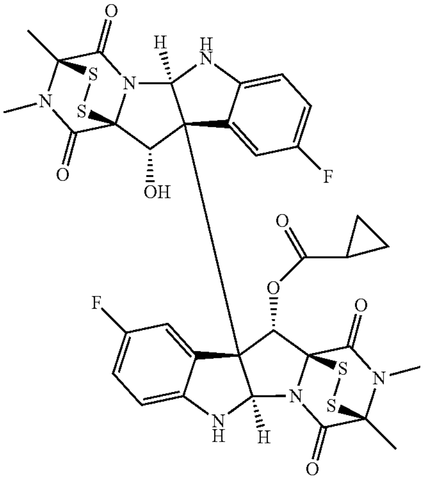
, -continued
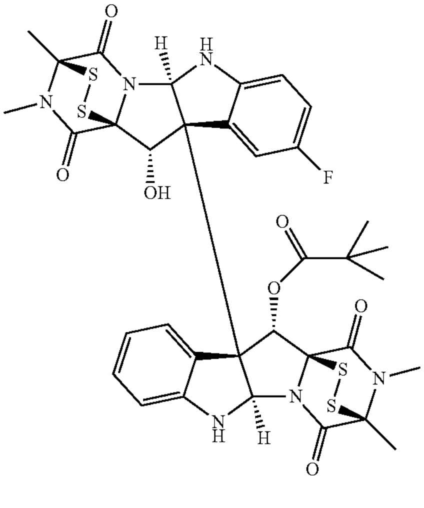
,
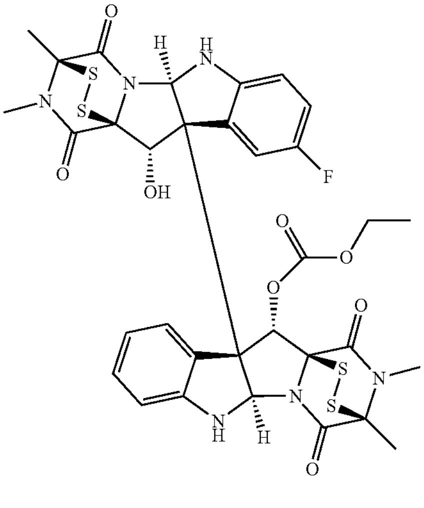
,
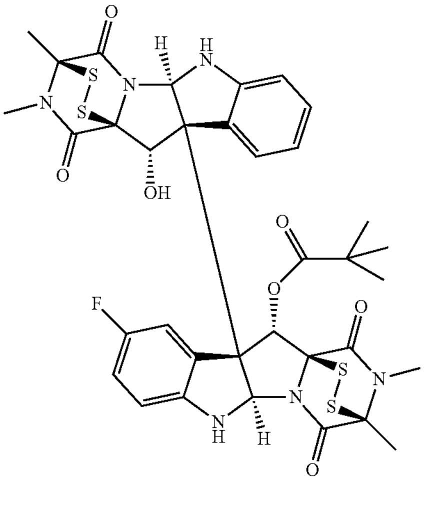
,
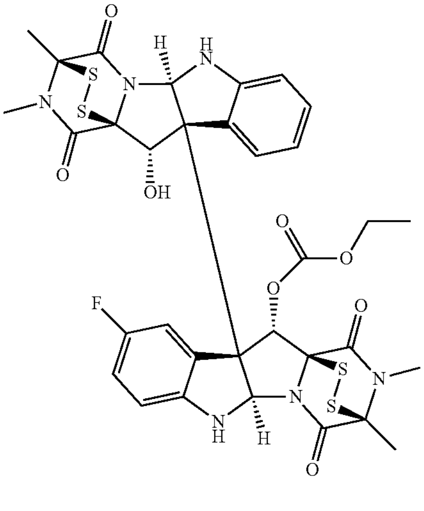
,
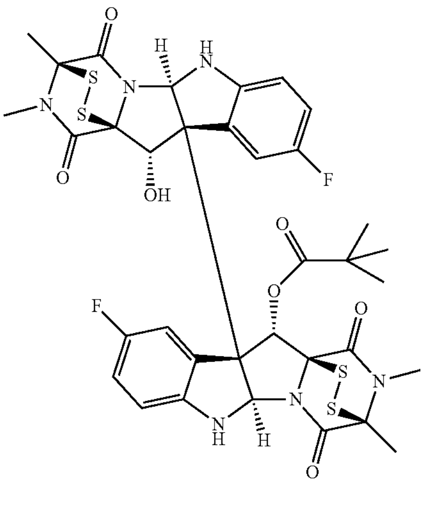
,
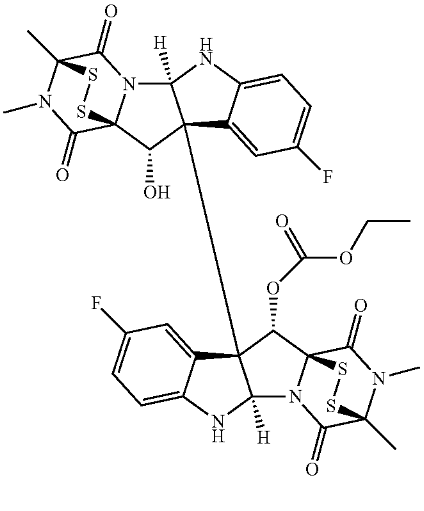
, -continued
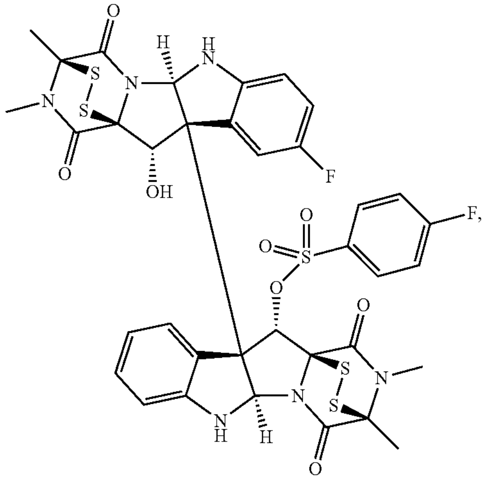
,
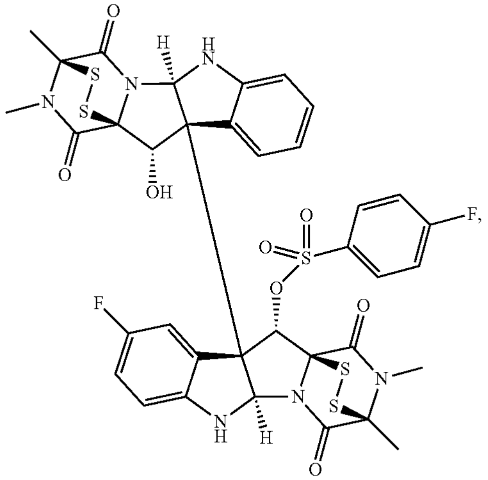
,
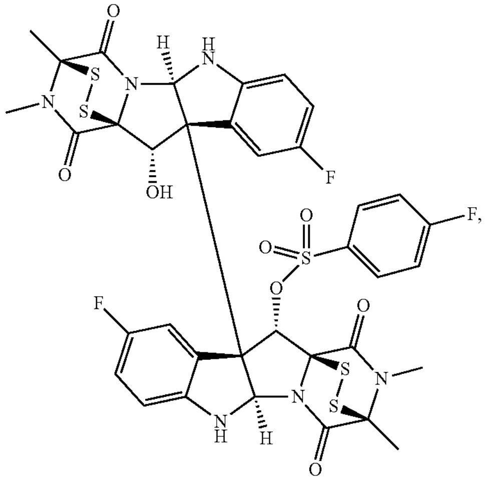
,
-continued
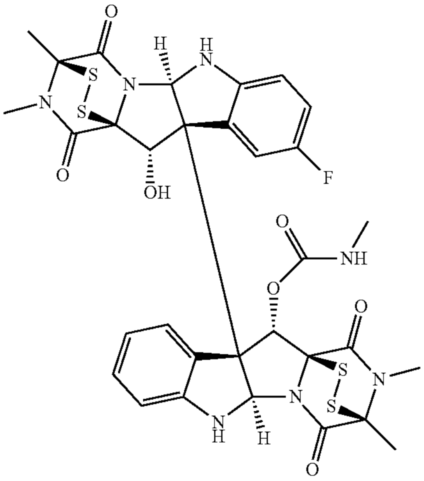
,
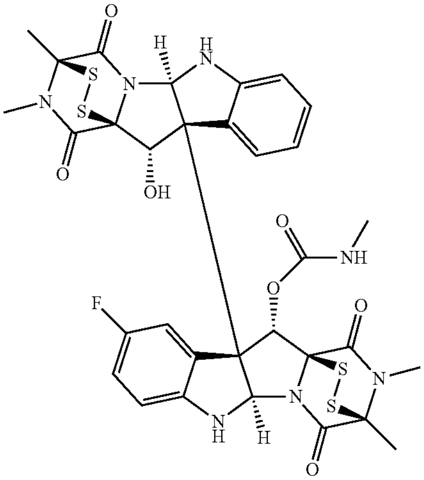
,
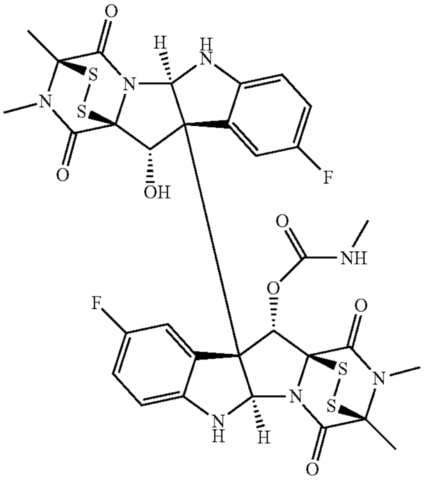
, -continued

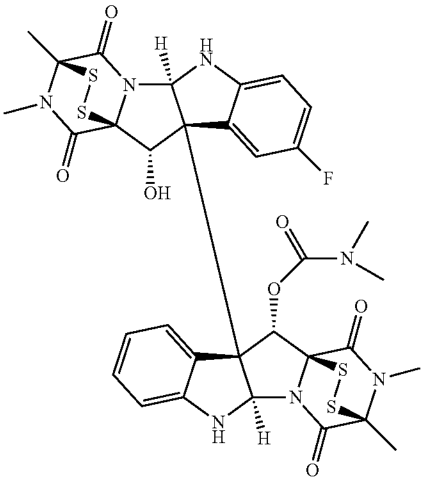

,

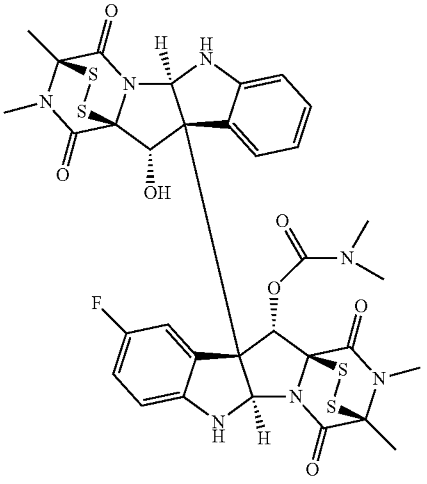

,

-continued

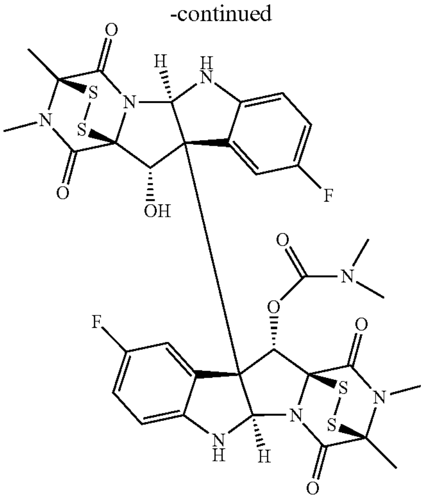

, or a pharmaceutically acceptable salt thereof.

14. The compound of claim 12, wherein the compound is:

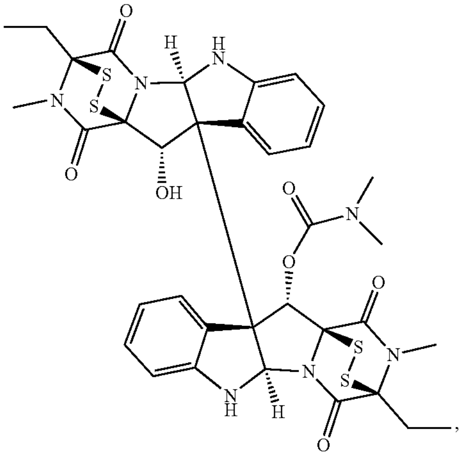 [SMILES: CC[C@@]12SS[C@]3(C(=O)N1C)[C@@H](O)[C@]1([C@@]45c6ccccc6N[C@@H]4N4C(=O)[C@]6(CC)SS[C@]4(C(=O)N6C)[C@H]5OC(=O)N(C)C)c4ccccc4N[C@@H]1N3C2=O]

, or a pharmaceutically acceptable salt thereof.

15. A pharmaceutical composition comprising a compound of claim 1 and one or more pharmaceutically acceptable carriers.

16. A method for treating cancer comprising administering to a subject in need thereof a pharmaceutical composition comprising a therapeutically effective amount of a compound of claim 1;

wherein the cancer is breast cancer, ovarian cancer, melanoma, or any combination thereof.

17. The method of claim 16, wherein the pharmaceutical composition is administered by one or more routes selected from the group consisting of buccal, sublingual, intravenous, subcutaneous, intradermal, transdermal, intraperitoneal, oral, eye drops, parenteral, and topical administration.

* * * * *